United States Patent
van Kan et al.

(10) Patent No.: US 7,968,773 B2
(45) Date of Patent: Jun. 28, 2011

(54) TOMATO PLANTS HAVING HIGHER LEVELS OF RESISTANCE TO BOTRYTIS

(75) Inventors: Johannes Arnoldus Laurentius van Kan, Rhenen (NL); Arjen ten Have, Mar del Plata (AR); Willem Hendrik Lindhout, Wageningen (NL); Hendrikus Johannes Finkers, Wageningen (NL); Remco van Berloo, Wageningen (NL); Adriaan Willem van Heusden, Wageningen (NL)

(73) Assignee: Monsanto Invest N.V., Amstelveen (NL)

( * ) Notice: Subject to any disclaimer, the term of this patent is extended or adjusted under 35 U.S.C. 154(b) by 0 days.

(21) Appl. No.: 11/738,279

(22) Filed: Apr. 20, 2007

(65) Prior Publication Data

US 2007/0300314 A1 Dec. 27, 2007

Related U.S. Application Data

(63) Continuation of application No. PCT/NL2005/000762, filed on Oct. 24, 2005.

(30) Foreign Application Priority Data

Oct. 25, 2004 (EP) .................................... 04077931

(51) Int. Cl.
*A01H 1/00* (2006.01)
*A01H 1/02* (2006.01)
*A01H 5/00* (2006.01)
*C12N 15/09* (2006.01)

(52) U.S. Cl. ...................... 800/317.4; 800/260; 800/265; 800/267; 800/279; 800/277; 435/419; 435/468; 435/411

(58) Field of Classification Search ........................ None
See application file for complete search history.

(56) References Cited

U.S. PATENT DOCUMENTS 5,591,616 A 1/1997 Hiei et al. .................. 435/172.3

FOREIGN PATENT DOCUMENTS

WO WO 02/085105 10/2002
WO WO 03/090521 11/2003

OTHER PUBLICATIONS

Bai et al. MPMI (2003), vol. 16(2):169-176.*
Bernacchi et al., "An interspecific backcross of *Lycopersicon esculentum* x *L. hirsutum*: . . . ," *Genetics*, 147:861-877 (1997).
Bernacchi et al., "Advanced backcross QTL analysis in tomato . . . ," *Theor. Appl.. Genet.*,97:381-397 (1998).
Brouwer et al., "QTL analysis of quantitative resistance to *Phytophthora infestans*,(late blight) . . . ," *Genome*, 47:475-492 (2004).
Brouwer et al., "Fine mapping of three quantitative trail loci for late blight resistance in tomato using near isogenic lines (NILs) and sub-NILs," *Theor. Appl. Genet.*, 108:628-638 (2004).
Denby et al., "Identification of *Botrytis cinerea* susceptibility loci in *Arabidopsis thaliana*," *Plant J.*, 38:473-486 (2004).
Doganlar et al., "Mapping Quantitative Trait Loci in Inbred Backcross Lines of *Lycopersicon pimpinellifolium* (LA1589)," *Genome*, 45:1189-1202 (2002).
Egashira et al., "Screening of wild accessions resistant to gray mold (*Botrytis cinerea* Pers.) in *Lycopersicon*," *Acta Physiologiae Plantarum*, 22:324-326 (2000).
Fulton et al., "Identification, Analysis and Utilization of a Conserved Ortholog Set (COS) Markers for Comparative Genomics in Higher Plants," *The Plant Cell*, 14(7):1457-1467 (2002).
Grandillo and Tanksley, "QTL analysis of horticultural traits differentiating the cultivated tomato from the closely related species *Lycopersicon pimpinellifolium*," *Theor. Appl. Genet.*, 92:935-951 (1996).
Guimarães et al., "resistance to *Botrytis cinerea* in *Solanum lycopersicoides* is dominant in hybrids with tomato, and involves hyphal death," *Eur. J. Plant Path.*, 110:13-23 (2004).
Nicot et al., "Differences in susceptibility of pruning wounds and leaves to infection by *Botrytis cinerea* among wild tomato accessions," *TGC Report*, 52:24-26 (2002).
Tanksley et al., "High density molecular linkage maps of the tomato and potato genomes," *Genetics*, 132:1141-1160 (1992).
Tanksley et al., "Advanced backcross QTL analysis in a cross between an elite processing line of tomato and its wild relative *L. pimpinellifolium*," *Theor. Appl. Genet.*, 92:213-224 (1996).
Urbasch, "Resistenz verschiedener Kultur- und Wildtomatenpflanzen (*Lycopersicon spp.*) gegenüber *Botrytis cinerea* Pers," *J. Phytopathol.*, 116:344-351 (1986).
Young, "QTL Mapping and Quantitative Disease Resistance in Plants," *Annu. Rev. Phytopathol.*, 34:479-501 (1996).
Zhang et al., "A molecular linkage map of tomato displaying chromosomal locations of resistance gene analogs based on a *Lycopersicon esculentum* x *Lycopersicon hirsutum* cross," *Genome*, 45:133-146 (2002).

\* cited by examiner

*Primary Examiner* — Medina A Ibrahim
(74) *Attorney, Agent, or Firm* — Banner & Witcoff, Ltd.

(57) ABSTRACT

The present invention relates to a method for detecting a quantitative trait locus (QTL) associated with resistance to *Botrytis cinerea* in tomato, including the steps of crossing a *Botrytis*-resistant donor tomato plant with a non-resistant, or *Botrytis*-susceptible, recipient tomato plant, contacting one or more offspring plants with an infective amount of *Botrytis*, quantitatively determining the disease incidence and/or the rate of lesion growth in the one or more offspring plants, establishing a genetic linkage map that links the observed disease incidence and/or rate of lesion growth to the presence of chromosomal markers of the donor tomato plant in the one or more offspring plants, and assigning to a QTL the contiguous markers on the map that are linked to a reduced disease incidence and/or a reduced lesion growth rate.

15 Claims, 5 Drawing Sheets

SEQUENCE LISTING

```
<160> NUMBER OF SEQ ID NOS: 35

<210> SEQ ID NO 1
<211> LENGTH: 476
<212> TYPE: DNA
<213> ORGANISM: Artificial
<220> FEATURE:
<223> OTHER INFORMATION: RFLP marker TG301, forward sequence

<400> SEQUENCE: 1
ttgtaactta ctaaattaag agctcaggat gaacagaaca cgaattatta gttcatatta     60
agcaagaaac ttaaaaaact tcaccttctc caacatactc tacaacaaac tcttttgtct    120
tgatatcttc atctgccaca atcccagtgc cacatttctc agtctgcacg ttatgagtca    180
acaaactttt agttttttag atgattattg cttggttttc aaaagaaacg aaaataagaa    240
gaatacaaaa taaccaacat ttctttactt cttcaccaga tacacaactg aattaaatgc    300
aaaaatagat atgaaaaatg ttaccagcct gcacttttga tgcagattgt acttgtttgc    360
aattgaaaag tgtcgaatgg tcattttttgg taaaaactga tgaatgtggt attttgagaa    420
aggatttatg acggtccttt tgcttaatta tccctcttat aaacgttagt aaaggc        476

<210> SEQ ID NO 2
<211> LENGTH: 485
<212> TYPE: DNA
<213> ORGANISM: Artificial
<220> FEATURE:
<223> OTHER INFORMATION: RFLP marker TG301, reverse sequence

<400> SEQUENCE: 2
tattctgaat ctggaaaatt gttctgccaa tttctttgac caaccagaca ataccctttt     60
aatctaagac cctaattaca aggttactga caatcacttt tgacaccaat gtctttgata    120
aagcactgtt aaaattttca gatgtgcttt aatactctgc atcctttta ggaactcttt    180 tgtctacttt cactttttaa aagaaagaac ttaaggagag gacatactta ttatttttgc    240
```

```
atttctata tcaagtaaag tgagaagact tccattaatt tgcatccagc ggatgctaat    300
ggctacaaca tagctacttt aagcaaatag gtgatttgat caagattctt tacgttttca    360
agatcacagc aacaaaaagg gttccttaaa aacctagcct ttactaacgt ttataagagg    420
gataattaag caaaaggacc gtcataaatc ctttctcaaa ataccacatt catcagtttt    480
tacca                                                                485
```

```
<210> SEQ ID NO 3
<211> LENGTH: 466
<212> TYPE: DNA
<213> ORGANISM: Artificial
<220> FEATURE:
<223> OTHER INFORMATION: RFLP marker TG460, forward sequence

<400> SEQUENCE: 3
ccttagtttt gaaatcttta agtagcaatt agtaatcggt agctctccag tatgaaaagt    60
tcataatcac ttggtggatc tcttattatt tgcatcattt gtgtgcaata ggcataagag    120
gtagtcattt cacaatgcct ctgaaatgtg tgcattgaca tttgagaaca cttgaggatg    180
ggatacactc tctgtcatca ggaactactt aggtgacaaa tagatgtgaa gattcacggc    240
atagtgtctt ttgatccata tcataaccag aaagtgagta tccccatttc tcacattagc    300
tatatgaagg aagaaaggga aaacaaagga aagcgctacc cttattcgtc gaaagctagc    360
cttcatgata aaccaaatga aattagaaaa atttaagaac tttgctatag cttcaaagaa    420
atcttttaga ttcttgttta caaagttttg ctgatctttc ttacat                   466
```

```
<210> SEQ ID NO 4
<211> LENGTH: 486
<212> TYPE: DNA
<213> ORGANISM: Artificial
<220> FEATURE:
<223> OTHER INFORMATION: RFLP marker TG460, reverse sequence

<400> SEQUENCE: 4
ttatgatgct caaaatttct tattttagac agactcgaaa tgtgactatt ccagagaaaa    60
ataaacaaga tccctcggga cactgaacct gagaacaggt tcaaattccc tactgtaccc    120
caacagacaa agggaagaga gagctatcag tttctctttg gtttgagaaa aaacataata    180
gtatggagtg taccagatgc ttcaggattt cagacatgtt ctgacttgtt acctaatgta    240
tttgatttca tagtataaat cttaggtgtt ctgcttgact agaagtatgg aaagtcattc    300
ttgtcagtag tcagtcttga gatataagat ataatttgat atacatctaa atagatcttg    360
gattcattag ataagttcaa caagcatggg tcaataagca cattgatcaa ttacaggatg    420
tagaataact ttgcttattg tgaaatcctc aaaaatgaat gatgcaggca agaagtgcaa    480
attacc                                                               486
```

```
<210> SEQ ID NO 5
<211> LENGTH: 460
<212> TYPE: DNA
<213> ORGANISM: Artificial
<220> FEATURE:
<223> OTHER INFORMATION: RFLP marker TG55, forward sequence

<400> SEQUENCE: 5
tggattcagt gtgaagaaag gggacatggt gagttaccta ccatatgcaa tgggaagaat    60
gaaatttata tggggcgatg atgcagaaga atatacaccg gagagatggc ttgatgggga    120
cggtttcttc aggcaataca atcccttcaa atttacagct ttccagggtg ttttgaagct    180
```

| | |
|---|---|
| catcataagc tttgattatc attttgttaa agccttgaac gcaagtctat acttaacttg | 240 |
| cctagagcta tgtactgtcg acatatgatc aattaactaa gcacattctt ttgttaataa | 300 |
| aacaggcagg gccaaggatt tgcttgggaa aggagtttgc ttataggcaa atgaagatat | 360 |
| tctctgctgt tttattacat cacttcgttt tcaagctgag tgatgacaac aaggctacca | 420 |
| actacaggac aatgattact cttcacattg atgggggatt | 460 |

<210> SEQ ID NO 6
<211> LENGTH: 516
<212> TYPE: DNA
<213> ORGANISM: Artificial
<220> FEATURE:
<223> OTHER INFORMATION: RFLP marker TG55, reverse sequence

<400> SEQUENCE: 6

| | |
|---|---|
| gatccaaaat atgcttttct gatgacccctt accagatgga ttcagtgtga agaaagggga | 60 |
| catggtgagt tacctaccat atgcaatggg aagaatgaaa tttatatggg gtgatgatgc | 120 |
| agaagaatat aaaccggaga gatggcttga tggggacggt ttcttcaggc aagagaatcc | 180 |
| cttcaaattt acagctttcc aggttgtttt aaagctcatc ataagctttg attatcattt | 240 |
| tgttaaagcc ttgaacgcga gtctatactt aacttgccta gtgctatgta ctgtcgtcat | 300 |
| atgatcaatt aactaagcac attcttttgt taataaaaca ggcagggcca aggatttgct | 360 |
| tgggaaagga gtttgcttat aggcaaatga agatattctc tgctgtttta ttacatcact | 420 |
| ttgttttcaa gttgagtgat gacaacaagg ctaccaacta caggacaatg attactcttc | 480 |
| acattgatgg gggattgcat gttcgtgtct ttagta | 516 |

<210> SEQ ID NO 7
<211> LENGTH: 435
<212> TYPE: DNA
<213> ORGANISM: Artificial
<220> FEATURE:
<223> OTHER INFORMATION: RFLP marker TG59, forward sequence

<400> SEQUENCE: 7

| | |
|---|---|
| tcgacctgca gatatttcat aaaagaatgc ccctgaagc agttgatttg gtgtcgaggc | 60 |
| ttctccaata ttctccaact ctacgctgca ctgctgtaag taaaaagttt tcttctcaat | 120 |
| tatcaagtat ttaggatatt ctggtagttt cccattttac ccatcattca aacatggtgt | 180 |
| tccattttg ttatgtttca atatgcgagt tctcattgat tgtccttta gcacttctgt | 240 |
| tttccgggga tattgagaac attttgtgtt tattgacagt tggaagcatg tgcacaccct | 300 |
| ttctttgatt cttaaggga accaaatgct tgcttgccaa atgggcgacc tctgcctccc | 360 |
| ctattcaact tttcacctca aggtgagctt cagtctagct ttctcctttt atttcacatg | 420 |
| atttgatacg tcaat | 435 |

<210> SEQ ID NO 8
<211> LENGTH: 526
<212> TYPE: DNA
<213> ORGANISM: Artificial
<220> FEATURE:
<223> OTHER INFORMATION: RFLP marker TG59, reverse sequence

<400> SEQUENCE: 8

| | |
|---|---|
| agttgggaat tatatcctgt tcagtagaca aattacccaa ccagaatata cgtacctgaa | 60 |
| tgttcatgtg atagataagt ccatactagt acttctgtct tgtgaatatc tgtgtgttgc | 120 |
| cttgtgagta aggatattca ttgctccaat gcaaaaccat tatgtcattg tcttagggag | 180 |

```
ctttctgttg tttgtatggc atgaaaagtt aatcctaaaa gaaaggtaaa gtaaaggtgc    240
atcctaggtt agtataatgt tctgaaggca agatgttttt tcttttgatt taaacttatg    300 ttttttttc tttgattccg tctccttccc taatagcaaa aactgggaag ttgaaactac    360
gttataactg gacaacctca taaatgaaaa agatggtaaa taatgccatt tctggggtgg    420
ggtaattttc cttagatgag tgtgatactg ttgtacctgt tgcttgaact cctaagtttc    480
ctcattttct tccttttgt ttatgctaaa tgccgtgtgt actgtg                    526

<210> SEQ ID NO 9
<211> LENGTH: 430
<212> TYPE: DNA
<213> ORGANISM: Artificial
<220> FEATURE:
<223> OTHER INFORMATION: RFLP marker TG145, forward sequence

<400> SEQUENCE: 9
atgggctatg cttggtgctc ttggatgtgt cttccctgag ctattggccc gtaatggtgt     60
caagttcggt gaggctgtgt ggttcaaggc tggatcccag atcttcagcg agggtggact    120
tgattacttg ggcaacccaa gcttggtcca tgcacaaagc atcttggcca tctgggcttg    180
ccaagttgtg ttgatgggag ccgttgaggg ataccgcatt gctggtggac ctcttggtga    240
ggttgtcgac ccactctacc ccggtggcag cttcgaccca ttaggccttg ctgaagaccc    300
ggaggcattt gctgagctta aggttaagga gatcaagaac ggcagacttg ctatgttctc    360
tatgtttggg ttcttttgttc aggccattgt taccggaaag ggtccattgg agaacctcgc    420
tgaccacctt                                                            430

<210> SEQ ID NO 10
<211> LENGTH: 481
<212> TYPE: DNA
<213> ORGANISM: Artificial
<220> FEATURE:
<223> OTHER INFORMATION: RFLP marker TG145, reverse sequence

<400> SEQUENCE: 10
ggagacaacc ttgcatgcca gcagtggatc acctcgagtc cacggttctt ggcaaaggtt     60
tctggatctg ctgaaagtcc agcggtgtcc cacccgtagt caccagggaa ttcaccattc    120
aagtagctag gggactcacc agagaatgga cccaagtact taacacggtc agggccatac    180
catgggctgc tagatggggc tgactttgcg acagcctttc tcatagtgat ccttccattt    240
cctgtgattt ctgaggcaga tggtaagagt ttcactgctt gtccagcaaa agaagggaa     300 gaaagagcca ttgtagcagc tgccatggtg tttatatcaa gagaaatgta agtgtttgat    360
ggtatgagat attgttgaag ttggctgtaa tgagatgaag ttacaaggaa ttaattcacc    420
atatatatag ggagtaatta agagggaaag agtccaaatt atctaatgat atctatatct    480
a                                                                    481

<210> SEQ ID NO 11
<211> LENGTH: 479
<212> TYPE: DNA
<213> ORGANISM: Artificial
<220> FEATURE:
<223> OTHER INFORMATION: RFLP marker CT128, forward sequence

<400> SEQUENCE: 11
cttttttttt tttcaacac aaacaaaatt tcattatatt gtcaggtagc acactacatc      60
tttacactgt catcaaacga ccagagactt gagaacgttt taagagattc attttccggg    120
```

```
gacaaagttt gtggcgaaag cccaggcatt gttgtttacg gggtctgcaa ggtggtcagc    180
aaggttctcc aatggaccct ttccggtgac aatagcttga acaaagaatc caaacataga    240
gaacatagca agtctaccgt tcttgatctc ctttaccttg agctcagcaa atgcctctgg    300
gtcttcagca aggcctaatg ggtcgaagct gccaccaggg tagagtgggt cgacaacctc    360
accaagaggt ccaccagcaa tacggtatcc ctcaacagct cccatcaaca caacttggca    420
agcccagatg gccaagatgc tttgtgcatg gaccaagctt gggttgccca agtagtcaa     479

<210> SEQ ID NO 12
<211> LENGTH: 495
<212> TYPE: DNA
<213> ORGANISM: Artificial
<220> FEATURE:
<223> OTHER INFORMATION: RFLP marker CT128, reverse sequence

<400> SEQUENCE: 12
ctggtgatta cgggtgggat accgctggac tttcagcaga ccctgaaact tttgccaaga     60
accgtgaact tgaggtgatc cactgcagat gggctatgct tggtgctctt ggatgtgtct    120
tccctgagct cttggcccgt aatggtgtca agttcggtga ggctgtgtgg ttcaaggccg    180
gatcccagat cttcagtgaa ggtggacttg actacttggg caacccaagc ttggtccatg    240
cacaaagcat cttggccatc tgggcttgcc aagttgtgtt gatgggagct gttgagggat    300
accgtattgc tggtgggacc tcttggtgag gttgtcgacc cactctaccc tggtggcagc    360
ttcgacccat taggccttgc tgaagaccca gaggcatttg ctgagctcaa ggtaaaggag    420
atcaagaacg gtagacttgc tatgttctct atgtttggat tctttgttca agctattgtc    480
accggaaagg gtcca                                                     495

<210> SEQ ID NO 13
<211> LENGTH: 24
<212> TYPE: DNA
<213> ORGANISM: Artificial
<220> FEATURE:
<223> OTHER INFORMATION: Forward primer

<400> SEQUENCE: 13
atcatacctt ctctctccaa accc                                            24

<210> SEQ ID NO 14
<211> LENGTH: 23
<212> TYPE: DNA
<213> ORGANISM: Artificial
<220> FEATURE:
<223> OTHER INFORMATION: Reverse primer

<400> SEQUENCE: 14
tcgccattgc tcactttaaa ctg                                             23

<210> SEQ ID NO 15
<211> LENGTH: 20
<212> TYPE: DNA
<213> ORGANISM: Artificial
<220> FEATURE:
<223> OTHER INFORMATION: Forward primer

<400> SEQUENCE: 15
ttgggcgacc acgctgaatc                                                 20

<210> SEQ ID NO 16
<211> LENGTH: 22
```

```
<212> TYPE: DNA
<213> ORGANISM: Artificial
<220> FEATURE:
<223> OTHER INFORMATION: Reverse primer

<400> SEQUENCE: 16
ttacccacat caggaccttg cc                                                  22

<210> SEQ ID NO 17
<211> LENGTH: 25
<212> TYPE: DNA
<213> ORGANISM: Artificial
<220> FEATURE:
<223> OTHER INFORMATION: Forward primer

<400> SEQUENCE: 17
tgataaatgc tgggaagatt gactc                                               25

<210> SEQ ID NO 18
<211> LENGTH: 26
<212> TYPE: DNA
<213> ORGANISM: Artificial
<220> FEATURE:
<223> OTHER INFORMATION: Reverse primer

<400> SEQUENCE: 18
atcaacctgg ctccatcttc tatttg                                              26

<210> SEQ ID NO 19
<211> LENGTH: 528
<212> TYPE: DNA
<213> ORGANISM: Artificial
<220> FEATURE:
<223> OTHER INFORMATION: RFLP marker TG609, forward sequence

<400> SEQUENCE: 19
gagacagctt gcatgcctgc agaggtgata aattcaccaa ggtttcatat ttaggaaaca          60
agaaaattaa aagatcatta acacagatga aaggatatga ctaggaggca atgactgatc        120
tttgactatc aaatacttct cagggaaaca atgtgaatgg gcttttacat gcagagatat        180
tgattgtgat catgttgaag aacttaggaa acatgaaatt aaatgatcat taacactgat        240
gcaaggatat gccaagtagg caagcaaatt aaggttgaac ataaatgtct gtgatctttg        300
actatcaaat atcttctcag aaaaaaaaat gtgaatgctc atttacatgc agagatggct        360
attgtgatca tgtggctcag ccttgagtct atattgaggt gcagacaaca tagtccctaa        420
ccacatgtgt gatcaagcaa cttttttgat gtccacaggg ttataagtag gcaacattta        480
agcaagaaaa aacacaggat cactattgag tcagctgctg ttgcctgt                     528

<210> SEQ ID NO 20
<211> LENGTH: 537
<212> TYPE: DNA
<213> ORGANISM: Artificial
<220> FEATURE:
<223> OTHER INFORMATION: RFLP marker TG609, reverse sequence

<400> SEQUENCE: 20
ggagacaagc ttgcatgcct gcagaggtga taaattcacc aaggtttcat atttaggaaa         60
caagaaaatt aaaagatcat taacacagat gaaaggatat gactagtagg caatgactga       120
tctttgacta tcaaatactt ctcagggaaa caatgtgaat gggcttttac atgcagagat       180
attgattgtg atcatgttga agaacttagg aaacatgaaa ttaaatgatc attaacactg       240
atgcaaggat atgccaagta ggcaagcaaa ttaaggttga acataaatgt ctgtgatctt       300
```

```
tgactatcaa atatcttctc agaaaaaaaa atgtgaatgc tcatttacat gcagagatgg    360
ctattgtgat catgtggctc agccttgagt ctatattgag gtgcagacaa catagtccct    420
aaccacatgt gtgatcaagc aacttttttg atgtccacag gtttataagt aggcaacatt    480
taagcaagaa aaaacacagg atcactattg agtcagctgc tgttgcctgt tactgag       537

<210> SEQ ID NO 21
<211> LENGTH: 517
<212> TYPE: DNA
<213> ORGANISM: Artificial
<220> FEATURE:
<223> OTHER INFORMATION: RFLP marker TG62, forward sequence

<400> SEQUENCE: 21
caaaatgctt cagctactgg ctaaatgaag tatgttctca acatattcac aagcttctgt     60
cttcgaagct caagaagtgt cggtattatc tgaattaaat agtaaagcaa agagatggtt    120
ttatgtttct taagcagcat ttcttagctt aacggccctc cagatatatg gtggacaaaa    180
tagaatccat tagatataac aaatgggatt agtataatga tcttttactt tgttagatga    240
tcatactaac agattgcaag ttaatcatat ccaacatatt ctgtagatat ttcacattgg    300
ctagcatgag gaaaggtcat gtaggaaatt gaatagagtt caattttggg aaaagttgca    360
ttgaagaagg taacttcaac aaacgtgtga aaaaatcaca tttgagttgc ccgctcacca    420
tcgtgattcc agtacgaact actcaaaaat ttacttttga gccttaaaca tcattttaag    480
ccttgaaaag ctgcttttga aaagatctaa gcaagat                              517

<210> SEQ ID NO 22
<211> LENGTH: 537
<212> TYPE: DNA
<213> ORGANISM: Artificial
<220> FEATURE:
<223> OTHER INFORMATION: RFLP marker TG62, reverse sequence

<400> SEQUENCE: 22
ggagaatatt gtcactctat cagatagttc aaaactatcg gagaatgaaa tggtcaattc     60
ttctcacaag atattcatgc ctagttgcag tgtccgaatt aacataacat gctcaatttt    120
catatcttgc agcaaaattt atcattgaaa ctctctgaga tggaaacaga gaacaaagac    180
catattggaa agcttcaatc agacatgcag aaaaggaag atgagattca tgttttacgc    240
aaggaaattg acaattacac ggaaacagtg gattcactgg agaagcatgt tacagagatt    300
aacaataaat tggaggagaa agatcagctt gttcaggaac ttcaggacaa ggagaagcag    360
ttggaagctg acagagaaaa ggttttttact acggatactt ttagttctac aaattctatt    420
ataaccaata caatgtgttc aagtgactag tgttttgcac cttgttgcag attcaggcat    480
ctttgcttgc tgctgaaagc aagctcacag aatccaaaaa gcagtatgat cagatgt       537

<210> SEQ ID NO 23
<211> LENGTH: 478
<212> TYPE: DNA
<213> ORGANISM: Artificial
<220> FEATURE:
<223> OTHER INFORMATION: RFLP marker TG555, forward sequence

<400> SEQUENCE: 23
aattcggagc tcactgcttc taatcctcag tgagacttat tttctacata ttaaacaata     60
agaaatttac gaaggaatat tatagactga attccttggt gacaagtatc aagacatctt    120
gaccaagttt aaagttttgt agtggcagtt cttttaagct ttacttgtgt gaggtagaca    180
```

```
tcaaggaaga taagtagcag ctactcttca cggagcagcc cataggacac tcaaattcac    240
tattgcgagg gtcaatctac caatttatgg aacgatacca gtaaagtcat ttttatgtaa    300
acatcagaca gcttttgact aagcagagac atgaataagt tctatttgtt agaagtcgaa    360
gagacaaata agttaatttc acctatgcta taaaagagga ctcttatagt tataaataca    420 gtacattta ttaagggttc taattgttga ctatgatagc aagcatgccg tactaatt      478

<210> SEQ ID NO 24
<211> LENGTH: 503
<212> TYPE: DNA
<213> ORGANISM: Artificial
<220> FEATURE:
<223> OTHER INFORMATION: RFLP marker TG555, reverse sequence

<400> SEQUENCE: 24
acattttgag gaagacagga gttatgtatc gccatctggt gtgctccaag aacatgacag    60
atataaaaga ccgcggggtg caccagagaa atgttgcatt ggagcatatt gaacatcata   120
ggctcaatgg aattgtttac tttgcagatg atgataatat ctactcactt gagttgtttg   180
agagcattag atcgatcaag taagttgaga ttcatcagtc ttgtttacat gacttgtctt   240
tgttttgtcc tgctgtgagc atgttcagga tgatgttatg tgctttatgt agatgttcaa   300
gtcgataata gtgaatagtc tagagctatt tcacatatat acaacttca ctaacaaatt    360 cttttcctgg tgtcctcggt tcatcactct tcatagttat aagaataaca gttgtagatt   420
agaccactgg tcgtgtgatt tttggactta attattatct caattcttcc tcaaaatagc   480
agtccttaga ttagaagctg agg                                           503

<210> SEQ ID NO 25
<211> LENGTH: 454
<212> TYPE: DNA
<213> ORGANISM: Artificial
<220> FEATURE:
<223> OTHER INFORMATION: RFLP marker CT50, forward sequence

<400> SEQUENCE: 25 ctttttttt ttttttatat attgtggtat agattattat ataataacaa ggtgaattaa    60
catgagaaat gaataattgt cacattcttg ttctgtccat tttccagtag cggctagttg   120
gaaaatttgt tgtaacatgt aacacaggct gtccacattc tactccagag agaaagttgg   180
taagtagtgg gggcaaaaga tagagacccc aatagctatc aattcacttt gttgacaatc   240
aagatttgag aaaaaagatc aaaactttac caacttagat agctccataa tcaactgtag   300
gtacaattct ttagtgaaat tgcggcgttc atcttctggg gacgaagagt aagtagacaa   360
tcaattgtct tgtagaactt gggctttacc attttcccta ggacataagc tcttgatcga   420
agcttgaagt ttaattttag tggcactggt aatg                               454

<210> SEQ ID NO 26
<211> LENGTH: 496
<212> TYPE: DNA
<213> ORGANISM: Artificial
<220> FEATURE:
<223> OTHER INFORMATION: RFLP marker CT50, reverse sequence

<400> SEQUENCE: 26
tttttttttt tttttagcca aaatgcatac aaaaactgat tcagaagata cgagcttggc    60
tccttcgtcg ccggacaata gagggccgac ggcgtattac gttcagagtc cgtcacgtga   120
ttctcacgat ggcgagaaga caacgacgtc gtttcactct actcctgtta tcagtcccat   180
```

```
gggttctcct cctcactctc actcatccgt cggccgtcac tcccgtgatt cctcttcctc    240
cagattctcc ggctccctca agcctggatc tcagaagatt ttacccgacg ccgccggagg    300
cgtcggcggc cgtcaccacc gcaaagggca gaagccctgg aaggaatgtg atgttatttg    360
aggaagaagg actacttgaa gatgatagat ccagtaaatc tcttccacgt cgttgctatg    420
tccttgcttt tgttgttgg tttcttcgtc cttttctcct tctttgctct catcctttgg    480
ggtgctagtc gacctc                                                    496
```

<210> SEQ ID NO 27
<211> LENGTH: 26
<212> TYPE: DNA
<213> ORGANISM: Artificial
<220> FEATURE:
<223> OTHER INFORMATION: Forward primer

<400> SEQUENCE: 27

```
tcatcatcaa ctatcgtgat gctaag                                          26
```

<210> SEQ ID NO 28
<211> LENGTH: 23
<212> TYPE: DNA
<213> ORGANISM: Artificial
<220> FEATURE:
<223> OTHER INFORMATION: Reverse primer

<400> SEQUENCE: 28

```
acgcttgcga gccttcttga gac                                             23
```

<210> SEQ ID NO 29
<211> LENGTH: 500
<212> TYPE: DNA
<213> ORGANISM: Artificial
<220> FEATURE:
<223> OTHER INFORMATION: RFLP marker TG599, forward sequence

<400> SEQUENCE: 29

```
tgctttgaga cagatgtctc tcattaagtg actgaagctt tcttctagtt ggctagcata     60
ttcattttca gcatataatc tgtatcatga acaaaattgc gacagtattg aatttttatt    120
gttgaatagt cttttattta tccccgaagt tgagggtgga acttacattt tctgttgatc    180
cttgcttgct gttttgtaa acaaaaaagc gtcacccatt attttctttt tattctttct    240
aggttgggac taagattttt tgaaatgaga aaggtattcg ctaccttgag ggctgtggtt    300
gaagtgatgg agtatctgag caaagatgca gctcctgatg gtgtgggaag gcttataaag    360
gaggagggag tatttccttt catttctttg tatttccgtg tgtgtatagt ccggaactgg    420
ttccctactt atgaattctt tcatggtttg gtcaattgag aaggatcaag aaatctgatg    480
ctactttatc atgggaactt                                                500
```

<210> SEQ ID NO 30
<211> LENGTH: 525
<212> TYPE: DNA
<213> ORGANISM: Artificial
<220> FEATURE:
<223> OTHER INFORMATION: RFLP marker TG599, reverse sequence

<400> SEQUENCE: 30

```
gcttgcatgc ctgcagagtg gtcatacaat aaaaggtaaa aatcaacatt cttacctctg     60
gaaagaaacc aatagcattg gtcaatgatg ctgcctctag aggaacaata ttgtatggtg    120
caagttcccc tgataaagta gcatcagatt tcttgatcct tctcaactga ccaaaccatg    180
```

-continued

```
aaagaattca taagtaggga accagttccg gactatacac acacggaaat acaaagaaat    240
gaaaggaaat actacctcct cctttataag ccttcccaca ccatcaggag ctgcatcttt    300
gctcagatac tccatcactt caaccacagc cctcaaggta gcgaatacct ttctcatttc    360
aaaaaatctt agtcccaacc tagaaagaat aaaagaaaaa taatgggtga cgcttttttg    420
tttacaaaaa cagcaagcaa ggatcaacag aaaatctaag ttccaccctc aacttcgggg    480
ataataaaaa gactattcaa caataaaaat tcaatactgt cgcaa                    525
```

<210> SEQ ID NO 31
<211> LENGTH: 456
<212> TYPE: DNA
<213> ORGANISM: Artificial
<220> FEATURE:
<223> OTHER INFORMATION: RFLP marker TG10, forward sequence

<400> SEQUENCE: 31

```
aactctgctc tgccaatagt agtcaggcag atcaagatgc tcaaaatttt ctatttgaat     60
tggaagcatc aagatggttc ttagcattta ttttagaaag actaaccata ttatcaaata    120
accagactga gacgcacaca aaagtttccc tctattattt ttataatgat gtgaagatgc    180
tacataatga gtacactttg ccttacttta ctgcagatgg acctaccagg cccaaacgga    240
catgtagcta tgcagaagaa gcaaccgcta tgaatgtctc aaactgttgg cctaggcgat    300
cagcacagat gatgaatctg gaagtacatt ccaagaagga agctggagc gtgggaacta     360 accagatgca ggggatgaat ccacaccttt cagttgatca tctgaaggga aaactaagaa    420
ttttcatgag aaaatgactg gctattttca actttg                              456
```

<210> SEQ ID NO 32
<211> LENGTH: 562
<212> TYPE: DNA
<213> ORGANISM: Artificial
<220> FEATURE:
<223> OTHER INFORMATION: RFLP marker TG10, reverse sequence

<400> SEQUENCE: 32

```
ttcaatgcat ttaagctcaa aaaacaaag ctgtaggaag gagcatatta gtagcctaac      60
tctgctctgc caataatagt taagcagatc aagatgctca aattttcta attgaattgt     120 tagcatcaag atgcttctta gcatttattt tagaaagatt aaccatatta tcaaataacc    180
agacagagac gcacacaaaa gtttcaatct attattttta taatgatgtg aaaatgctac    240
ataatgagta ctttccct tactttactg cagatggacc taccaggccc aaacggtcat     300
gtagttatga cagaagaaca acagtatgaa tttctcaaac tgttggccaa ggtgatcagc    360
aaagattatg aatttggaag tacattccaa gaggaaagct ggagcatcgt aactaaccag    420
atgcagggga tgaatccaca cctttcagtt gatcatctga aggcaaaact aagaattttc    480
atgagaaaat actggttatt ttcaactttg ttggccagac gaggagtcca atgggataga    540
aggactaact caatgacgta tg                                             562
```

<210> SEQ ID NO 33
<211> LENGTH: 422
<212> TYPE: DNA
<213> ORGANISM: Artificial
<220> FEATURE:
<223> OTHER INFORMATION: TM marker TM2A
<220> FEATURE:
<221> NAME/KEY: misc_feature
<222> LOCATION: (2)..(2)
<223> OTHER INFORMATION: n is unknown

```
<220> FEATURE:
<221> NAME/KEY: misc_feature
<222> LOCATION: (10)..(12)
<223> OTHER INFORMATION: n is unknown

<400> SEQUENCE: 33
cnagctcgan nnaccctcac taaagggaac aaaagctgga gctccaccgc ggtggcggcc      60
gctctagaac tagtggatcc cccgggctgc aggctcctcc attgaaaagg gaatcaagtt    120
tgccaaagaa aactaaaaaa acaaaattat ggtctagttt tctatagtga cagttttgga    180 tcttttttggg tcaattgttt ttgtatcctt gcaagtttc ttgcagccgg aggcttagat    240
ttagctcttt tgatattata cccaacattt ctacaaaata atgtatggca aactgggggc    300
ctatcccatt tgccttagtg tggaggtgtt attctcacat gaatcgtttt ccaattatgg    360
ttagtagcag acaattgatg caaaatgaag aaatgttcat gaccaaaaaa aaaaaaaaaa    420
aa                                                                   422

<210> SEQ ID NO 34
<211> LENGTH: 458
<212> TYPE: DNA
<213> ORGANISM: Artificial
<220> FEATURE:
<223> OTHER INFORMATION: RFLP marker TG551, forward sequence

<400> SEQUENCE: 34
aatgaagttc agttgataag ctaaatggtg gaaatactaa ttttaattga cagtaacttt      60
gcatttcaag gtccatacca aaacatttgc taacaccagt tgctttgtca acgaaaacct    120
tggcactcaa aaccctacca aaaggctgaa atgcatttgc aagctcttga tcaccaaatt    180
cttgaggaat atggtaaata aatagattag caccaggtgg acctgtaaac agcaaaatcg    240
tttttgataa gtacaggttt atttctacat gttcaactac cactgccaag tacactagtt    300
caagtgacat ctccaccact taattgcata aagctttacc aacgacaaat ataacaaact    360
tgtgcaagta atttgagttc ctgtctatac agtccagaat ctccatatgc tgctcatctc    420
acaatgttgg ttaaggaaat tgtcaagta aagttcaa                              458

<210> SEQ ID NO 35
<211> LENGTH: 382
<212> TYPE: DNA
<213> ORGANISM: Artificial
<220> FEATURE:
<223> OTHER INFORMATION: RFLP marker TG551, reverse sequence

<400> SEQUENCE: 35
catcttcaag tgtcagctca agtacagggg gtcaggttga aggttgttga acatttattt      60
tgtgaccttt ttagctctag aatttctgta gctaatcaag tacagtccca taacctaggg    120
gctgttaggg ttttctgctg aatgaggctg cttgtcttta ttttggttaa ttattttctg    180
gaaattgttc ctcgtcatag agaatagaag tagaagaaga agaagatagt ataatctatt    240
atatttgttt tttacttaat ttataaagat tccataaatg catgtgatct ttgatcaatg    300
atatcttata caagtgtatc actagaatct attatatttg gatttactta ttttatatag    360
gatttcataa acgcatgtga tc                                              382
```

TOMATO PLANTS HAVING HIGHER LEVELS OF RESISTANCE TO *BOTRYTIS*

RELATED APPLICATIONS

This application is a continuation of PCT Application Ser. No. PCT/NL2005/000762, designating the United States and filed Oct. 24, 2005; which claims the benefit of the filing date of European Application No. 04077931.6, filed Oct. 25, 2004; both of which are hereby incorporated herein by reference in their entirety for all purposes.

TECHNICAL FIELD

The present invention relates to plant breeding and molecular biology. More specifically, the present invention relates to a method for detecting a quantitative trait locus (QTL) associated with resistance to *Botrytis cinerea* in tomato, to a method of producing a *Botrytis*-resistant tomato plant therewith and to *Botrytis*-resistant tomato plants thus obtained and parts thereof.

BACKGROUND

*Botrytis cinerea* is a necrotrophic pathogenic fungus with an exceptionally wide host range comprising at least 235 possible hosts. Because of its wide host range and because it affects economically important parts of the plant *B. cinerea* is a major problem in many commercially grown crops. Amongst growers, the fungus is commonly referred to as *Botrytis*. The cultivated tomato (predominantly *Lycopersicon esculentum*) is also susceptible to infection by *Botrytis* and the fungus generally affects stem, leaves and fruit of the tomato plant. In heated greenhouses the occurrence of infections by *Botrytis* on stems is particularly common.

*Botrytis* actively kills infected cells, causing soft rot, blights, leaf spot, damping-off and stem cancers. Affected leaves become covered with conidiophores and conidia, and subsequently collapse and wither. The fungus will grow from diseased leaves into the stem and produce dry, light brown lesions a few millimeters to several centimeters in length. Lesions may also form at pruning scars on the stem. The stem lesions may also be covered with a gray mold. In severe cases, the infection girdles the stem and kills the plant. Older, senescent tissue of a tomato plant is usually more susceptible to attack by *Botrytis* than younger tissue.

In order to prevent the development of *Botrytis* in greenhouse grown tomatoes, the temperature and relative humidity must be closely regulated. It is further important to provide water without wetting the leaves. For field grown plants, good drainage and weed control should be employed. Moreover, the nutrient levels of the plants must be kept high. However, these preventive measures cannot fully avert the occurrence of considerable yield loss in case of infection.

Fungicides are available for controlling *Botrytis* in both greenhouse and field grown tomatoes. Examples of some fungicides include Dowicide A® and chlorothalonil, which may also be applied to the tomato fruits after harvest. However, *Botrytis* is known to have developed resistance against several commonly used fungicides. In addition, the use of fungicides is undesired both from an economic and from an environmental perspective. Presently, there is a need for commercial tomato varieties that exhibit resistance to *Botrytis*.

Partial resistance to *Botrytis* has been found in several wild species of *Lycopersicon* (Egashira et al. 2000; Nicot et al. 2002; Urbasch 1986). These plants however do not produce commercial crop tomatoes.

It is known from WO 02/085105 that *L. hirsutum* comprises a genetic region on chromosome 10 of the genome that is involved in partial resistance to *Botrytis*. The introgression of this genetic material into cultivated tomato varieties is believed to be capable of providing for cultivated tomato plants that are partially resistant to *Botrytis*.

Thus far, however, breeding programs aimed at providing resistance to *Botrytis* in tomato have had limited success. The reason for these poor results is at present not clear. For one part, this may be due to insufficient knowledge on the genetic basis and inheritance of *Botrytis*-resistance. For another part, this may be due to the lack of proper bioassays for assessing *Botrytis*-resistance levels in tomato plants obtained in breeding programs. The lack of knowledge and methods also complicates the selection of plants among both wild accessions and offspring plants that comprise genes involved in resistance to *Botrytis*.

It is an aim of the present invention to improve the success of breeding programs aimed at providing commercial tomato varieties that are resistant to *Botrytis*. It is a further aim of the present invention to provide for additional and/or improved resistance to *Botrytis* in commercial tomato varieties. It is yet another aim of the present invention to provide for a method for finding additional wild *Lycopersicon* accessions as sources of resistance to *Botrytis* and for finding additional genetic material in the genome of such plants that is involved in resistance of tomato to *Botrytis*. Such additional sources and additional genetic material may be used to broaden the basis for the production of *Botrytis*-resistant varieties of cultivated tomato.

SUMMARY

The present inventors have now found that a particular quantitative bioassay which comprises the measurement of initial and/or progressive parameters of infection with *Botrytis* in tomato plants in combination with a molecular marker detection technique provides for a very advantageous method of detecting sources of resistance to *Botrytis* amongst wild *Lycopersicon* accessions and for detecting genetic material in the genome of such plants that is involved in improved resistance of tomato to *Botrytis*.

By using this combination of techniques, the present inventors have successfully identified partial resistance to *Botrytis* in two lines of wild relatives of tomato, i.e. *Lycopersicon hirsutum* LYC 4/78 and *Lycopersicon parviflorum* G1.1601.

The inventors were subsequently able to produce *Botrytis*-resistant tomato plants by crossing plants from these *Botrytis*-resistant wild (donor) tomato lines with non-resistant recipient tomato plants. These plants exhibited a higher level of resistance than plants comprising a genomic region on chromosome 10 of *L. hirsutum* associated with Botrytis resistance as disclosed in WO 02/085105.

By assessing the resistance level to *Botrytis* in segregating populations ($F_2$ populations) of these newly produced crosses in relation to the presence of molecular markers of the donor plant, the present inventors were able to identify multiple quantitative trait loci (QTLs) linked to *Botrytis*-resistance in the resistant wild tomato lines and thereby establish the location of multiple resistance-conferring DNA sequences in the genome. As a result, the present inventors have now found that *Botrytis* resistance in tomato is inherited polygenically, which may partly explain the poor breeding results. This finding now provides for the improvement of methods of producing *Botrytis*-resistant tomato plants. In the description below, a quantitative trait locus (QTL) associated with resistance to *Botrytis* in tomato will be addressed in short as a QTL for *Botrytis*-resistance or a QTL associated with *Botrytis*-resistance.

A total of six new QTLs for *Botrytis*-resistance were found in the two wild tomato lines. Four of these six QTLs could be linked to a quantitative parameter that reflected the capability of the plant to reduce the initial establishment of an infection, hereinafter referred to as the parameter for disease incidence. Two of these six QTLs could be linked to a quantitative parameter that reflected the capability of the plant to slow the progression of infection, hereinafter referred to as the parameter for lesion growth rate.

By producing genetic linkage maps, it was found that chromosome 1 of *L. hirsutum* LYC 4/78 harbors a QTL that is linked to a reduced rate of growth of lesions induced by *Botrytis* infection and that both chromosomes 2 and 4 of that same accession harbor a QTL that is linked to a reduced disease incidence. In *L. parviflorum* G1.1601, a QTL for reduced rate of lesion growth was found to be located on chromosome 9, while two separate QTLs for reduced disease incidence were found to be located on chromosomes 3 and 4. A QTL on chromosome 10, as reported in the prior art, could not be detected by this method. By using the above-mentioned quantitative bioassay all QTLs in *L. hirsutum* LYC 4/78 tested thus far could be confirmed by assessing disease resistance in $BC_2S_1$ (backcross 2, selfed) progenies segregating for the QTLs under investigation.

The present invention relates in a first aspect to a *Botrytis*-resistant tomato plant, wherein said plant has a susceptibility to *Botrytis cinerea* which is at least 3 times lower than a susceptible control plant when measured by a bioassay wherein the average length of a stem lesion resulting from *Botrytis cinerea* infection in adult plants is measured during a three week period under standard practice conditions. The stem lesion length over a period of three weeks as used herein as a measure for the level of resistance is to be determined by standard practice conditions as described herein. In a preferred embodiment, said *Botrytis*-resistant tomato plant is characterized in that said plant comprises within its genome at least one QTL or a *Botrytis*-resistance-conferring part thereof selected from the group consisting of the QTLs on chromosomes 1, 2 and 4 of *Lycopersicon hirsutum* LYC 4/78 and the QTLs on chromosomes 3, 4 and 9 in *Lycopersicon parviflorum* G1.1601 associated with *Botrytis* resistance, and wherein said QTL or said *Botrytis*-resistance-conferring part thereof is not in its natural genetic background.

The present invention relates in another aspect to a method for detecting a quantitative trait locus (QTL) associated with resistance to *Botrytis* in tomato. The method comprises the steps of crossing a *Botrytis*-resistant donor tomato plant with a non-resistant or partially resistant (*Botrytis*-susceptible) recipient tomato plant; contacting one or more offspring plants with an infective amount of *Botrytis*; quantitatively determining the disease incidence and/or the rate of lesion growth in said one or more offspring plants; establishing a genetic linkage map that links the observed disease incidence and/or the lesion growth rate to the presence of chromosomal markers of said donor tomato plant in said one or more offspring plants; and assigning to a quantitative trait locus the contiguous markers on said map that are linked to a reduced disease incidence and/or a reduced lesion growth rate.

In another aspect, the present invention relates to QTLs obtainable by a method for detecting a QTL for *Botrytis*-resistance according to the invention as outlined above. These QTLs are different from the prior art QTLs. For one, prior art QTLs could not be found. Furthermore, the QTLs of the present invention are more informative than those of the prior art as they are indicative of either a characteristic relating to the plant's ability to oppose the onset of the disease, or a characteristic relating to the plant's ability to slow the progress of the disease. Such information is highly valuable in breeding programs, since combinations thereof may suitably provide for improved resistance, and proper inheritance of the resistance trait from one generation to another may be better controlled.

The present invention further relates to a QTL for *Botrytis*-resistance in tomato, wherein said QTL is selected from the group consisting of the QTLs on chromosomes 1, 2 and 4 of *Lycopersicon hirsutum* LYC 4/78 and the QTLs on chromosomes 3, 4 and 9 in *Lycopersicon parviflorum* G1.1601 associated with *Botrytis* resistance. These QTLs are located on positions of the genome not previously associated with resistance to *Botrytis*. Details of these QTLs are described in more detail herein below.

The alleles present on the positions of the genome indicated by these QTLs are an aspect of the present invention.

A QTL of the present invention may be in the form of an isolated, preferably double stranded nucleic acid sequence comprising said QTL or a resistance-conferring part thereof. Very suitably, the size of the nucleic acid sequence, which may for instance be isolated from the chromosome of a suitable donor plant, may represent a genetic distance of 1-100 cM, preferably 10-50 cM on said chromosome. Said nucleic acid may comprise at least 50, more preferably at least 500, even more preferably at least 1000, still more preferably at least 5000 base pairs. One or more nucleic acid sequences comprising a QTL or a resistance-conferring part thereof according to the invention may in turn be comprised in a nucleic acid construct, said construct may further comprise regions that flank said one or more nucleic acid sequences and which regions are capable of being integrated into a suitable vector for transfer of said one or more nucleic acid sequences into a suitable *Botrytis*-susceptible recipient tomato plant. The vector may further comprise suitable promoter regions or other regulatory sequences. The QTLs may also be in a form present within the genome of a tomato plant. The QTLs of the present invention preferably comprise at least one marker, preferably two, more preferably three, still more preferably four, still more preferably more than four markers associated with *Botrytis*-resistance selected from the group consisting of the markers of Tables 1 and 2 and the markers as indicated in FIGS. 1, 5 and 6 linked to said QTL.

The present invention relates in another aspect to a method for detecting a QTL for *Botrytis*-resistance, comprising detecting at least one marker selected from the group consisting of the markers of Tables 1 and 2 and the markers as indicated in FIGS. 1, 5 and 6 linked to a QTL for *Botrytis*-resistance in a suspected *Botrytis*-resistant tomato plant.

The present invention further relates to a method of producing a *Botrytis*-resistant tomato plant. The method comprises the steps of detecting a QTL for *Botrytis*-resistance in a *Botrytis*-resistant donor tomato plant by performing any one of the methods for detecting a quantitative trait locus (QTL) for *Botrytis*-resistance according to the invention, and transferring nucleic acid comprising at least one QTL thus detected, or a *Botrytis*-resistance-conferring part thereof, from said donor plant to a *Botrytis*-susceptible recipient tomato plant.

The transfer of nucleic acid comprising at least one QTL or a *Botrytis*-resistance-conferring part thereof may very suitably be performed by crossing said *Botrytis*-resistant donor tomato plant with a *Botrytis*-susceptible recipient tomato plant to produce offspring plants; and selecting from among the offspring plants a plant that comprises in its genome nucleic acid introgressed from said donor tomato plant, wherein said introgressed nucleic acid comprises at least one QTL for *Botrytis*-resistance according to the invention, or a *Botrytis*-resistance-conferring part thereof. The presence in said introgressed nucleic acid of at least one QTL for *Botrytis*-resistance according to the invention, or a *Botrytis*-resistance-conferring part thereof, may suitably be detected by a method according to the present invention wherein at least one marker selected from the group consisting of the markers of Tables 1 and 2 and the markers as indicated in FIGS. 1, 5 and 6 linked to a QTL for *Botrytis*-resistance is detected.

A preferred selection method therefore comprises marker-assisted selection (MAS) (see e.g. Tanksley et al. 1998) of said introgressed DNA wherein one or more markers associated with said QTL are detected in offspring plants. MAS may for instance be performed by isolating genetic material from said offspring plants and determining the presence therein, by molecular techniques, of one or more donor plant markers. Alternatively, molecular marker detection methods may be used without prior isolation of genetic material. Optionally, in addition to the marker detection, a phenotypic test on *Botrytis* resistance may be performed in order to select suitable plants. A very suitable test therefore is the quantitative bioassay as described herein, whereby such parameters as disease incidence and/or rate of lesion growth are determined. The confirmation of the presence of at least one marker from a QTL for *Botrytis*-resistance in combination with the establishment of the presence of a resistant phenotype provides evidence for the successful transfer of nucleic acid comprising at least one QTL, or a *Botrytis*-resistance-conferring part thereof, from the donor plant to the recipient plant.

In an alternative embodiment of a method of producing a *Botrytis*-resistant tomato plant, the indicated transfer of nucleic acid may very suitably be performed by transgenic methods (e.g. by transformation), by protoplast fusion, by a doubled haploid technique or by embryo rescue.

In a preferred embodiment of a method of producing a *Botrytis*-resistant tomato plant, the donor plants are *Lycopersicon hirsutum* LYC 4/78 and/or *Lycopersicon parviflorum* G1.1601 and the nucleic acid transferred from these donor plants into recipient plants preferably comprises at least one QTL for *Botrytis*-resistance selected from the group consisting of the QTLs on chromosomes 1 (QTL-1h), 2 (QTL-2h) and 4 (QTL-4h) of *Lycopersicon hirsutum* LYC 4/78 and the QTLs on chromosomes 3 (QTL-3p), 4 (QTL-4p) and 9 (QTL-9p) in *Lycopersicon parviflorum* G1.1601 associated with *Botrytis* resistance, or a *Botrytis*-resistance-conferring part thereof.

In another preferred embodiment of a method of producing a *Botrytis*-resistant tomato plant, the method comprises the crossing of said *Botrytis*-resistant donor tomato plant with a *Botrytis*-susceptible recipient tomato plant to produce first generation offspring plants; selecting from among the first generation offspring plants a plant that comprises in its genome nucleic acid introgressed from said donor tomato plant, wherein said introgressed nucleic acid comprises at least one QTL, preferably two, more preferably more than two QTLs for *Botrytis*-resistance according to the invention, or a *Botrytis*-resistance-conferring part thereof; crossing said selected offspring plant with a suitable commercial tomato line to produce second generation offspring plants; selecting from among the second generation offspring plants a plant that comprises in its genome nucleic acid introgressed from said first generation offspring tomato plant, wherein said introgressed nucleic acid comprises at least one QTL, preferably two, more preferably more than two QTLs for *Botrytis*-resistance according to the invention, or a *Botrytis*-resistance-conferring part thereof, and optionally producing further generations of offspring plants. The mentioned preferably two, more preferably more than two QTLs for *Botrytis*-resistance that are introgressed in offspring plants may be QTLs for disease incidence, QTLs for lesion growth rate or a combination of these types.

In another aspect, the present invention relates to a *Botrytis*-resistant tomato plant, or part thereof, obtainable by a method of the present invention.

In a still further aspect, the present invention relates to a *Botrytis*-resistant tomato plant, or part thereof, comprising within its genome at least one QTL, or a *Botrytis*-resistance-conferring part thereof, wherein said QTL is selected from the group consisting of the QTLs on chromosomes 1, 2 and 4 of *Lycopersicon hirsutum* LYC 4/78 and the QTLs on chromosomes 3, 4 and 9 in *Lycopersicon parviflorum* G1.1601 associated with Botrytis resistance, and wherein said QTL or said *Botrytis*-resistance-conferring part thereof is not in its natural genetic background.

In yet another aspect, the present invention relates to a method of producing a *Botrytis*-resistant inbred tomato plant. The method comprises the steps of producing a *Botrytis*-resistant tomato plant according to a method of the invention, selfing said plant, growing seed obtained from said selfed plant into new plants; identifying plants that exhibit *Botrytis* resistance and possess commercially desirable characteristics from amongst said new plants, and repeating the steps of selfing and selection until an inbred tomato plant is produced which exhibits *Botrytis* resistance and possesses commercially desirable characteristics.

A method of producing a *Botrytis*-resistant inbred tomato plant may further comprise the additional step of selecting homozygote inbred tomato plants that exhibit *Botrytis* resistance and possess commercially desirable characteristics.

In a further aspect, the present invention relates to a *Botrytis*-resistant inbred tomato plant, or parts thereof, obtainable by a method of the invention.

In a further aspect, the present invention relates to a hybrid tomato plant, or parts thereof, that exhibits resistance to *Botrytis*, wherein said hybrid tomato plant is obtainable by crossing a *Botrytis*-resistant inbred tomato plant obtainable by a method of the invention with an inbred tomato plant that exhibits commercially desirable characteristics.

The invention further relates to a tissue culture of regenerable cells of the tomato plants of the present invention. In a preferred embodiment of such a tissue culture, the cells or protoplasts of said cells having been isolated from a tissue selected from the group consisting of leaves, pollen, embryos, roots, root tips, anthers, flowers, fruits, and stems and seeds.

The invention further relates to the use of a marker selected from the group consisting of the markers of Tables 1 and 2 and the markers as indicated in FIGS. 1, 5 and 6, for the detection of QTLs for *Botrytis*-resistance according to the invention, and/or for the detection of *Botrytis*-resistant tomato plants.

The *Botrytis*-resistant donor tomato plant used in methods of the present invention is preferably selected from the group consisting of *Lycopersicon cerasiforme, Lycopersicon cheesmanii, Lycopersicon chilense, Lycopersicon chmielewskii, Lycopersicon esculentum, Lycopersicon hirsutum, Lycopersicon parviflorum, Lycopersicon pennellii, Lycopersicon peruvianum, Lycopersicon pimpinellifolium* and *Solanum lycopersicoides*, more preferably, a wild *Lycopersicon* accession is used as the donor plant. Highly preferred donor plants are *Lycopersicon hirsutum* and *Lycopersicon parviflorum*, in particular *Lycopersicon hirsutum* LYC 4/78 and *Lycopersicon parviflorum* G1.1601.

The *Botrytis*-susceptible recipient tomato plant used in methods of the present invention is preferably a plant of the species *Lycopersicon esculentum*, more preferably an *L. esculentum* cultivar that possess commercially desirable characteristics, or another commercial tomato line.

DETAILED DESCRIPTION OF THE INVENTION

Definitions

Figure 1:
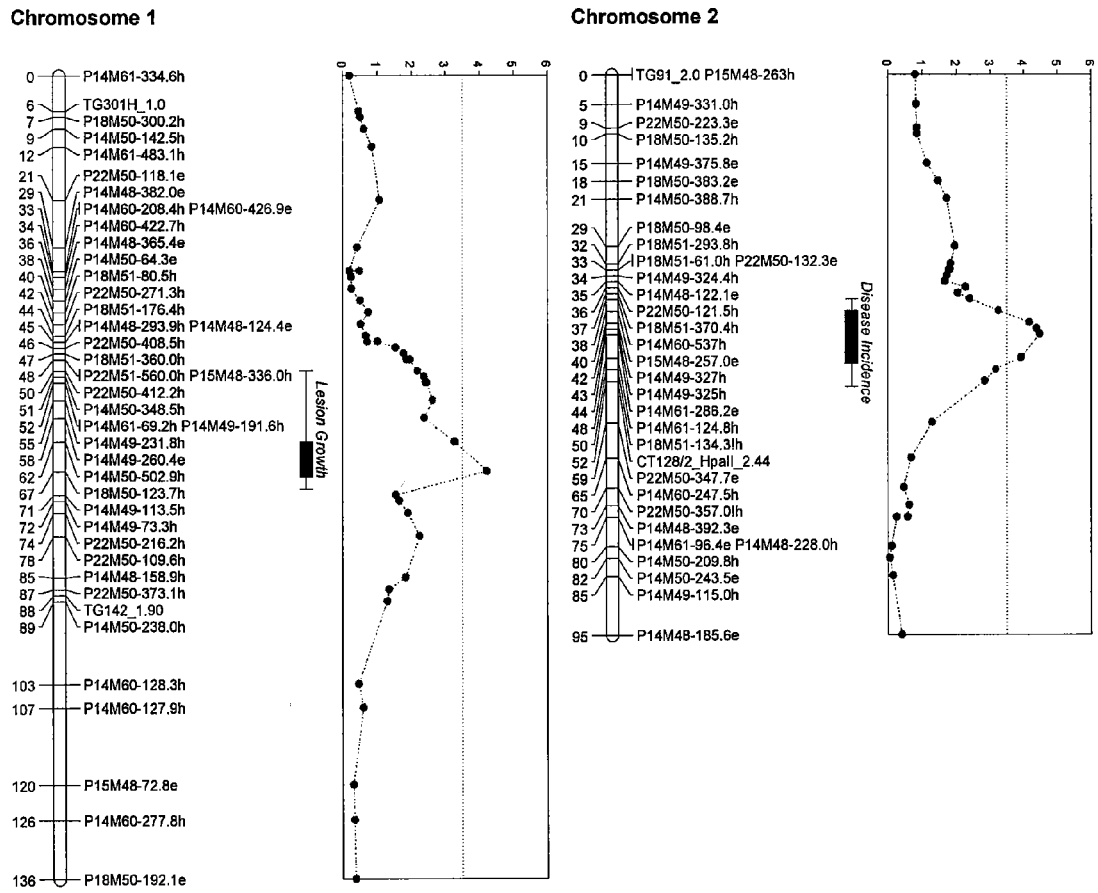
FIG. 1 shows the position of quantitative trait loci (QTLs) for resistance to *B. cinerea* originating from *L. hirsutum* LYC 4/78 with the linkage maps representing chromosome 1 and 2. Map positions are given in cM. The QTL detected on chromosome 1 is for lesion growth and the QTL detected on chromosome 2 is for disease incidence. Bars indicate the QTL intervals. The box shows the LOD 1 interval and the line shows the LOD 2 interval. The codes for AFLP markers are more extensively described in Table 1. All markers indicated as associated to the QTLs may be used as markers in aspects of the present invention.

The headings provided herein are not limitations of the various aspects or embodiments of the invention that can be had by reference to the specification as a whole. Accordingly, the terms defined immediately below are more fully defined by reference to the specification as a whole.

As used herein, the term "*Botrytis*" means *Botrytis cinerea*, also known as gray mold or gray spot, a disease commonly found on the stem, leaves and fruit of tomatoes. It is generally considered that the plant pathogenic fungus *Sclerotinia sclerotiorum* has an infection mechanism similar to that of *B. cinerea* (Prins et al., 2000). Although *S. sclerotiorum*-infection in tomato is economically far less important than *B. cinerea*-infection, both fungi secrete a spectrum of proteases, plant cell wall-degrading enzymes, toxins as well as oxalic acid. Some of these factors are known to play a role in the infection strategy of both fungi. As a result, the mechanisms and genes that confer resistance to *Botrytis* are believed to be equally effective in providing resistance to infection by *S. sclerotiorum*. Therefore, when reference is made herein to "*Botrytis*-resistance," such resistance should be understood as including resistance to any fungus of the family of *Sclerotiniaceae*, preferably resistance to *S. sclerotiorum* and *B. cinerea*, more preferably resistance to *B. cinerea*.

As used herein, the term "allele(s)" means any of one or more alternative forms of a gene, all of which alleles relate to at least one trait or characteristic. In a diploid cell or organism, the two alleles of a given gene occupy corresponding loci on a pair of homologous chromosomes. Since the present invention relates to QTLs, i.e. genomic regions that may comprise one or more genes, but also regulatory sequences, it is in some instances more accurate to refer to "haplotype" (i.e. an allele of a chromosomal segment) in stead of "allele," however, in those instances, the term "allele" should be understood to comprise the term "haplotype."

A "gene" is defined herein as a hereditary unit consisting of a sequence of DNA that occupies a specific location on a chromosome and that contains the genetic instruction for a particular characteristics or trait in an organism.

A "locus" is defined herein as the position that a given gene occupies on a chromosome of a given species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "hybrid" means any offspring of a cross between two genetically unlike individuals, including but not limited to the cross between two inbred lines.

As used herein, the term "inbred" means a substantially homozygous individual or line In this application a "recombination event" is understood to mean a meiotic crossing-over.

As used herein, the terms "introgression," "introgressed" and "introgressing" refer to both a natural and artificial process whereby genes of one species, variety or cultivar are moved into the genome of another species, variety or cultivar, by crossing those species. The process may optionally be completed by backcrossing to the recurrent parent.

"Genetic engineering," "transformation" and "genetic modification" are all used herein as synonyms for the transfer of isolated and cloned genes into the DNA, usually the chromosomal DNA or genome, of another organism.

As used herein, the term "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

The terms "resistant" and "resistance" encompass both partial and full resistance to infection. A *Botrytis*-susceptible tomato plant may either be non-resistant or have low levels of resistance to infection by *Botrytis*.

As used herein, the term "plant part" indicates a part of the tomato plant, including single cells and cell tissues such as plant cells that are intact in plants, cell clumps and tissue cultures from which tomato plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

As used herein, the term "population" means a genetically heterogeneous collection of plants sharing a common genetic derivation.

As used herein, the term "tomato" means any plant, line or population of *Lycopersicon* including but not limited to *Lycopersicon cerasiforme, Lycopersicon cheesmanii, Lycopersicon chilense, Lycopersicon chmielewskii, Lycopersicon esculentum* (or *Solanum lycopersicum*), *Lycopersicon hirsutum, Lycopersicon parviflorum, Lycopersicon pennellii, Lycopersicon peruvianum, Lycopersicon pimpinellifolium*, or *Solanum lycopersicoides*. Although Linnaeus first categorized the modern tomato as a *Solanum*, its scientific name for many years has been *Ly copersicon esculentum*. Similarly, the wild relatives of the modern tomato have been classified within the *Lycopersicon* genus, like *L. pennellii, L. hirsutum, L. peruvianum, L. chilense, L. parviflorum, L. chmielewskii, L. cheesmanii, L. cerasiforme*, and *L. pimpinellifolium*. Over the past few years, there has been debate among tomato researchers and botanists whether to reclassify the names of these species. The newly proposed scientific name for the modern tomato is *Solanum lycopersicum*. Similarly, the names of the wild species may be altered. *L. pennellii* may become *Solanum pennellii, L. hirsutum* may become *S. habrochaites, L. peruvianum* may be split into *S. 'N peruvianum'* and *S. 'Callejon de Huayles,' S. peruvianum,* and *S. corneliomuelleri, L. parviflorum* may become *S. neorickii, L. chmielewskii* may become *S. chmielewskii, L. chilense* may become *S. chilense, L. cheesmaniae* may become *S. cheesmaniae* or *S. galapagense*, and *L. pimpinellifolium* may become *S. pimpinellifolium* (Solanacea Genome Network (2005) Spooner and Knapp; http://www.sgn.cornell.edu/help/about/solanum nomenclature.html).

As used herein, the term "variety" or "cultivar" means a group of similar plants that by structural or genetic features and/or performance can be distinguished from other varieties within the same species.

The term "QTL" is used herein in its art-recognised meaning. The term "QTL associated with resistance to *B. cinerea* in tomato" as well as the shorter term "QTL for *Botrytis*-resistance" refer to a region located on a particular chromosome of tomato that is associated with at least one gene that encodes for *Botrytis*-resistance or at least a regulatory region, i.e. a region of a chromosome that controls the expression of one or more genes involved in *Botrytis*-resistance. The phenotypic expression of that gene may for instance be observed as a reduced rate of lesion growth and/or as a reduced disease incidence. A QTL may for instance comprise one or more genes of which the products confer the genetic resistance. Alternatively, a QTL may for instance comprise regulatory genes or sequences of which the products influence the expression of genes on other loci in the genome of the plant thereby conferring the *Botrytis*-resistance. The QTLs of the present invention may be defined by indicating their genetic location in the genome of the respective wild *Lycopersicon* accession using one or more molecular genomic markers. One or more markers, in turn, indicate a specific locus. Distances between loci are usually measured by frequency of crossing-over between loci on the same chromosome. The farther apart two loci are, the more likely that a crossover will occur between them. Conversely, if two loci are close together, a crossover is less likely to occur between them. As a rule, one centimorgan (cM) is equal to 1% recombination between loci (markers). When a QTL can be indicated by multiple markers the genetic distance between the end-point markers is indicative of the size of the QTL.

The term "*Botrytis*-susceptible recipient tomato plant" is used herein to indicate a tomato plant that is to receive DNA obtained from a donor tomato plant that comprises a QTL for *Botrytis*-resistance. Said "*Botrytis*-susceptible recipient tomato plant" may or may not already comprise one or more QTLs for *Botrytis*-resistance, in which case the term indicates a plant that is to receive an additional QTL.

The term "natural genetic background" is used herein to indicate the original genetic background of a QTL. Such a background may for instance be the genome of a *Botrytis*-resistance wild accession of tomato. For instance, the QTLs of the present invention were found at specific locations on chromosomes 1, 2 and 4 of *Lycopersicon hirsutum* LYC 4/78 and chromosomes 3, 4 and 9 of *Lycopersicon parviflorum* G1.1601. As an example, the *Lycopersicon hirsutum* LYC 4/78 represents the natural genetic background of the QTLs on chromosomes 1, 2 and 4 of *Lycopersicon hirsutum* LYC 4/78. Also the *Lycopersicon hirsutum* LYC 4/78 represent the natural genetic background of said QTLs. Conversely, a method that involves the transfer of DNA comprising the QTL, or a resistance-conferring part thereof, from chromosomes 1 of *Lycopersicon hirsutum* LYC 4/78 to the same position on chromosome 1 of another tomato species, will result in that QTL, or said resistance-conferring part thereof, not being in its natural genetic background.

The term "disease incidence" is defined herein as the parameter that reflects the capability of the plant to reduce the establishment of an infection and may for instance be established by determining the success of achieving infection of the plant upon contact with the infectious agent.

The term "rate of lesion growth" or "lesion growth rate" is defined herein as the parameter that reflects the capability of the plant to slow or reduce the progression of infection, and may for instance be established by determining the rate of growth of expanding lesions.

The term "quantitatively determining" is defined herein as establishing or assessing in a manner involving measurement, in particular the measurement of aspects measurable in terms of amounts and number. Determinations in degrees of severity and indications of greater, more, less, or equal or of increasing or decreasing magnitude, are not comprised in the present term "quantitatively determining," which term ultimately implies the presence of objective counting mechanism for determining absolute values. Therefore "quantitatively determining disease incidence and/or rate of lesion growth"

preferably comprises determining the percentage of all potentially infectious contacts between plant and infectious agent that result in measurable lesions (in order to assess the disease incidence), and/or determining the increase in diameter, circumference, surface area or volume of one or more of said lesions over time under favourable conditions for fungal growth (in order to asses the rate of lesion growth).

The term "standard practice conditions," "standard greenhouse conditions" and "standard conditions" refer to the conditions of light, humidity, temperature, etc. where under plants are grown or incubated, for instance for the purpose of phenotypic characterization of disease resistance, as being standard. For greenhouses for instance, this refers to 16-h day, 15° C.-25° C. More in general, the terms refer to standard and reference growth conditions with a photoperiod of 8 to 24 h (photosynthetic photon flux (PPF) 50 to 1000 µmol m$^{-2}$ s$^{-1}$), preferably a light regime of 16 hours light and 8 hours dark, an air temperature of about 19° C. during the day and 15° C. at night, a water vapour pressure deficit of about 4.4 g m$^{-3}$ corresponding to a relative humidity (RH) of about 60%-85%, at 600-700 ppm $CO_2$ and atmospheric $O_2$ concentration and at atmospheric air pressure (generally 1008 hPa). Water and nutrients may be given drop wise near the stem, or in the form of spray or mist. Standard bioassay experimentation conditions, such as stem lesion length assay, disease incidence and lesion growth rate measurements, are further specified in the Examples below. In more detail, the average stem lesion length assay is to be performed as described in Examples 3.10 and 3.11.

Identification of QTLs Associated with Resistance to *Botrytis* in Tomato

It is known that wild *Lycopersicon* species provide suitable sources for disease and pest resistance traits and the presence of partial resistance to *B. cinerea* in leaves of wild *Lycopersicon* species has been documented (Urbasch, 1986). Two factors have hampered breeding for *B. cinerea* resistance in tomato in the past. Firstly, crossing partial resistance into commercial breeding lines has met with limited success. Secondly, reliable and reproducible disease assays were lacking that would enable the identification and localization of genetic material responsible for conferring resistance.

Urbasch (Urbasch, 1986), for instance, infected leaves with mycelium using agar plugs providing the fungus with an excess of nutrients, which strongly affected the infection process. Other researchers have used subjective plant disease indices, which are unsuitable for quantitative analysis required for the identification of quantitative trait loci (QTLs).

*Botrytis cinerea* infection in *Lycopersicon esculentum* under laboratory conditions is relatively well studied (e.g. Benito et al., 1998). Droplet inoculation of leaves and subsequent incubation at moderate temperatures (15-20° C.) results in a rapid (16-24 h post-infection (hpi)) development of necrotic spots at the site of the inoculum. Infection is temporarily restricted at this point for approximately 48 h. From that moment onwards a proportion of the lesions (usually 5-10%) starts to expand. Outgrowth of these so called "expanding lesions" is accompanied by an increase in fungal biomass and results in colonisation of the complete leaflet in the following 48 h.

The present inventors found that specific QTLs associated with *Botrytis*-resistance in tomato can be identified when a bioassay for measuring resistance is used wherein the rate of the progression of infection and or the success of achieving infection upon contact with the infectious agent are measured quantitatively on parts of the tomato plant, preferably on detached parts, more preferably on stem segments. It was surprisingly found that multiple QTLs for *Botrytis*-resistance were present in the genomes of *Botrytis*-resistant tomato plants, whereas the prior art methods resulted in the tentative identification of only a single QTL for *Botrytis*-resistance. Moreover, the QTLs that were found by using these methods were located on chromosomes not previously associated with *Botrytis*-resistance of tomato plants and the QTLs were associated with various phenotypic manifestations of resistance. Therefore, the methods of the present invention have provided the new insight that the genetic basis of *Botrytis*-resistance in tomato is polygenic.

For instance, it was found that genetic regions present on chromosome 2 and 4 of *L. hirsutum* LYC 4/78 were responsible for a reduced disease incidence, while a genetic region present on chromosome 1 was at least partially responsible for a reduced the rate of lesion growth. Similar genetic regions linked to these phenotypes were found to exist in *L. parviflorum* G1.1601, although these were not necessarily located on the same chromosomes.

It was furthermore discovered that the new QTL regions were associated with higher levels of resistance than that associated with the QTL on chromosome 10 of the prior art. Thus, the method of the present invention is capable of uncovering major QTLs for *Botrytis* resistance that confer a level of resistance to the plant that is higher than previously attained. Thus, one advantage of the method of the present invention is that it results in the discovery of QTLs that are associated with higher levels of resistance to *Botrytis*. This level of resistance may be determined by any method available, such as by using the methods of the present invention or by using conventional methods of the prior art. A detailed description of experimental setup and conditions is provided in the Examples below.

A method for detecting a quantitative trait locus (QTL) associated with resistance to *Botrytis* in tomato according to the present invention, otherwise addressable as method for identifying or locating a quantitative trait locus (QTL), requires the availability of a (partially) *Botrytis*-resistant tomato plant. Such a plant may be provided by any means known in the art, and by using any method for the determination of the presence of said (partial) resistance in said plant. The provision of a (partially) *Botrytis*-resistant tomato plant (which will further serve as a donor plant in a method of the present invention) enables the establishment or provision of chromosomal markers, preferably AFLP, CAPS and/or SCAR markers, most preferably CAPS and/or SCAR markers, for at least one, but preferably for all chromosome of said plant. By establishing a collection of chromosomal markers over the whole length of said chromosomes, the various locations of said chromosomes may effectively be marked. Such methods are well known in the art and exemplary methods will be described in more detail herein below.

A method for detecting a quantitative trait locus (QTL) associated with resistance to *Botrytis* in tomato according to the present invention comprises as a first step the crossing of said (partially) *Botrytis*-resistant donor tomato plant with a non-resistant, or Botrytis susceptible, recipient tomato plant in order to produce offspring plants. Subsequently one or more offspring plants are contacted with an infective amount of *Botrytis*. Such an amount may vary between plants and between fungal species tested. Usually an amount of about 1 to 10 to an amount of about 500-5000 conidia of said fungus will be sufficient.

A subsequent step comprises quantitatively determining the disease incidence and/or the rate of lesion growth in one or more offspring plants produced from said cross. Said quantitative determination is preferably performed in multiple offspring plants. The offspring plants are preferably plants of the $F_2$ population derived from a cross between a *Botrytis*- resistant donor tomato plant and a non-resistant or *Botrytis*-susceptible recipient tomato plant. Preferably, as the offspring, a segregating $F_2$ population is used, more preferably, an $F_2$ population derived from a cross between *L. esculentum* cv. Moneymaker and *L. hirsutum* LYC 4/78. In practice, $F_1$ seed derived from said cross may be grown into $F_1$ plants where after one single $F_1$ plant is then selfed to produce $F_2$ seed of which the subsequently derived $F_2$ plants are used for the determination of the disease incidence and/or the rate of lesion growth in a method of the invention. Alternatively, $F_3$ lines may be used for resistance assays.

The step of contacting one or more offspring plants with an infective amount of *Botrytis* and quantitatively determining the disease incidence and/or the rate of lesion growth in said one or more offspring plants is preferably performed as part of a resistance bioassay on stem segments or leaves as described herein, preferably a resistance bioassay on stem segments. The skilled person will understand that variations to these assays as described herein below are possible.

A resistance bioassay on stem segments may essentially be performed as follows: First, seeds for the offspring plants are planted and grown to seedlings/plants of suitably approximately 50 cm in height. The top 5-10 cm and bottom 5-10 cm of the stem of the plants may be removed and the remaining 30 cm may be cut into equal segments of 5-6 cm. The stem segments are preferably placed upright in a lattice with the stem base on wet filter paper. Prior to inoculation, the stem segments are suitably sprayed with water in order to ensure an equal spread of the inoculum over the wound surface. Each stem segment may then be inoculated by a conidial suspension of *B. cinerea*. A suitable amount of inoculum, for instance one drop of about 5 µl, comprising approximately $10^6$ conidia·ml$^{-1}$, may thereto be applied on the top of each stem segment. The stem segments are then incubated at a temperature of suitably about 16° C., preferably in the dark, and preferably at high humidity (e.g. 100% RH). Infection progress may be determined quantitatively by measuring the maximum advance of rot symptom at various time intervals after inoculation with a Vernier caliper. At a number of suitable time intervals, for instance at 96, 120 and 144 hours post-infection (hpi), the stems may then be inspected for lesion formation (disease incidence) and lesion growth, in a quantitative manner. Very suitable parameters comprise the measurement of the size of the lesion, for instance by using a caliper. In order to correct for variation caused by the season or cultivation of the plants, the quantitative measurements of the bioassays may be related to the comparable measurements in susceptible control or reference lines. The disease incidence may suitably be determined by dividing the total number of expanding lesions by the total number of inoculation droplets. The proportion of expanding lesions on a particular genotype may then be divided by the proportion of expanding lesions observed in a control or reference genotype and expressed as a percentage. Alternatively, or additionally, lesion growth rates may be determined by calculating the increase in lesion size (e.g. in mm) over a suitable period, for instance over a 24 h period. Data for the non-expanding lesions may be deleted from the quantitative analysis. The lesion growth rate obtained may then optionally be divided by the lesion growth rate observed in a control or reference genotype and expressed as a percentage or as an absolute figure, for instance in millimeters.

Alternatively, plants can be screened by using a leaf infection bioassay as follows: First, tomato seeds are planted and grown to seedlings/plants. For each individual plant one or two compound leaves may be cut from the main stem and transferred to pre-wetted florist foam. The florist foam is then placed in a Petri dish containing tap water and subsequently placed in a spray-wetted container containing wet filter paper. A suitable inoculum comprising *B. cinerea* conidia may be prepared by methods known in the art, for instance as described by Benito et al., 1998. The compound leaves are then inoculated with the conidial suspension of *B. cinerea* by placing a number of droplets, suitably for instance 6 to 10 droplets of 2 µl each, onto the upper surface of the leaves. The container is then closed and the leaves are incubated at a temperature of suitably between 15° C.-20° C., preferably in the dark, and preferably at high humidity. At a number of suitable time intervals, for instance at 96, 120 and 144 hpi, the leaves may then be inspected for disease incidence and lesion growth, in a quantitative manner as described above for the stem bioassay.

A method for detecting a quantitative trait locus (QTL) associated with resistance to *Botrytis* in tomato according to the present invention further comprises the steps of establishing a genetic linkage map that links the observed disease incidence and/or the rate of lesion growth with the presence of chromosomal markers of said donor tomato plant in said one or more offspring plants and assigning contiguous markers on said map that are linked to a reduced disease incidence and/or a reduced rate of lesion growth to a quantitative trait locus.

A genetic linkage map that links the observed disease incidence and/or the rate of lesion growth with the presence of chromosomal markers of the donor tomato plant in said one or more offspring plants may be established by any method known in the art. The skilled person is aware of methods for identifying molecular markers linked to resistance quantitative trait loci (QTLs) and the mapping of these markers on a genetic linkage map (see e.g. Bai et al., 2003; Foolad et al., 2002; van Heusden et al., 1999). The association between the *Botrytis*-resistant phenotype and marker genotype may suitably be performed by using such software packages as Join-Map® and MapQTL® (see Examples) or any standard statistical package which can perform analysis of variance analysis. The molecular markers can be used to construct genetic linkage maps and to identify quantitative trait loci (QTLs) for *Botrytis* resistance. Suitable types of molecular markers and methods for obtaining those are described in more detail herein below.

A method for detecting a quantitative trait locus (QTL) associated with resistance to *Botrytis* in tomato according to the present invention may further be improved by reducing experimental variation in the bioassay and/or by the construction of a complete backcross inbred population (BIL). By using such a BIL line in combination with the methods of the present invention, the quantitative resistance to *B. cinerea* may be assessed even more precisely and additional QTLs may be identified.

Molecular Markers and QTLs

Molecular markers are used for the visualisation of differences in nucleic acid sequences. This visualisation is possible due to DNA-DNA hybridisation techniques (RFLP) and/or due to techniques using the polymerase chain reaction (e.g. STS, microsatellites, AFLP). All differences between two parental genotypes will segregate in a mapping population (e.g., $BC_1$, $F_2$; see FIG. 2) based on the cross of these parental genotypes. The segregation of the different markers may be compared and recombination frequencies can be calculated. The recombination frequencies of molecular markers on different chromosomes is generally 50%. Between molecular markers located on the same chromosome the recombination frequency depends on the distance between the markers. A low recombination frequency corresponds to a low distance between markers on a chromosome. Comparing all recombination frequencies will result in the most logical order of the molecular markers on the chromosomes. This most logical order can be depicted in a linkage map (Paterson, 1996). A group of adjacent or contiguous markers on the linkage map that is associated to a reduced disease incidence and/or a reduced lesion growth rate pinpoints the position of a QTL.

Upon the identification of the QTL, the QTL effect (the resistance) may for instance be confirmed by assessing *Botrytis*-resistance in $BC_2S_1$ progenies segregating for the QTLs under investigation. The assessment of the *Botrytis* resistance may suitably be performed by using a stem or leaf bioassay as described herein.

The QTLs for resistance against *Botrytis* in tomato obtainable by using a method of the invention are an aspect of the present invention. A characteristic of such QTLs is that, when present in plants, they are indicative of the presence of a reduced disease incidence and/or a reduced lesion growth rate upon contacting said plant with infective amount of *Botrytis* material, which material may be provided in any form, such as in the form of conidia or mycelium.

Figure 5:
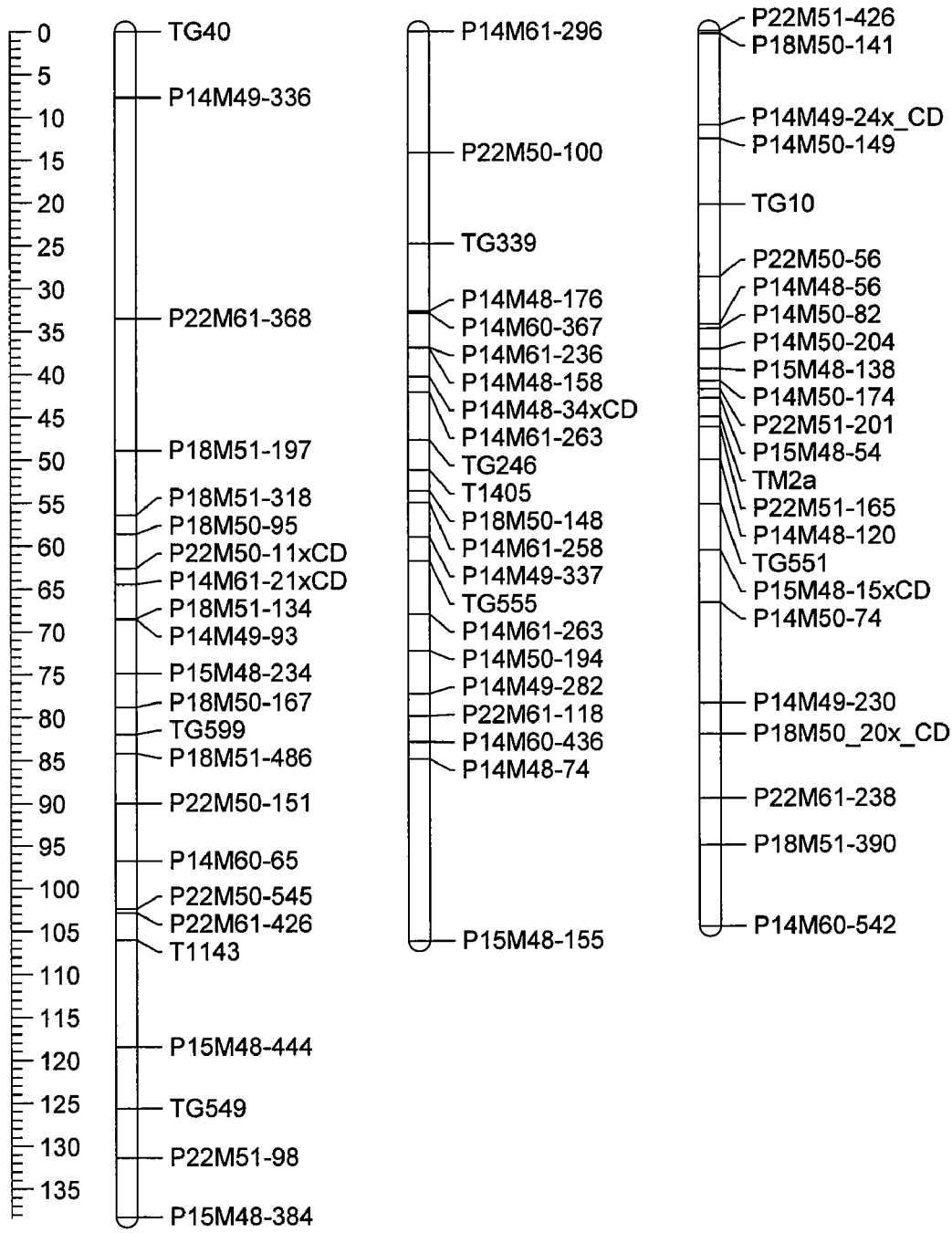
FIG. 5 shows a linkage map of the *L. parviflorum* QTLs as described herein. QTL-3p is located in the region indicated by markers P15M48-234, P18M50-167, TG599, P18M51-486, P22M50-151 and P14M60-65. QTL-4p is located in the region indicated by markers P14M48-158 and P14M48-34xCD (=P14M48-349 in Table 2). QTL-9p is located in the region indicated by markers TG10, P22M50-56, P14M48-56, P14M50-82, P14M50-204, P15M48-138 (=P15M48-137 in Table 2), P14M50-174 (=P14M50-176 in Table 2), P22M51-201, P15M48-54, TM2a, P22M51-165, P14M48-120, TG551, P15M48-15xCD (=P15M48-155 in Table 2).
Figure 6:
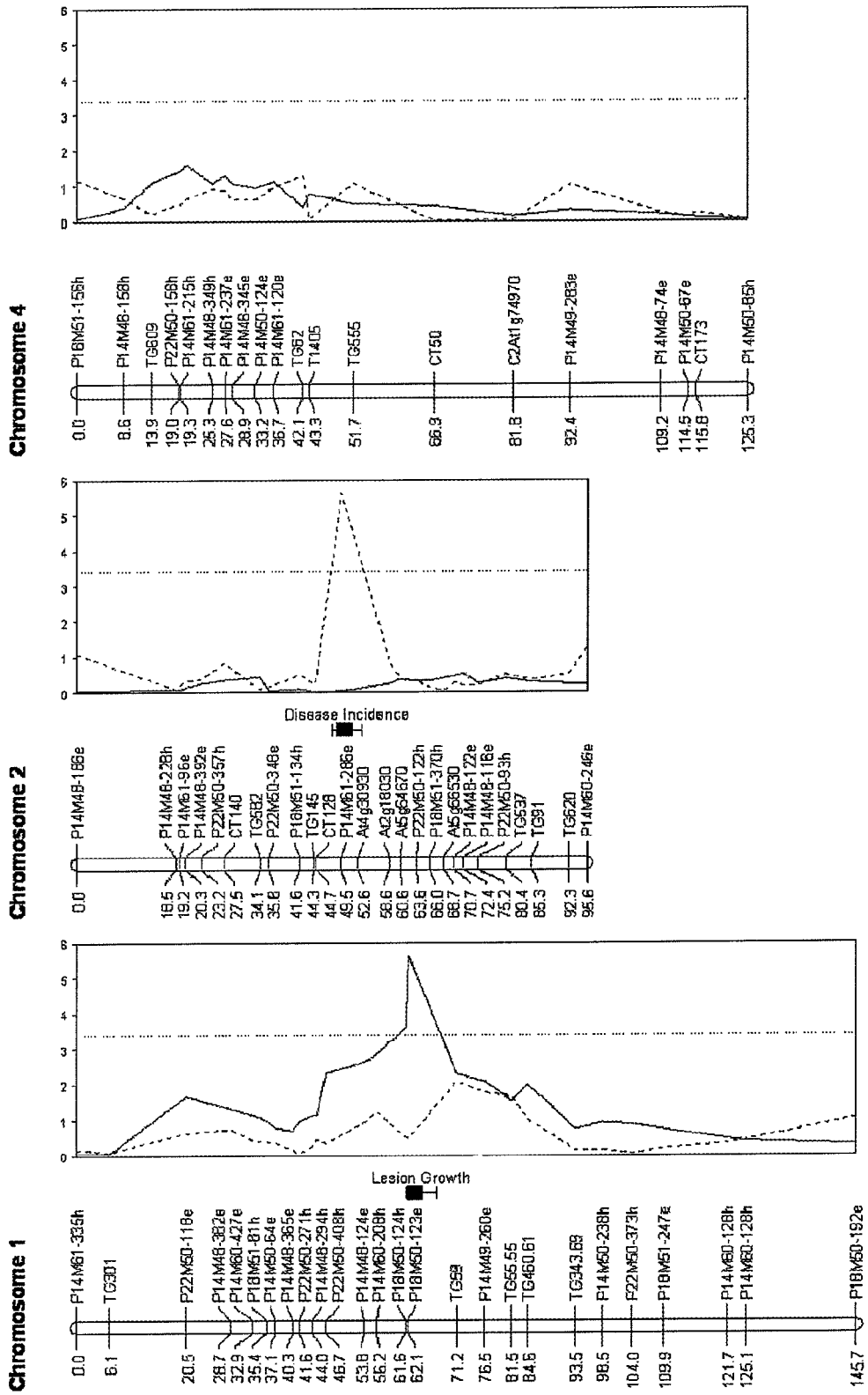
FIG. 6 shows a linkage map and QTL plots of the *L. hirsutum* QTLs as described herein. The map is an update to that of FIG. 1, showing the genomic regions more clearly. All markers indicated as associated to the QTLs (those running from TG301 through to and including TG460 on C1; those running from TG145 through to and including At5g64670 on C2; and those running from TG339 through to and including T1405 on C4) may be used as markers in aspects of the present invention. This updated version provides basis for preferred embodiments in aspects of the present invention.

The present invention also relates to a QTL for resistance against *Botrytis* in tomato, wherein said QTL is selected from the group consisting of the QTLs on chromosomes 1, 2 and 4 of *Lycopersicon hirsutum* LYC 4/78 and the QTLs on chromosomes 3, 4 and 9 in *Lycopersicon parviflorum* G1.1601 associated with *Botrytis* resistance. These QTLs may be more clearly defined or indicated by the markers listed in Tables 1 and 2 and as indicated in FIGS. 1, 5 and 6. Table 1 and FIGS. 1 and 6 indicate the QTLs found in the $F_2$ population derived from the cross of *L. esculentum* cv. Moneymaker×*L. hirsutum* LYC 4/78. Table 2 and FIG. 5 indicate the QTLs found in the $F_2$ population derived from the cross of *L. esculentum* cv. Moneymaker×*L. parviflorum* G1.1601. In both tables, the genomic region where the QTLs are located is indicated by the AFLP-markers listed. The QTLs of the present invention comprise genetic information in the form of DNA responsible for conferring (partial) *Botrytis* disease incidence or a reduced rate of *Botrytis* lesion growth in a tomato plant. The genetic information may for instance comprise a gene or a regulatory element.

Most reliably, the genomic region where QTL-1h is located is positioned between markers TG301 (Table 11) and TG460.61 (Table 12) as shown in FIG. 6. Therefore, any marker located within that region may be used to assess the presence of the QTL in the genome of a plant, as well as any marker known to be located in that region based on publicly available information, such as from consensus maps Tomato-EXPEN 1992 (Tanksley et al., 1992), Tomato-EXHIR 1997 (Bernacchi and Tanksley, 1997), Tomato-EXPEN 2000 (Fulton et al., 2002) or Tomato-EXPIMP 2001 (Grandillo and Tanksley, 1996; Tanksley et al. 1996, Doganlar et al. 2002). Most preferred regions are indicated by a bar in FIG. 6.

Most reliably, the genomic region where QTL-2h is located is positioned between markers TG145 (Table 15) and At5g64670 (Table 19) as shown in FIG. 6. Therefore, any marker located within that region may be used to assess the presence of the QTL in the genome of a plant, as well as any marker known to be located in that region based on publicly available information. Most preferred regions are indicated by a bar in FIG. 6.

Most reliably, the genomic region where QTL-4h is located is positioned between markers TG609 (Table 20) and C2Atlg74970 (Table 24) as shown in FIG. 6. Therefore, any marker located within that region may be used to assess the presence of the QTL in the genome of a plant, as well as any marker known to be located in that region based on publicly available information.

TABLE 1

QTLs found in offspring of a cross of *L. esculentum* cv. Moneymaker × *L. hirsutum* LYC 4/78 and related quantitative resistance information.

| QTL | Marker[1]* | Code[2] | Chromosome | Disease incidence[3,4] | Size of lesions[3,4] |
|---|---|---|---|---|---|
| QTL-1h for lesion growth | P-GT M-CAT-412h | P22M50-412h | 1 | aa 50.1 | aa 8.8 mm |
| | P-AT M-CAT-349h | P14M50-349h | | ab 50.0 | ab 7.8 mm |
| | P-AT M-CTC-69h | P14M60-69h | | bb 42.8 | bb 7.1 mm |
| | P-AT M-CAG-192h | P14M49-192h | | | |
| | P-AT M-CAG-232h | P14M49-232h | | | |
| | P-AT M-CAG-260e | P14M49-260e | | | |
| | P-AT M-CAT-503h | P14M50-503h | | | |
| | P-CT M-CAT-124h | P18M50-124h | | | |
| | P-AT M-CAG-114h | P14M49-114h | | | |
| QTL-2h for disease incidence | P-AT M-CTC-537h | P14M60-537h | 2 | aa 63.4 | aa 7.6 mm |
| | P-CA M-CAC-257e | P15M48-257e | | ab 47.1 | ab 7.9 mm |
| | P-AT M-CAG-327h | P14M49-327h | | bb 43.5 | bb 7.8 mm |
| | P-AT M-CAG-325h | P14M49-325h | | | |
| | P-AT M-CTG-286e | P14M61-286e | | | |
| | P-AT M-CTG-125h | P14M61-125h | | | |
| | P-CT M-CCA-134h | P18M51-134h | | | |
| | CT128[5] | idem | | | |
| QTL-4h for disease incidence | P-CT M-CCA-170e | P18M51-169.5e | 4 | aa 51% | Not determined |
| | P-CT M-CCA-305h | P18M51-305.4h | | ab 53% | |
| | P-AT M-CTC-263e | P14M60-262.9e | | bb 42% | |
| | P-AT M-CTG-293h | P14M61-292.7h | | | |
| QTL-4h for disease incidence (Test based on other markers) | TG609[6] | idem | 4 | aa 66% | Not determined |
| | | P14M48-345e | | ab 69% | |
| | | P14M48-177e | | bb 46% | |
| | | P18M50-147e | | | |

[1]Marker nomenclature: e.g. P-GT M-CAT-412h, wherein P and M are the common PstI and MseI primer sequences or universal primers (Vos et al., 1995; Bai et al. 2003) followed by 2 or 3 extra selective bases as indicated by a two digit extension code. 412 is the approximated size in basepairs of the resulting polymorphic fragment (given size ± 2 basepairs). The size is normally rounded off but may also be given in decimals. This fragment is amplified in either *L. esculentum* cv Moneymaker (e) or *L. hirsutum* LYC 4/78 (h). Primer and adapter sequences are described in detail by Bai et al. 2003.
[2]Codes by which the AFLP primer combination is commonly indicated. For P, M see marker nomenclature. Two digit extension codes are as follows: 14: AT; 15: CA; 18: CT; 22: GT; 48: CAC; 49: CAG; 50: CAT; 51: CCA; 60: CTC; 61: CTG.
[3]aa, marker homozygous *L. esculentum*; ab, marker heterozygous; bb, marker homozygous wild relative *L. hirsutum* LYC 4/78.
[4]Disease incidence and lesion growth are determined using methods as explained in detail in the Examples.
[5]CT128 (see Table 25) is a marker located on chromosome 2 position 44 cM on the Tanksley map (Tanksley et al. 1992).
[6]TG609 (see Table 20) is an RFLP Marker located on chromosome 4 position 38 cM on the Tomato-EXPEN 1992 composite map based on a *S. lycopersicum* cv. VF36 × *S. pennellii* LA716 F2 population (Tanksley et al. 1992).

TABLE 2

QTLs found in offspring of a cross of *L. esculentum* cv. Moneymaker × *L. parviflorum* G1.1601 and related quantitative resistance information.

| QTL | Marker[1] | Code[2] | Chromosome | Disease incidence[3] (no. of individuals) | Size of lesions |
|---|---|---|---|---|---|
| QTL-3p for disease incidence | P-CA M-CAC-234p<br>P-CT M-CCA-486p<br>P-AT M-CTC-65p | P15M48-234p<br>P18M51-486p<br>P14M60-65p | 3 | aa 70% (12)<br>b- 49% (87) | aa 5.7 mm<br>b- 5.1 mm |
| QTL-4p for disease incidence | E-AGA M-CAT-115p<br>P-AT M-CAC-158p<br>P-AT M-CAC-349p | E39M50-115p<br>P14M48-158p<br>P14M48-349p | 4 | aa 58% (17)<br>b- 45% (76) | aa 5.9 mm<br>b- 5.1 mm |
| QTL-9p for lesion growth | P-AT M-CAT-176p<br>P-CA M-CAC-137p<br>P-CA M-CAC-155p | P14M50-176p<br>P15M48-137p<br>P15M48-155p | 9 | aa 49% (27)<br>b- 51% (56) | aa 5.8 mm<br>b- 4.9 mm |

[1]Marker nomenclature: e.g. P-CA M-CAC-234p, wherein P, M and E are the common PstI, EcoRI and MseI primer sequences or universal primers (Vos et al., 1995; Bai et al. 2003) followed by 2 or 3 extra selective bases as indicated. 234 is the approximated size in base pairs of the resulting polymorphic fragment (given size ± 2 base pairs). This fragment is amplified in either *L. esculentum* cv Moneymaker (e) or *L. parviflorum* G1.1601 (p). Primer and adapter sequences are described in detail by Bai et al. 2003.
[2]Codes by which the AFLP primer combination is commonly indicated. For P, M see marker nomenclature.
[3]aa, marker homozygous *L. esculentum*; b-, one allele wild relative (here *L. parviflorum*) and the other allele can be either *L. esculentum* or wild relative.

Most reliably, the genomic region where QTL-3p is located is indicated by markers P15M48-234, P18M50-167, TG599, P18M51-486, P22M50-151 and P14M60-65.

Most reliably, the genomic region where QTL-4p is located is indicated by markers P14M48-158 and P14M48-34xCD (=P14M48-349 in Table 2).

Most reliably, the genomic region where QTL-9p is located is indicated by markers TG10, P22M50-56, P14M48-56, P14M50-82, P14M50-204, P15M48-138 (=P15M48-137 in Table 2), P14M50-174 (=P14M50-176 in Table 2), P22M51-201, P15M48-54, TM2a, P22M51-165, P14M48-120, TG551, P15M48-15xCD (=P15M48-155 in Table 2).

All markers for the QTLs found in offspring of a cross of *L. esculentum* cv. Moneymaker×*L. parviflorum* G1.1601 as described herein, as well as any marker known to be located in that region based on publicly available information may be used in aspects of the present invention.

Preferably, a QTL of the present invention comprises at least one marker of Table 1 or 2 or as indicated in FIGS. 1, 5 or 6 associated with said QTL. Because the nucleic acid sequence of the QTL that is responsible for conferring the *Botrytis* resistance may only be a fraction of the entire QTL herein identified, the markers merely indicate linked inheritance of genetic regions or the absence of observed recombination within such genetic regions. Therefore, it is noted that the markers listed in Tables 1 and 2 and as indicated in FIGS. 1, 5 and 6 indicate the chromosomal region where a QTL of the invention is located in the genome of the specified *Lycopersicon* lines and that those markers do not necessarily define the boundaries or the structure of that QTL. Thus, the part of the QTL that comprises the essential resistance-conferring nucleic acid sequence(s) may be considerably smaller than that indicated by the contiguous markers listed for a particular QTL. Such a part is herein referred to as a "resistance-conferring part" of a QTL. As a result a resistance-conferring part of a QTL need not necessarily comprise any of said listed markers. Also other markers may be used to indicate the various QTLs, provided that such markers are genetically linked to the QTLs and the skilled person may find or use a QTL that is analogous to those of the present invention, but wherein one or more markers listed in table 1 or 2 or indicated in FIGS. 1, 5 or 6 as being linked to said QTL are absent.

A *Botrytis*-resistance-conferring part of a QTL for resistance against *Botrytis* in tomato may be identified by using a molecular marker technique, for instance with one or more of the markers for a QTL shown in Table 1 or 2 or indicated in FIGS. 1, 5 or 6 as being linked to said QTL, preferably in combination with a resistance bioassay. Tomato plants that do not comprise a *Botrytis*-resistance-conferring part of a QTL of the present invention are relatively susceptible to infection by *Botrytis*.

The markers provided by the present invention may very suitably be used for detecting the presence of one or more QTLs of the invention in a suspected *Botrytis*-resistant tomato plant, and may therefore be used in methods involving marker-assisted breeding and selection of *Botrytis* resistant tomato plants. Preferably, detecting the presence of a QTL of the invention is performed with at least one of the markers for a QTL shown in Table 1 or 2 or as indicated in FIGS. 1, 5 or 6 as being linked to said QTL. The present invention therefore relates in another aspect to a method for detecting the presence of a QTL for *Botrytis*-resistance, comprising detecting the presence of a nucleic acid sequence of said QTL in a suspected *Botrytis*-resistant tomato plant, which presence may be detected by the use of the said markers.

The nucleic acid sequence of a QTL of the present invention may be determined by methods known to the skilled person. For instance, a nucleic acid sequence comprising said QTL or a resistance-conferring part thereof may be isolated from a *Botrytis*-resistant donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

The present invention therefore also relates to an isolated nucleic acid (preferably DNA) sequence that comprises a QTL of the present invention, or a *Botrytis*-resistance-conferring part thereof. Thus, the markers that pinpoint the various QTLs described herein may be used for the identification, isolation and purification of one or more genes from tomato that encode for *Botrytis* resistance.

The nucleotide sequence of a QTL of the present invention may for instance also be resolved by determining the nucleotide sequence of one or more markers associated with said QTL and designing internal primers for said marker sequences that may then be used to further determine the sequence the QTL outside of said marker sequences. For instance the nucleotide sequence of the AFLP markers from Tables 1 and 2 may be obtained by isolating said markers from the electrophoresis gel used in the determination of the presence of said markers in the genome of a subject plant, and determining the nucleotide sequence of said markers by for instance dideoxy chain terminating methods, well known in the art.

In embodiments of such methods for detecting the presence of a QTL in a suspected *Botrytis*-resistant tomato plant, the method may also comprise the steps of providing a oligonucleotide or polynucleotide capable of hybridizing under stringent hybridization conditions to a nucleic acid sequence of a marker linked to said QTL, preferably selected from the markers of Tables 1 and 2 and as indicated in FIGS. 1, 5 or 6 as being linked to said QTL, contacting said oligonucleotide or polynucleotide with a genomic nucleic acid of a suspected *Botrytis*-resistant tomato plant, and determining the presence of specific hybridization of said oligonucleotide or polynucleotide to said genomic nucleic acid. Preferably said method is performed on a nucleic acid sample obtained from said suspected *Botrytis*-resistant tomato plant, although in situ hybridization methods may also be employed. Alternatively, and in a more preferred embodiment, the skilled person may, once the nucleotide sequence of the QTL has been determined, design specific hybridization probes or oligonucleotides capable of hybridizing under stringent hybridization conditions to the nucleic acid sequence of said QTL and may use such hybridization probes in methods for detecting the presence of a QTL of the invention in a suspected *Botrytis*-resistant tomato plant.

The phrase "stringent hybridization conditions" refers to conditions under which a probe or polynucleotide will hybridize to its target subsequence, typically in a complex mixture of nucleic acids, but to essentially no other sequences. Stringent conditions are sequence-dependent and will be different in different circumstances. Longer sequences hybridize specifically at higher temperatures. An extensive guide to the hybridization of nucleic acids is found in Tijssen (Thijssen, 1993). Generally, stringent conditions are selected to be about 5-10° C. lower than the thermal melting point (Tm) for the specific sequence at a defined ionic strength pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. Additional guidelines for determining hybridization parameters are provided in numerous references, e.g., *Current Protocols in Molecular Biology*, eds. Ausubel et al. 1995).

"Nucleic acid" or "oligonucleotide" or "polynucleotide" or grammatical equivalents used herein means at least two nucleotides covalently linked together. Oligonucleotides are typically from about 7, 8, 9, 10, 12, 15, 18 20 25, 30, 40, 50 or up to about 100 nucleotides in length. Nucleic acids and polynucleotides are a polymers of any length, including longer lengths, e.g., 200, 300, 500, 1000, 2000, 3000, 5000, 7000, 10.000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, 1991), and peptide nucleic acid backbones and linkages. Mixtures of naturally occurring nucleic acids and analogs can be used. Particularly preferred analogs for oligonucleotides are peptide nucleic acids (PNA).

Production of *Botrytis*-Resistant Tomato Plants by Transgenic Methods

According to another aspect of the present invention, a nucleic acid (preferably DNA) sequence comprising at least one QTL of the present invention or a *Botrytis*-resistance-conferring part thereof, may be used for the production of a *Botrytis*-resistant tomato plant. In this aspect, the invention provides for the use of a QTL of to the present invention or *Botrytis*-resistance-conferring parts thereof, for producing a *Botrytis*-resistant tomato plant, which use involves the introduction of a nucleic acid sequence comprising said QTL in a *Botrytis*-susceptible recipient tomato plant. As stated, said nucleic acid sequence may be derived from a suitable *Botrytis*-resistant donor tomato plant. Two suitable *Botrytis*-resistant donor tomato plants capable of providing a nucleic acid sequence comprising at least one of the hereinbefore described QTLs, or *Botrytis*-resistance-conferring parts thereof, are *L. hirsutum* LYC 4/78 and *L. parviflorum* G1.1601. Other related tomato plants that exhibit resistance to *Botrytis* and comprise one or more genes that encode for Botrytis resistance may also be utilized as *Botrytis*-resistance donor plants as the present invention describes how this material may be identified. Other accessions of tomato species can be examined for *Botrytis*-resistance including, but not limited to, *Lycopersicon cerasiforme*, *Lycopersicon cheesmanii*, *Lycopersicon chilense*, *Lycopersicon chmielewskii*, *Lycopersicon esculentum*, *Lycopersicon hirsutum*, *Lycopersicon parviflorum*, *Lycopersicon pennellii*, *Lycopersicon peruvianum*, *Lycopersicon pimpinellifolium* and *Solanum lycopersicoides*.

Once identified in a suitable donor tomato plant, the nucleic acid sequence that comprises a QTL for *Botrytis*-resistance according to the present invention, or a *Botrytis*-resistance-conferring part thereof, may be transferred to a suitable recipient plant by any method available. For instance, the said nucleic acid sequence may be transferred by crossing a *Botrytis*-resistance donor tomato plant with a susceptible recipient tomato plant (i.e. by introgression), by transformation, by protoplast fusion, by a doubled haploid technique or by embryo rescue or by any other nucleic acid transfer system, optionally followed by selection of offspring plants comprising the QTL and exhibiting *Botrytis*-resistance. For transgenic methods of transfer a nucleic acid sequence comprising a QTL for *Botrytis*-resistance according to the present invention, or a *Botrytis*-resistance-conferring part thereof, may be isolated from said donor plant by using methods known in the art and the thus isolated nucleic acid sequence may be transferred to the recipient plant by transgenic methods, for instance by means of a vector, in a gamete, or in any other suitable transfer element, such as a ballistic particle coated with said nucleic acid sequence.

Plant transformation generally involves the construction of an expression vector that will function in plant cells. In the present invention, such a vector comprises a nucleic acid sequence that comprises a QTL for *Botrytis*-resistance of the present invention, or a *Botrytis*-resistance-conferring part thereof, which vector may comprise a *Botrytis*-resistance-conferring gene that is under control of or operatively linked to a regulatory element, such as a promoter. The expression vector may contain one or more such operably linked gene/regulatory element combinations, provided that at least one of the genes contained in the combinations encodes for *Botrytis*-resistance. The vector(s) may be in the form of a plasmid, and can be used, alone or in combination with other plasmids, to provide transgenic plants that are resistant to *Botrytis*, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

One method for introducing an expression vector into a plant is based on the natural transformation system of *Agrobacterium* (see e.g. Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (see e.g. Kado, 1991). Methods of introducing expression vectors into plant tissue include the direct infection or co-cultivation of plant cells with *Agrobacterium tumefaciens* (Horsch et al., 1985). Descriptions of *Agrobacterium* vectors systems and methods for *Agrobacterium*-mediated gene transfer provided by Gruber and Crosby, 1993 and Moloney et al., 1989. See also, U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993. General methods of culturing plant tissues are provided for example by Miki et al., 1993 and by Phillips, et al., 1988. A proper reference handbook for molecular cloning techniques and suitable expression vectors is Sambrook and Russell (2001).

Another method for introducing an expression vector into a plant is based on microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes (See, Sanford et al., 1987, 1993; Sanford, 1988, 1990; Klein et al., 1988, 1992). Another method for introducing DNA to plants is via the sonication of target cells (see Zhang et al., 1991). Alternatively, liposome or spheroplast fusion has been used to introduce expression vectors into plants (see e.g. Deshayes et al., 1985 and Christou et al., 1987). Direct uptake of DNA into protoplasts using $CaCl_2$ precipitation, polyvinyl alcohol or poly-L-ornithine has also been reported (see e.g., Hain et al. 1985 and Draper et al., 1982). Electroporation of protoplasts and whole cells and tissues has also been described (D'Halluin et al., 1992 and Laursen et al., 1994).

Following transformation of tomato target tissues, expression of the above described selectable marker genes allows for preferential selection of transformed cells, tissues and/or plants, using regeneration and selection methods now well known in the art. The markers of Tables 1 or 2 may also be used for that purpose.

Production of *Botrytis*-Resistant Tomato Plants by Non-Transgenic Methods

In an alternative embodiment for producing a *Botrytis*-resistant tomato plant, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbred in nature, is tissue cultured into a hybrid plant exhibiting the desirable combination of traits. More specifically, a first protoplast can be obtained from a tomato plant or other plant line that exhibits resistance to infection by *Botrytis*. For example, a protoplast from *L. hirsutum* LYC 4/78 can be used. A second protoplast can be obtained from a second tomato or other plant variety, preferably a tomato line that comprises commercially desirable characteristics, such as, but not limited to disease resistance, insect resistance, valuable fruit characteristics, etc. The protoplasts are then fused using traditional protoplast fusion procedures, which are known in the art.

Alternatively, embryo rescue may be employed in the transfer of a nucleic acid comprising one or more QTLs of the present invention from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (Pierik, 1999).

The present invention also relates to a method of producing a *Botrytis*-resistant tomato plant comprising the steps of performing a method for detecting the presence of a quantitative trait locus (QTL) associated with resistance to *B. cinerea* in a donor tomato plant according to invention as described above, and transferring a nucleic acid sequence comprising at least one QTL thus detected, or a *Botrytis*-resistance-conferring part thereof, from said donor plant to a *Botrytis*-susceptible recipient tomato plant. The transfer of said nucleic acid sequence may be performed by any of the methods previously described herein.

A preferred embodiment of such a method comprises the transfer by introgression of said nucleic acid sequence from a *Botrytis*-resistant donor tomato plant into a *Botrytis*-susceptible recipient tomato plant by crossing said plants. This transfer may thus suitably be accomplished by using traditional breeding techniques. QTLs are preferably introgressed into commercial tomato varieties by using marker-assisted breeding (MAS). Marker-assisted breeding or marker-assisted selection involves the use of one or more of the molecular markers for the identification and selection of those offspring plants that contain one or more of the genes that encode for the desired trait. In the present instance, such identification and selection is based on selection of QTLs of the present invention or markers associated therewith. MAS can also be used to develop near-isogenic lines (NIL) harboring the QTL of interest, allowing a more detailed study of each QTL effect and is also an effective method for development of backcross inbred line (BIL) populations (see e.g. Nesbitt et al., 2001; van Berloo et al., 2001). Tomato plants developed according to this preferred embodiment can advantageously derive a majority of their traits from the recipient plant, and derive Botrytis-resistance from the donor plant.

Since it is now found that resistance to B. cinerea is inherited polygenically, it is preferred that at least two, preferably three QTLs or Botrytis-resistance-conferring parts thereof, are inserted by a suitable transfer method into a single recipient plant, i.e. that multiple QTLs are stacked in the recipient plant's genome. It is believed that stacking of two or more QTLs of the invention may lead to increased resistance to Botrytis. As the skilled person will readily understand, stacking may be achieved by any method, for instance by transforming a plant with a nucleic acid construct comprising multiple QTLs of the invention. Alternatively, at least one QTL may be present in each parent plant of a cross, so that at least two QTLs are comprised in the resulting hybrid. By stacking of these resistance traits highly resistant plants may be obtained. Such plants are highly preferred embodiments of the present invention.

As discussed briefly above, traditional breeding techniques can be used to introgress a nucleic acid sequence encoding for Botrytis resistance into a Botrytis-susceptible recipient tomato plant. In one method, which is referred to as pedigree breeding, a donor tomato plant that exhibits resistance to Botrytis and comprising a nucleic acid sequence encoding for Botrytis resistance is crossed with a Botrytis-susceptible recipient tomato plant that preferably exhibits commercially desirable characteristics, such as, but not limited to, disease resistance, insect resistance, valuable fruit characteristics, etc. The resulting plant population (representing the $F_1$ hybrids) is then self-pollinated and set seeds ($F_2$ seeds). The $F_2$ plants grown from the $F_2$ seeds are then screened for resistance to Botrytis. The population can be screened in a number of different ways.

First, the population can be screened using a traditional disease screen. Such disease screens are known in the art. Preferably a quantitative stem or leaf infection bioassay is used, preferably the stem bioassay used in methods of the present invention as outlined in more detail hereinabove and the Examples is used. Second, marker-assisted selection can be performed using one or more of the hereinbefore-described molecular markers to identify those progeny that comprise a nucleic acid sequence encoding for Botrytis-resistance. Other methods, referred to hereinabove by methods for detecting the presence of a QTL may be used. Also, marker-assisted selection can be used to confirm the results obtained from the quantitative bioassays, and therefore, several methods may also be used in combination.

Botrytis-Resistant Tomato Plants and Seeds

A Botrytis-resistant tomato plant of the present invention is characterized by having a high level of resistance. This is defined as being a resistance level that is higher than that observed for susceptible control plants. In fact, the plants of the invention have a level of resistance that is higher than that of any commercial tomato variety, i.e. a variety having commercially desirable characteristics, known to date. A plant of the invention has a susceptibility to Botrytis cinerea which is at least 3 times lower than a susceptible control plant when measured by a bioassay. For instance when measured by a bioassay wherein the average length of a stem lesion resulting from Botrytis cinerea infection in adult plants is measured during a three week period under standard practice conditions as described in more detail in the Examples 3.10 and 3.11. Typically, a plant of the invention has a level of resistance that results in an average stem lesion length of Botrytis cinerea lesions in adult plants of less than 3.2 cm three weeks after inoculation using standard practice conditions in a resistance bioassay designed to determine resistance based on such characteristics. More typically, a plant of the invention shows an average stem lesion length of less than 2.9 cm. Some plants of the invention even show an average stem lesion length of 2.0 cm. Taking into account that said numbers express the length of a lesion including the 2 cm initial inoculation wound, it can be inferred that a high level of resistance, and even full resistance in the case of some QTLs, is observed in plants of the invention. In comparison, susceptible control plants show a mean average stem lesion length under the same conditions of about 3.6 cm to about 6.0 cm, with an average of 4.85 cm (see Table 10). Also as a comparison, L. hirsutum LA 1777, the QTL-10 containing partially Botrytis resistant source of WO02/085105, shows an average stem lesion length under the same conditions of about 4.3 cm. In summary, the plants of the invention show net stem lesions in the above referred resistance bioassay that are generally less than about 30% (0.9/2.85×100%) of the net length of susceptible control plants, and generally less than about 40% (0.9/2.3× 100%) of the net length of partially resistant L. hirsutum LA 1777.

Thus, a plant of the present invention has a susceptibility to Botrytis cinerea when measured by a bioassay which is 3 times lower than, or which is less than ⅓ the level of, a susceptible control plant. Reciprocally, a plant of the invention is more than 3 times more resistant than a susceptible control plant, as defined herein and determined with the bioassay as described. With some QTLs or combinations of QTLs (e.g. QTL-1h and the combinations of QTL-3p+QTL-4p or QTL-9p+QTL-4p) full resistance is observed (See Table 10). A susceptible control plant is defined as a plant showing normal susceptibility, or no resistance, to Botrytis cinerea infection. Examples of susceptible control plants are the hybrid Lycopersicon esculentum cv. "Tradiro," and Lycopersicon esculentum cv. "Moneyberg" (De Ruiter Seeds CV, Bergschenhoek, The Netherlands).

A Botrytis-resistant tomato plant, or a part thereof, obtainable by a method of the invention is also an aspect of the present invention.

Another aspect of the present invention relates to a Botrytis-resistant tomato plant, or part thereof, comprising within its genome at least one QTL, or a Botrytis-resistance-conferring part thereof, selected from the group consisting of the QTLs on chromosomes 1, 2 and 4 of Lycopersicon hirsutum LYC 4/78 and the QTLs on chromosomes 3, 4 and 9 in Lycopersicon parviflorum G1.1601 associated with Botrytis resistance, wherein said QTL or said Botrytis-resistance-conferring part thereof is not in its natural genetic background. The Botrytis-resistant tomato plants of the present invention can be of any genetic type such as inbred, hybrid, haploid, dihaploid, parthenocarp or transgenic. Further, the plants of the present invention may be heterozygous or homozygous for the resistance trait, preferably homozygous. Although the QTLs of the present invention, as well as those QTLs obtainable by a method of the invention, as well as Botrytis-resistance-conferring parts thereof may be transferred to any plant in order to provide for a Botrytis-resistant plant, the methods and plants of the invention are preferably related to plants of the Solanaceae family, more preferably tomato.

Inbred *Botrytis*-resistant tomato plant lines can be developed using the techniques of recurrent selection and backcrossing, selfing and/or dihaploids or any other technique used to make parental lines. In a method of selection and backcrossing, *Botrytis*-resistance can be introgressed into a target recipient plant (which is called the recurrent parent) by crossing the recurrent parent with a first donor plant (which is different from the recurrent parent and referred to herein as the "non-recurrent parent"). The recurrent parent is a plant that is non-resistant or has a low level of resistance to *Botrytis* and possesses commercially desirable characteristics, such as, but not limited to disease resistance, insect resistance, valuable fruit characteristics, etc. The non-recurrent parent exhibits *Botrytis* resistance and comprises a nucleic acid sequence that encodes for *Botrytis* resistance. The non-recurrent parent can be any plant variety or inbred line that is cross-fertile with the recurrent parent. The progeny resulting from a cross between the recurrent parent and non-recurrent parent are backcrossed to the recurrent parent. The resulting plant population is then screened. The population can be screened in a number of different ways. For instance, the population can be screened using a stem quantitative bioassays as described previously herein. $F_1$ hybrid plants that exhibit a *Botrytis*-resistant phenotype comprise the requisite nucleic acid sequence encoding for *Botrytis* resistance, and possess commercially desirable characteristics, are then selected and selfed and selected for a number of generations in order to allow for the tomato plant to become increasingly inbred. This process of continued selfing and selection can be performed for two to five or more generations. The result of such breeding and selection is the production of lines that are genetically homogenous for the genes associated with *Botrytis* resistance as well as other genes associated with traits of commercial interest. In stead of using phenotypic pathology screens of bioassays, MAS can be performed using one or more of the hereinbefore described molecular markers, hybridization probes or polynucleotides to identify those progeny that comprise a nucleic acid sequence encoding for *Botrytis*-resistance. Alternatively, MAS can be used to confirm the results obtained from the quantitative bioassays. Once the appropriate selections are made, the process is repeated. The process of backcrossing to the recurrent parent and selecting for *Botrytis*-resistance is repeated for approximately five or more generations. The progeny resulting from this process are heterozygous for one or more genes that encode for *Botrytis*-resistance. The last backcross generation is then selfed in order to provide for homozygous pure breeding progeny for *Botrytis*-resistance.

The *Botrytis*-resistant inbred tomato lines described herein can be used in additional crossings to create *Botrytis*-resistant hybrid plants. For example, a first *Botrytis*-resistant inbred tomato plant of the invention can be crossed with a second inbred tomato plant possessing commercially desirable traits such as, but not limited to, disease resistance, insect resistance, desirable fruit characteristics, etc. This second inbred tomato line may or may not be *Botrytis*-resistant.

Another aspect of the present invention relates to a method of producing seeds that can be grown into *Botrytis*-resistant tomato plants. In one embodiment, the method comprises the steps of providing a *Botrytis*-resistant tomato plant of the invention, crossing said *Botrytis*-resistant plant with a *Lycopersicon esculentum* plant, and collecting seeds resulting from said cross, which when planted, produce *Botrytis*-resistant tomato plants.

In another embodiment, the method comprises the steps of providing a *Botrytis*-resistant tomato plant of the invention, crossing said *Botrytis*-resistant plant with a *Lycopersicon esculentum* plant, collecting seeds resulting from said cross, regenerating said seeds into plants, selecting *Botrytis*-resistant plants by any of the methods described herein, self-crossing the selected plants for a sufficient number of generations to obtain plants that are fixed for an allele that confers *Botrytis*-resistance in the plants, backcrossing the plants thus produced with *L. esculentum* plants having desirable phenotypic traits for a sufficient number of generations to obtain *L. esculentum* plants that are *Botrytis*-resistant and have desirable phenotypic traits, and collecting the seeds produced from the plants resulting from the last backcross, which when planted, produce tomato plants which are *Botrytis*-resistant.

By way of example, and not of limitation, Examples of the present invention will now be given.

EXAMPLES

Example 1

Method of Identifying Plants Resistant to *Botrytis cinerea*

1.1. Introduction

This Example presents the development of a quantitative bioassay for evaluating the resistance to *Botrytis cinerea* of a collection of wild tomato genotypes.

Partial resistance against *Botrytis cinerea* has been reported in wild *Lycopersicon* species, but these reports have largely been descriptive and qualitative. The identification of partially resistant genotypes would provide perspectives to introgress resistance into commercial breeding lines to obtain lines with manageable resistance levels. The availability of a reproducible, objective and quantitative assay, as well as the identification of genotypes with a genetically determined (partial) grey mould resistance opens the way for resistance breeding in cultured tomato varieties.

The present Example describes a quantitative disease assay. The assay is applied on leaves (leaf inoculation assay) and stem segments (stem inoculation assay). Two parameters for disease susceptibility were examined. The first parameter was the disease incidence (DI), i.e. the proportion of inoculation droplets that resulted in an expanding lesion. If the (partial) failure of a primary *B. cinerea* lesion to expand on a particular host genotype is a genetic trait of the plant, such a trait is important as it directly limits the number of disease foci in the crop. The second parameter tested was the lesion growth rate over a period of 24 h (lesion growth, LG). Lesions that expanded from the primary inoculation spot appeared to spread at an even rate (in mm/day) over time until the lesion reached the edge of the leaf or the bottom end of the stem segment. The present assays enable the quantification of both the occurrence (disease incidence) and development (lesion growth) of *B. cinerea* infection, resulting in two sets of quantitative trait data. The assay was used to screen a collection of *Lycopersicon* species (hereinafter also termed "accessions") for the presence of resistance therein.

1.2. Plants
Plant genotypes tested are listed in Table 3.

TABLE 3

List of *Lycopersicon* genotypes tested

| Code | Source[1] | Species | Specification/ Cultivar | Leaf[2] | Stem[2] | Reference[3] |
|---|---|---|---|---|---|---|
| 78/1604 | DRS | *L. esculentum* | Kecksemeti Torpe | Y | Y | |
| 82/2577 | DRS | *L. esculentum* | Futuria | Y | Y | |
| 83/2896 | DRS | *L. esculentum* | Biruinca | Y | | |
| 89/3695 | DRS | *L. esculentum* | X *L. esculentum* var. *cerasiforme* | | Y | |
| 89/3793 | DRS | *L. pimpinellifolium* | | | Y | |
| 89/3862 | DRS | *L. esculentum* | Olomoucke | Y | | |
| 90/4063 | DRS | *L. esculentum* | L 4034 | Y | | |
| 91/4311 | DRS | *L. esculentum* | Seedathip 2 | Y | Y | |
| 96/4326 | DRS | *Solanum lycopersicoides* | Gb nr 90124 | Y | Y | |
| MM | WU PPW | *L. esculentum* | Moneymaker | S | S | |
| G1.1290 | WU LoPB | *L. hirsutum* | | | Y | |
| G1.1556 | WU LoPB | *L. chilense* | | Y | Y | |
| G1.1558 | WU LoPb | *L. chilense* | | Y | | |
| G1.1560 | WU LoPB | *L. hirsutum* | | Y | Y | |
| G1.1601 | WU LoPB | *L. parviflorum* | | Y | Y | |
| G1.1615 | WU LoPB | *l. cheesmanii* | | | Y | |
| IZ.2[3] | MPIZK | *L. pimpinellifolium* | | | Y | (Urbasch, 1986) |
| LA.716 | TGRC | *L. pennellii* | | Y | | |
| LA.2157 | TGRC | *L. peruvianum* | | | Y | |
| LA.2172 | TGRC | *L. peruvianum* | | | Y | |
| Lyc. 4/78[3] | IPK | *L. hirsutum* | | Y | Y | (Urbasch, 1986) |
| T160/79[3] | IPK | *L. glandulosum* | | | Y | (Urbasch, 1986) |
| T566/81[3] | IPK | *L. hirsutum* | | | Y | (Urbasch, 1986) |

[1]DRS: De Ruiter Seeds, Bergschenhoek, The Netherlands; WU PPW: Plantkundig Proefcentrum Wageningen, Wageningen University, Wageningen, The Netherlands; LoPB: Laboratory of Plant Breeding, Wageningen University, Wageningen, The Netherlands; MPIZK: Max Planck Institut für Züchtungsforschung an Kulturpflanze, Köln, Germany; TGRC: Tomato Genetics Resource Center, University of California at Davis, Davis CA, USA; IPK: Institut für Pflanzengenetik und Kulturpflanzenforschung, Gatersleben, Germany.
[2]Y indicates that the genotype was tested in the particular assay, S indicates the genotype served as a susceptible reference control.
[3]Published before as being resistant against *B. cinerea*.

Plants were grown in potting soil in 12 cm pots in a greenhouse with minimal temperature of 15° C. Artificial sodium lamplight was applied (16 h/day) from October through March. At 5-7 days after germination, 10 ml FeNaEDTA solution (3.5 g/l) was added, followed 3 days later by 10 ml of micronutrient solution (0.286 g/l $H_3BO_3$; 0.1558 g/l $MnSO_4.H_2O$; 0.008 g/l $CuO_4.H_2O$; 0.022 g/l $ZnSO_4$; 0.00196 $(NH_4)_6Mo_7O_{24}.4H_2O$). From two weeks after germination onwards, 5 ml of a Hoagland solution (5 mM $Ca(NO_3)_2$; 5 mM $KNO_3$; 2 mM $MgSO_4$; 1 mM $KH_2PO_4$) was added on a weekly basis.

1.3. Leaf Assay

An inoculum from *B. cinerea* strain B05.10 was prepared according to Benito (1998). For each individual plant one or two compound leaves that were fully stretched were detached from the main stem with a sharp razor blade and transferred to pre-wetted florist foam. The florist foam was placed in a Petri dish containing tap water and subsequently placed in a spray-wetted container containing wet filter paper. The compound leaves were then inoculated with a conidial suspension of *B. cinerea* by carefully pipetting a total of 6 to 10 droplets of inoculum (2 µl) onto the upper surface of the leaves. The containers were closed with a spray-wetted lid and incubated at 15° C. in the dark at 100% RH, essentially as described by Benito et al., 1998. The data in Table 4 were derived from a test wherein one composite leaf was divided into four leaflets, and wherein every leaflet was inoculated with 10 drops of 2 µl each, containing 2000 conidia. Both the proportion of aggressive expanding lesions (disease incidence) and the lesion growth rate were monitored over several days.

To correct for variation caused by the season or cultivation of the plants, the disease incidence of a particular genotype in each experiment was related to the disease incidence of Moneymaker tested in that same experiment.

Lesion sizes were measured at 96, 120 and 144 hpi using a caliper. The disease incidence was determined by dividing the total number of expanding lesions by the total number of inoculation droplets. Lesion growth rates were determined by calculating the increase in lesion size (in mm) over a 24 h period. Data for the non-expanding lesions were deleted from the quantitative analysis. The results of the leaf assay are presented in Table 4.

TABLE 4

Disease incidence (DI, in %) and lesion growth rates (LG, in mm/day ± standard deviation) in leaves of *Lycopersicon* accessions inoculated with *B. cinerea*. Experiments were conducted in 1999 and 2000 in different weeks as indicated.

| Accession | | 1999 Week 10 | 11 | 12 | 16 | 17 | 26 | 27 | 30 | 31 | 33 | 35 | 2000 Week 5 | 6 |
|---|---|---|---|---|---|---|---|---|---|---|---|---|---|---|
| 78/1604 | DI | | | | 19% | | | | | 14% | | | | |
| | LG | | | | 4.3 ± 1.5 | | | | | 3.3 ± 1.3 | | | | |
| 82/2577 | DI | | | | 26% | | | | | | | | 32% | |
| | LG | | | | 3.1 ± 2.0 | | | | | | | | 6.0 ± 2.0 | |
| 83/2896 | DI | | | | 38% | 23% | 55% | | 29% | | | | | |
| | LG | | | | 3.8 ± 1.3 | 4.3 ± 1.7 | 2.3 ± 0.9 | | 3.9 ± 1.2 | | | | | |
| 89/3862 | DI | | | | 61% | 9% | | | | | | | | |
| | LG | | | | 4.0 ± 1.0 | 3.1 ± 1.8 | | | | | | | | |
| 90/4063 | DI | | | | | | | | | | 53% | | | |
| | LG | | | | | | | | | | 3.8 ± 1.0 | | | |
| 91/4311 | DI | | | | | | 7% | | 4% | | | | 11% | |
| | LG | | | | | | 1.8 ± 0.7 | | 2.0 ± 0.7 | | | | 3.3 ± 1.3 | |
| 96/4326 | DI | | | 6% | | | 2% | | | 6% | 11% | | | |
| | LG | | | 7.0 ± 4.1 | | | 6.2 ± 1.0 | | | 3.1 ± 2.0 | 3.4 ± 2.4 | | | |
| T160/79 | DI | | | | | | | | | | 4% | | | |
| | LG | | | | | | | | | | 1.3 ± 0.9 | | | |
| G1.1556 | DI | | 0% | | | | 3% | | | | 5% | | | |
| | LG | | | | | | 2.4 ± 1.0 | | | | 0.8 ± 0.7 | | | |
| G1.1558 | DI | | | | | | | | | | | | | 20% |
| | LG | | | | | | | | | | | | | 2.9 ± 1.8 |
| G1.1560 | DI | | | | | | 4% | | | | 1% | | | 18% |
| | LG | | | | | | 2.8 ± 1.3 | | | | 3.3 ± 0.5 | | | 3.8 ± 2.0 |
| G1.1601 | DI | | | 21% | | | 1% | | | | 3% | | | |
| | LG | | | 5.2 ± 1.7 | | | 3.1 ± 0.9 | | | | 1.5 ± 1.3 | | | |
| LA716 | DI | 23% | 12% | | | | | | | | | | | |
| | LG | 7.4 ± 1.7 | 4.6 ± 1.7 | | | | | | | | | | | |
| LYC 4/78 | DI | | | | | | | | | | 3% | | | |
| | LG | | | | | | | | | | 1.1 ± 0.6 | | | |
| MM | DI | 78% | 24% | 53% | 73% | 19% | 57% | 31% | 25% | 65% | 15% | 77% | 26% | 41% |
| | LG | 6.4 ± 2.3 | 4.8 ± 1.8 | 8.2 ± 2.5 | 3.8 ± 1.4 | 3.9 ± 1.5 | 2.8 ± 1.0 | 4.6 ± 1.1 | 3.9 ± 1.1 | 3.4 ± 1.4 | 2.2 ± 1.5 | 4.3 ± 1.4 | 5.3 ± 1.6 | 3.6 ± 2.2 |

1.4. Stem Assay (Standardized Procedure)

The stem assay was performed as follows: The top 5-10 cm and bottom 5-10 cm of the stem of approximately 50 cm high plants were removed and the remaining 30 cm was cut into equal segments of 5-6 cm. Each stem segment was placed upright in a lattice with the stem base on wet filter paper. Prior to inoculation, the stem segments were sprayed with tap water in order to ensure an equal spread of the inoculum over the wound surface. Inoculum was prepared as described for the leaf assay. One drop of a 5 μl inoculum, containing approximately $10^6$ conidia·ml$^{-1}$, was applied on the top of each stem segment. Incubations were performed at 15±2° C. in the dark with 100% relative humidity. Infection progress was determined by measuring the maximum advance of rot symptom at various time intervals after inoculation with a Vernier caliper.

For each genotype, the percentage of infected stem pieces was calculated. The disease incidence was determined by dividing the total number of stem segments with expanding lesions by the total number of inoculated segments. Lesion growth rates were determined by calculating the increase in lesion size over a 24 h period, whereby the data for the non-expanding lesions were omitted from the analysis. The results of the stem assay are presented in Table 5.

TABLE 5

Disease incidence (DI, in %) and lesion growth rates (LG, in mm/day ± strd. dev.) in stem segments of *Lycopersicon* accessions inoculated with *B. cinerea*. Experiments were conducted in 1999 and 2000 in weeks indicated.

| Accession | | 1999 Week[1] 30 | 32 | 33 | 35 | 46 | 48 | 2000 5 | 6 | 27 | 30 |
|---|---|---|---|---|---|---|---|---|---|---|---|
| 78/1604 | DI | | | | | | | | | 64% | 87% |
| | LG | | | | | | | | | 7.8 ± 1.7 | 5.6 ± 1.2 |
| 82/2577 | DI | | 81% | | | | | 97% | | | |
| | LG | | 7.1 ± 2.4 | | | | | 5.8 ± 2.1 | | | |

TABLE 5-continued

Disease incidence (DI, in %) and lesion growth rates (LG, in mm/day ± strd. dev.) in stem segments of *Lycopersicon* accessions inoculated with *B. cinerea*. Experiments were conducted in 1999 and 2000 in weeks indicated.

| | | 1999 | | | | | | 2000 | | | |
|---|---|---|---|---|---|---|---|---|---|---|---|
| | | Week[1] | | | | | | | | | |
| Accession | | 30 | 32 | 33 | 35 | 46 | 48 | 5 | 6 | 27 | 30 |
| 89/3695 | DI | | 82% | | | | 70% | | | | |
| | LG | | 5.9 ± 2.1 | | | | 5.7 ± 3.0 | | | | |
| 89/3793 | DI | | | | | | | | | 57% | 57% |
| | LG | | | | | | | | | 2.7 ± 1.2 | 3.4 ± 1.7 |
| 91/4311 | DI | | | | | | 41% | | | | |
| | LG | | | | | | 5.5 ± 3.4 | | | | |
| 96/4326 | DI | | | 90% | | | | | | | |
| | LG | | | 7.8 ± 2.5 | | | | | | | |
| 160/79 | DI | | | 67% | | | | | | | |
| | LG | | | 2.2 ± 1.4 | | | | | | | |
| G1.1290 | DI | | | | | 19% | 72% | | | | |
| | LG | | | | | 3.0 ± 1.4 | 5.4 ± 2.0 | | | | |
| G1.1556 | DI | | | | | 29% | 41% | | | | |
| | LG | | | | | 3.7 ± 2.4 | 6.2 ± 5.0 | | | | |
| G1.1560 | DI | | | 28% | | | | | 7% | | |
| | LG | | | 2.8 ± 1.6 | | | | | 7.1 ± 0.7 | | |
| G1.1601 | DI | 40% | | 92% | | | | | | | |
| | LG | 1.8 ± 1.2 | | 3.2 ± 0.9 | | | | | | | |
| G1.1615 | DI | | | | | 54% | | | | 89% | |
| | LG | | | | | 6.3 ± 2.4 | | | | 5.0 ± 1.8 | |
| IZ2 | DI | | | | | 77% | | | | | |
| | LG | | | | | 4.5 ± 1.9 | | | | | |
| LA2157 | DI | | | | | 16% | | | | 86% | |
| | LG | | | | | 8.3 ± 4.3 | | | | 10 ± 5.3 | |
| LA2172 | DI | | | | | 41% | | | | | |
| | LG | | | | | 6.6 ± 2.4 | | | | | |
| LYC 4/78 | DI | 29% | | 59% | | | | | | | |
| | LG | 4.5 ± 2.9 | | 1.4 ± 1.1 | | | | | | | |
| T566-81 | DI | | | | 44% | 35% | | | | | |
| | LG | | | | 3.3 ± 1.8 | 2.7 ± 1.7 | | | | | |
| MM | DI | | 52% | 95% | 82% | 89% | 88% | 68% | 95% | 84% | 94% |
| | LG | | 5.4 ± 2.0 | 5.4 ± 1.7 | 6.4 ± 1.6 | 7.8 ± 4.1 | 9.2 ± 4.4 | 6.8 ± 3.7 | 6.6 ± 2.1 | 6.4 ± 1.6 | 5.5 ± 1.6 |

1.5. Results

The disease incidence and lesion growth in detached leaf infection experiments were determined over several days for each genotype, usually from 2-4 days post-infection. The disease incidence in *L. esculentum* cv. Moneymaker, which served as a reference, fluctuated between 15 and 78% in these experiments. Table 4 shows the results of 14 genotypes for which detached compound leaves originating from at least 5 individual plants were inoculated, with 40 inoculation spots per leaf (10 per leaflet). The disease incidence in these 14 genotypes should be compared to that in the control line *L. esculentum* cv. Moneymaker determined in the same experiment/week.

Except for genotypes 82/2577 and 83/2896 (both of the species *L. esculentum*), the genotypes tested showed in all experiments a lower disease incidence than Moneymaker. Genotypes G1.1556, G1.1560 and G1.1601 showed a low disease incidence in three independent experiments, ranging from 0 to 21%. Statistical analysis indicated that the disease incidence in genotypes 78/1604, 91/4311, 96/4326, G1.1556, GI 1558, G1.1560, G1.1601, LA716 and LYC 4/78 was significantly lower than in the control line *L. esculentum* cv. Moneymaker (p<0.05). There was, however, a great variation between weeks and some of the differences observed in detached leaf assays may actually not be very robust because of the fluctuations in disease incidence between experiments/weeks (15-78%).

Within these resistant genotypes (with a disease incidence significantly lower than that in the Moneymaker reference), the lesions that expanded successfully often did so at similar rate as in Moneymaker (e.g. 96/4326, G1.1560, LA716). The converse situation was not found: none of the genotypes displayed a disease incidence similar to that of Moneymaker but a lesion growth rate slower than Moneymaker.

Table 4 also presents data on the average growth rates of lesions expanding on each genotype over a 24 h period (between 48 and 72 hpi). Lesion growth rate in most genotypes was in the same range as Moneymaker. Five accessions (91/4311, 160/79, G1.1556, G1.1601 and LYC 4/78) showed a slower lesion growth rate, which was statistically significantly different from that of *L. esculentum* cv. Moneymaker.

The stem segment infection assay (Table 5) appeared to be more robust than the leaf assay in terms of reproducibility between experiments performed in different seasons. Even though the number of data points with stem segments (5-8 segments per plant) is a great deal smaller than with the leaf assay (40 inoculation droplets per compound leaf, one or two leaves could be tested per plant), the variability between experiments was generally lower in the stem segment assay. The disease incidence in the stem assay for the control genotype *L. esculentum* cv. Moneymaker ranged from 52-95%. The disease incidence in 17 genotypes (Table 5) should be compared to the disease incidence of the control line *L. esculentum* cv. Moneymaker determined in the same experiment/week. Most genotypes showed a disease incidence in a similar range as the control line Moneymaker. Genotypes G1.1556 (29% and 41%) and G1.1560 (28% and 7%) showed a reduced disease incidence. Only G1.1560 differed statistically significant (p<0.05) from the control.

The lesion growth rates in the stem assay (Table 5) for the control genotype *L. esculentum* cv. Moneymaker ranged from 5.4 to 9.2 mm/day. The lesion growth rates of many genotypes were in a similar range as the control. However, in accessions 89/3793, G1.1601, LYC 4/78, T566-81, the lesion growth rate was statistically significantly different (p<0.01) from the control cv. Moneymaker.

With a number of genotypes that were rated as partially resistant in the stem segment assay, qualitative assays were performed on whole plants, grown in a glasshouse on Rockwool®. The aim was to evaluate whether genotypes that appeared resistant in stem segments under laboratory conditions indeed were more resistant than control lines in a semi-commercial cropping system. Plants were grown in randomised order in rows of Rockwool®, the glasshouse compartment was filled with citrus fruit heavily infected by *B. cinerea* at point of sporulation. The glasshouse compartment was kept at high humidity by spraying the floor twice a day with tap water and leaving doors and windows closed. At regular intervals pruning wounds were made on all plants and the occurrence of grey mould was monitored over time.

A number of wild *Lycopersicon* accessions were identified that displayed a severe reduction of both parameters, thus providing potential sources for introgressing two, potentially independent mechanisms of partial resistance into *L. esculentum*.

Example 2

QTL-Mapping for Resistance to *Botrytis cinerea* in an Interspecific *Lycopersicon*Cross (*L. esculentum* cv. Moneymaker×*Lycopersicon parviflorum* G1.1601)

2.1. Introduction

A set of *Lycopersicon* accessions from diverse origins was screened for resistance to the fungal pathogen *Botrytis cinerea* as described in Example 1. The accession *Lycopersicon parviflorum* G1.1601 showed in a leaf assay a lower disease incidence and also a slower lesion growth (see Tables 4 and 5 above). A segregating population, consisting of 130 $F_2$-derived $F_3$ populations, originating from a cross between *L. parviflorum* G.1601 and *L. esculentum* cv Moneymaker, was evaluated for resistance to *B. cinerea* in a stem assay.

Amplified Fragment Length Polymorphism markers were used to construct a linkage map and to perform Quantitative Trait Locus-analysis. QTLs were detected for both disease incidence and lesion growth.

2.2. Plant Material

After identification of the resistant accession, *Lycopersicon parviflorum* G1.1601, a segregating population with this accession as founding parent (Huang, 2001), was used for further analysis. The segregating population consisted of 130 $F_2$-derived $F_3$ populations.

2.3. Disease Evaluations

From each of the 130 $F_3$ populations 5 seedlings were grown and subjected to the stem assay described in Example 1 (see 1.4). For practical reasons the complete set of measurements was divided (at random) into 13 portions of equal size. Every week one portion consisting of 50 plants was measured. A large set of susceptible Moneymaker control plants was used to correct for environmental differences between weeks. For practical reasons *L. parviflorum* G1.1601 was not included in the experiment. Measurements were performed as described in Example 1.

Progress of infection was recorded on two time points after inoculation (96 and 120 hours after infection). In this way both disease incidence, which is defined as the percentage of inoculated stem parts that showed disease symptoms at the final moment of observation, and lesion growth, which is defined as the average speed of lesion development across the tomato stem in a 24-hour period, were determined as described in Example 1.

Figure 4:
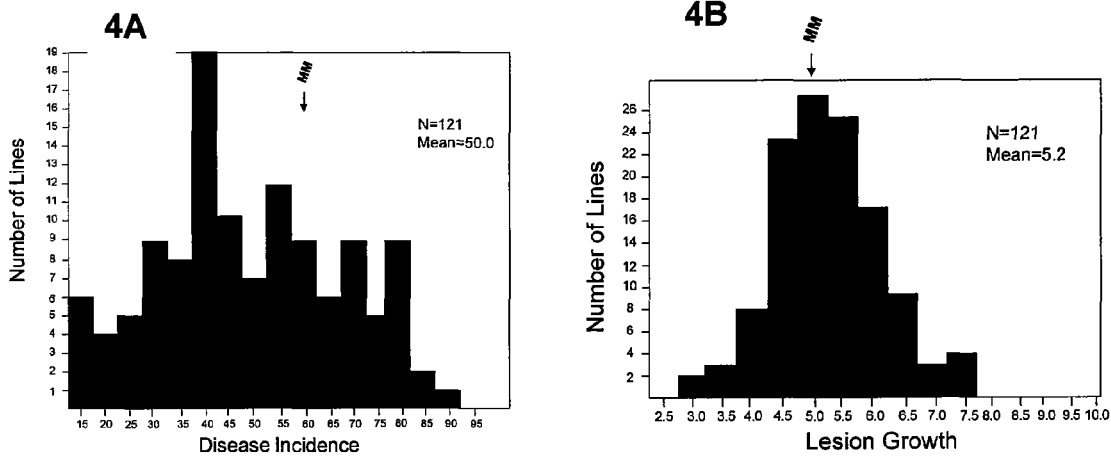
FIG. 4 shows the results of the *L. esculentum* cv. Moneymaker×*L. parviflorum* G1.1601 cross. The segregation in the $F_2$ population (based on average of $F_3$ lines) for disease incidence (FIG. 4A) and lesion growth (FIG. 4B). Disease incidence is on the x-axis as percentage (FIG. 4A) and classes of 5% (12.5-17.5%; 17.5-22.5% and so on. Lesion growth is on the x-axis in mm (FIG. 4B) and classes are 0.5 mm (2.75-3.25; 3.25-3.75 and so on). On the y-axis the number of plants in each class is presented.

The distribution of the measurements is displayed in FIG. 4. The distributions suggest normal, quantitative trait characteristics, therefore suitable for a QTL mapping approach.

2.4. Molecular Markers

No $F_2$ leaf material was available; therefore leaves of twelve $F_3$ plants derived of each of the 130 $F_2$-derived were pooled and used for DNA-isolation. AFLP determinations were performed according to Vos et al. (1995) using a set of 10 Pst/Mse primer combinations.

2.5. Linkage Analysis and QTL Mapping

Due to the dominant nature of the AFLP markers, the paternal (*L. parviflorum*) and maternal (*L. esculentum*) linkage groups were calculated separately.

Marker data were analyzed and a genetic linkage map was calculated using the JoinMap® software package (version 3.0; Plant Research International, Wageningen, The Netherlands). Linkage groups were formed at various log-likelihood (LOD) thresholds. Recombination fractions were converted to map distances using the Kosambi function (Kosambi, 1944). The output from JoinMap® was converted to a graphical format for linkage maps and QTL plots using the program MapChart (Plant Research International). Phenotypic data were analyzed and QTLs were calculated using MapQTL® (version 4.0; Kyazma B. V., Wageningen, The Netherlands) by interval mapping (IM) and multiple QTL mapping (MQM) (Jansen, 1993, 1994). The calculated phenotypic data for the $F_2$ population came from the average values of the disease assay of all plants within an $F_3$ line. An arcsine transformation was used to normalize disease incidence data. QTLs were calculated using the interval mapping algorithm.

For each of the 130 $F_3$ populations the combined data of markers and the disease data were subjected to QTL analysis using MapQTL®. A first round of interval mapping was performed and peaks in the LOD profile were identified. All markers originating from the one or the other parent were directly used to calculate independent linkage maps. In total 192 AFLP markers were placed on the paternal and maternal linkage maps. The male and female linkage maps were individually used for QTL-mapping. Three QTLs were determined (see table 6).

TABLE 6

Summary of QTL mapping results based on non-integrated map.

| QTL in *L. parviflorum* | Region for selection | Max LOD | Infection % (no. of individuals) | Size of lesions |
|---|---|---|---|---|
| QTL for disease incidence (Chrom. 3) | 23 cM | 2.0 | aa* 70% (12) b- 49% (87) | aa 5.7 mm b- 5.1 mm |
| QTL for disease incidence (Chrom. 4) | 28 cM | 2.8 | aa 58% (17) b- 45% (76) | aa 5.9 mm b- 5.1 mm |
| QTL for lesion growth (Chrom. 9) | 25 cM | 2.0 | aa 49% (27) b- 51% (56) | aa 5.8 mm b- 4.9 mm | aa is homozygous *L. esculentum* for the complete chromosomal region.
b- is heterozygous or homozygous *L. parviflorum* for the QTL-region.

The average *Botrytis* resistance of the 11 plants with all three QTL-regions heterozygous or homozygous *L. parviflorum* (b-) reflected a disease incidence of 40% and a lesion growth of 5.0 mm per day. Only one plant was homozygous *L.*

*esculentum* for all three QTL-regions and had a disease incidence of 72% and a lesion growth of 7.2 mm per day. Five plants were homozygous *L. esculentum* for two of the three QTLs and their average disease incidence was 67% combined with a lesion growth of 5.8 mm (data not shown).

This Example shows that genetic sources like *L. parviflorum* G1.1601 can be used to increase the resistance to *B. cinerea* in tomato. Several QTLs both for disease incidence as for lesion growth could be identified (table 6). These QTLs may be confirmed in more advanced breeding material such as backcross lines.

Table 7 shows the experimental results of disease resistance tests of various $F_3$ lines resulting from a cross between *L. esculentum* cv Moneymaker and *L. parviflorum* G.1601. It is clearly shown that the BChirs5 reference line used in this experiment exhibits a higher level of resistance than that of the *L. parviflorum* (L parv) lines listed. However, the presence of QTL effects can also be established for the *parviflorum* QTLs.

Seeds of *Lycopersicon esculentum* cv. Moneymaker (hereafter referred as Moneymaker) were obtained from the seed bank of De Ruiter Seeds cv, Bergschenhoek, The Netherlands.

An interspecific cross between Moneymaker and LYC 4/78 was made to produce $F_1$ seeds. The $F_1$ seeds were grown into $F_1$ plants. $F_2$ seeds, derived from selfing one $F_1$ plant were sown to obtain an $F_2$ population of 174 individuals. A $BC_2$ (backcross 2) population of 59 individuals was generated by two rounds of backcrossing with Moneymaker as the recurrent and female parent. Using MAS, $BC_2$, $BC_3$, and $BC_4$ genotypes were selected containing one of the two identified QTLs and some $BC_2$ were self pollinated to produce $BC_2S_1$ seeds (see FIG. 2). Two $BC_2S_1$ populations were grown: one of 60 $BC_2S_1$ individuals that segregated for the QTL for disease incidence and another one of 47 $BC_2S_1$ individuals that segregated for the QTL for lesion growth.

TABLE 7

Average stem lesion length of *Botrytis cinerea* lesions in adult plants of *L. parviflorum* accession G.1601 three weeks after inoculation.

| Background* | Average stem lesion length (cm) | St. dev. | D.I. (%) | QTL-3p (disease inc.) | QTL-4p (disease inc.) | QTL-9p (lesion growth rate) |
|---|---|---|---|---|---|---|
| Tradiro | 6.9 | 3.6 | 86 | | | |
| Durintha | 8.1 | 1.1 | 100 | | | |
| Moneyberg | 8.1 | 2.1 | 100 | | | |
| GT | 8.2 | 2.0 | 100 | | | |
| BChirs5 | 0.3 | 1.2 | 5 | | | |
| *L. parv* line 1 PV960818 | 5.7 | 2.7 | 88 | + | + | + |
| *L. parv* line 2 92686 (F1) | 3.1 | 2.1 | 57 | n.d. | n.d. | n.d. |
| *L. parv* line 3 PV960890 | 7.0 | 2.6 | 92 | + | + | − |
| *L. parv* line 6 PV960811 | 4.3 | 1.3 | 93 | n.d. | + | + |
| *L. parv* line 7 PV960730 | 4.8 | 2.1 | 93 | + | + | − |
| *L. parv* line 5 PV960860 | 5.9 | 2.2 | 100 | − | − | − |
| *L. parv* line 4 PV960875 | 6.2 | 1.6 | 100 | + | + | − |

*Reference lines are indicated in bold type face: Tradiro is a hybrid, susceptible to *Botrytis* according to growers; Durintha is a hybrid with partial resistance according to growers; Moneyberg and Moneymaker are similar types of susceptible lines; GT is Moneyberg with TMV resistance; BChirs5 is a backcross line resulting from *L. hirsutum* LYC 4/78 introgression and comprises the hirsutum QTL-1h for lesion growth.
(+): heterozygous or homozygous presence;
(−): not present;
n.d.: not determined.

Example 3

Mapping Partial Resistance to *Botrytis cinerea* in an Interspecific Tomato Population (*L. esculentum* cv Moneymaker×*L. hirsutum* Accession LYC 4/78)

In this Example, two QTL loci conferring partial resistance to *B. cinerea* originating from *L. hirsutum* LYC 4/78 are presented. A confirmation of the results was obtained by assessing the resistance level to *B. cinerea* in two $BC_2S_1$ populations segregating for one of the two QTL loci respectively.

3.1. Plant Material

Seeds of *Lycopersicon hirsutum* LYC 4/78 (hereafter referred as LYC 4/78) were obtained from the gene bank located at the Institute for Plant Genetics and Crop Plant Research, Gatersleben, Germany.

3.2. Stem Assay

An inoculum from *B. cinerea* strain B05.10 was prepared according to Benito (1998). The stem assay was performed as described in Example 1.

3.3. DNA Isolation and Marker Analysis

Genomic DNA was isolated from two young (rolled up) leaves using a cetyltrimethylammonium bromide (CTAB) based protocol according to Steward and Via (1993), adjusted for high throughput DNA isolation using one ml micronic tubes (Micronic BV, Lelystad, The Netherlands) and grounded using a Retsch 300 mm shaker at maximum speed (Retsch B V, Ochten, The Netherlands). The AFLP analysis (Vos et al., 1995) of $F_2$, $BC_2$, $BC_3$, $BC_4$ and $BC_2S_1$ populations was done and the AFLP fragments were resolved on a LI-COR 4200 DNA sequencer, essentially following the method published by Myburg (Myburg et al. 2001). The selective Pst primer was labeled with an IRD 700 or IRD 800 fluorescent label. AFLP gel images were scored using the AFLP-Quantar Pro software package (Keygene BV, Wageningen, The Netherlands). The following ten primer combinations and adapter sequences were used for genotyping: P14M48, P14M49, P14M50, P14M60, P14M61, P15M48, P18M50, P18M51, P22M50 and P22M51, as described by Bai et al. (2003).

3.4. Phenotypic Analysis of the $F_2$ Population

Variation in disease incidence between the different *Botrytis* assays was observed (See Example 1, supra). Therefore seven independent consecutive stem disease assays were performed on 172 of the 174 individuals of the $F_2$ population derived from the cross between Moneymaker×LYC 4/78. This resulted in at least five independent evaluations of the disease bioassay for almost each $F_2$ genotype. In each individual disease bioassay six stem segments contributed to the calculation of the lesion growth. The average values for disease incidence and lesion growth for the $F_2$ population showed a normal distribution (data not shown). The average disease incidence for Moneymaker is 59% with a lesion growth of 9.2 mm/day. The average disease incidence in the $F_2$ population ranged between 10% and 97% with a population average of 48%. Lesion growth ranged between 3.3 mm and 11.5 mm/day with an average of 7.8 mm/day.

Average disease incidence of each individual experiment ranged from 31% to 73%, while the average lesion growth ranged from 6.2 to 7.9 mm/day (Table 8). Lesion growth can only be calculated if there is at least infection in one of the six stem pieces. Consequently an increase in the number of informative genotypes for lesion growth could be observed with higher disease incidences. For instance, with the low average disease incidence (31%) only 52% of the genotypes were informative for lesion growth.

TABLE 8

Average disease incidence and average lesion growth of seven experiments according to Example 3.4. The average values of the weeks are ordered according to disease incidence percentage.

| Nr | Average disease incidence (%) | n | Average lesion growth rate (mm/day) | n | % informative plants for lesion growth |
|---|---|---|---|---|---|
| 1 | 40.6 | 172 | 6.4 | 116 | 67.4 |
| 2 | 43.3 | 155 | 7.9 | 117 | 75.5 |
| 3 | 30.9 | 109 | 6.3 | 57 | 52.3 |
| 4 | 54.2 | 51 | 7.2 | 43 | 84.3 |
| 5 | 55.4 | 139 | 7.5 | 111 | 79.9 |
| 6 | 73.9 | 153 | 7.9 | 144 | 94.1 |
| 7 | 37.5 | 140 | 6.6 | 86 | 61.4 |
| Avg | 48.2 | 172 | 7.2 | 172 | 100.0 |

3.5. Molecular Markers & Genetic Linkage Map

A genetic linkage map was calculated for an $F_2$ population (n=174) derived from the cross of Moneymaker×LYC 4/78. Ten primer combinations were used to obtain 218 amplified fragment length polymorphism (AFLP) markers in the $F_2$ population (n=174). A total of 69 markers (31.7%) could be readily scored co-dominantly, thus allowing the calculation of an integrated $F_2$ genetic linkage map. Marker analysis performed on $BC_2$, $BC_3$ and $BC_2S_1$ genotypes allowed the addition of an additional 145 AFLP markers. A total of 102 out of these 145 additional AFLP markers were previously not scored due to complexity of the $F_2$ gels. The overall genetic linkage map consisted of 315 AFLP markers of 14 linkage groups and has a total length of 958 cM. Since co-migrating AFLP markers within a species are generally allele specific, co-linearity with other AFLP linkage maps was used to assign linkage groups to chromosomes. Some Moneymaker specific AFLP markers were in common with the genetic linkage maps as published (Haanstra et al. 1999; Bai et al. 2003) and therefore some linkage groups could be assigned to chromosomes, including the linkage groups harboring the identified QTLs. To improve the linkage map in the QTL intervals, diagnostic CAPS markers were added in these regions based on the published *L. esculentum*×*L. pennellii* map (Tanksley et al. 1992; Haanstra et al. 1999).

3.6. Linkage Analysis and QTL Mapping

Marker data were analyzed and a genetic linkage map was calculated as described in Example 2.

The total length of the $F_2$ linkage map was 958 cM, which is less then other published interspecific *Lycopersicon* maps with genetic lengths ranging from 1200-1400 cM (Foolad et al. 2002; Haanstra et al. 1999; Tanksley et al. 1992). Additional AFLP markers were scored using AFLP marker data obtained from backcross and $BC_2S_1$ populations. Although 46% more markers were placed on the linkage map, the length of the genetic linkage map did not increase. The reason for this is that the used data were obtained from several small sub-families and thus not informative for the calculation of genetic distances, but estimation of the position is possible by visual inspection of the graphical genotypes (Van Berloo, 1999).

3.7. QTL Mapping in the $F_2$ Population

The phenotypical and marker data were used for the identification of QTLs by means of interval mapping (IM, see Example 2). IM was both applied to data obtained from individual replicates and to the average values of the replicates.

Disease Incidence

Interval mapping for disease incidence in the $F_2$ population was done for those individual disease tests with an average disease incidence lower than 50% and for average data obtained from all disease tests (table 8). The average data of all tests gave in the interval mapping procedure a single significant QTL for disease incidence (likelihood of odds (LOD) score must be higher than 3.4 for a genome-wide confidence level of P<0.05). This QTL had a LOD score of 4.5 and explained 13% of the total phenotypic variation (Table 9). The allele contributing to resistance originated from the resistant parent LYC 4/78. QTL mapping on each individual experiment gave in all four cases the same QTL region. In each independent experiment occasionally other "minor QTLs" were observed.

Lesion Growth

Lesion growth can best be measured in those disease tests with a high disease incidence. For QTL mapping the average of all 7 disease tests was used and one QTL for lesion growth of *B. cinerea* was identified above the threshold (LOD 3.4 for a genome-wide confidence level of P<0.05). This QTL had a LOD score of 4.2 and explained 12% of the total phenotypic variation (Table 9). The positive effect originated from the resistant parent LYC 4/78. The necessity of performing multiple disease tests is illustrated because in only one single repetition a LOD profile above the threshold was found.

TABLE 9

Estimation of the calculated effects for plants homozygous Moneymaker (A), heterozygous (H) or homozygous LYC 4/78 (B). Scores for the $F_2$ population were calculated with the interval mapping procedure, while scores for the $BC_2S_1$ population were calculated with a Kruskal-Wallis analysis.

| Chromosome | Pop | LOD | A | H | B | % Expl |
|---|---|---|---|---|---|---|
| 1 (Lesion growth) | $F_2$ | 4.2 | 8.8 | 7.8 | 7.1 | 11.9 |
| | $BC_2S_1$ | | 6.2 | 5.2 | 4.9 | ND[a] |

TABLE 9-continued

Estimation of the calculated effects for plants homozygous Moneymaker (A), heterozygous (H) or homozygous LYC 4/78 (B). Scores for the $F_2$ population were calculated with the interval mapping procedure, while scores for the $BC_2S_1$ population were calculated with a Kruskal-Wallis analysis.

| Chromosome | Pop | LOD | A | H | B | % Expl |
|---|---|---|---|---|---|---|
| 2 (Disease incidence) | $F_2$ | 4.5 | 63.4 | 47.1 | 43.5 | 13.0 |
| | $BC_2S_1$ | | 77.0 | 72.3 | 59.9 | ND |

$^a$ND = Not determined 3.8. Confirmation of QTLs in a Bioassay

Figure 2:
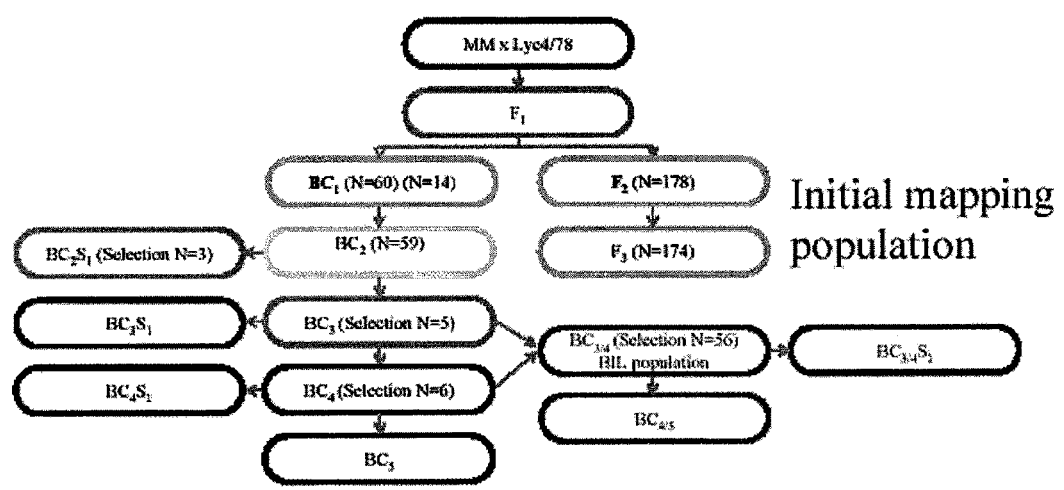
FIG. 2 shows a schematic overview of the development of the *L. esculentum*×*L. hirsutum* LYC 4/78 populations. $BC_4$ lines are backcrossed to *L. esculentum* cv. Moneymaker to obtain $BC_5$ lines to aid in the development of QTL-NIL lines for the two main effects, which were identified in the $F_2$ population. $BC_3$ and $BC_4$ lines are backcrossed to *L. esculentum* cv. Moneymaker to obtain a backcross inbred line (BIL) population (See Example 3).
Figure 3:
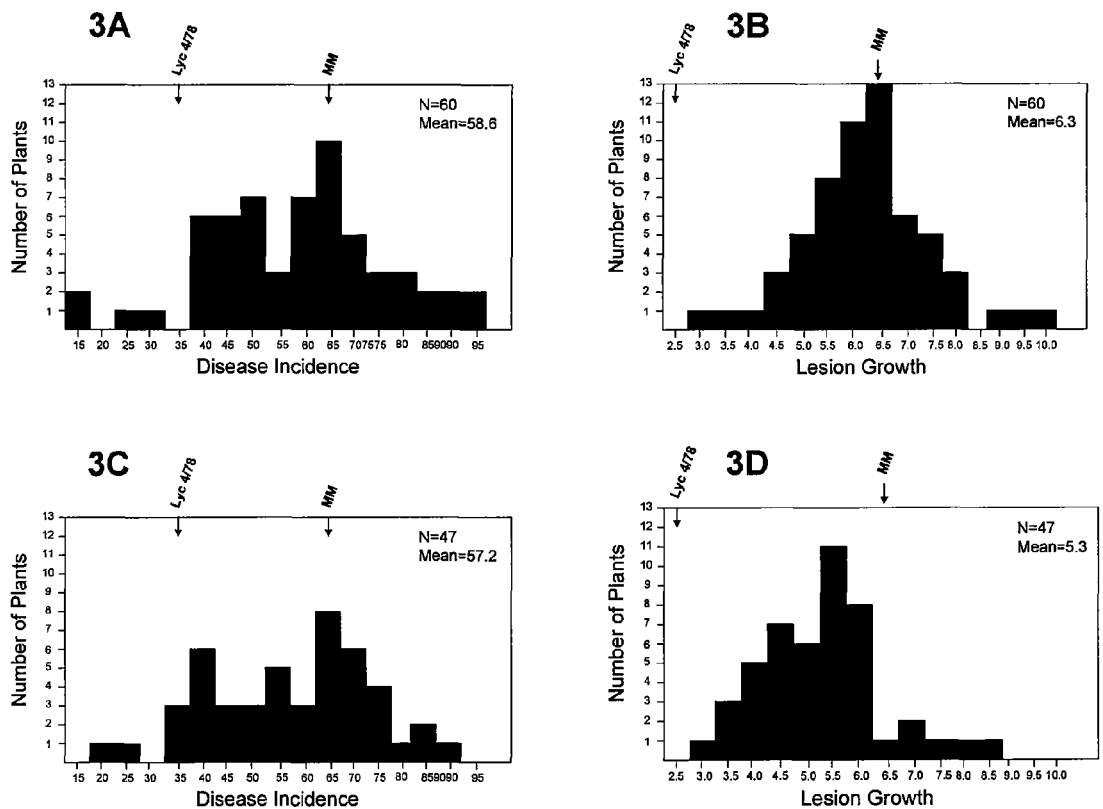
FIG. 3 shows the segregation in the two $BC_2S_1$ populations (population size 60 resp. 47) segregating for lesion growth (FIGS. 3B and 3D) and disease incidence (FIGS. 3A and 3C). Lesion growth is on the x-axis in mm (FIGS. 3B and 3D) and classes are 0.5 mm (2.75-3.25; 3.25-3.75 and so on) and disease incidence (FIGS. 3A and 3C) is in classes of 5% (12.5-17.5%; 17.5-22.5% and so on). On the y-axis is the number of plants in each class. The average parental values are indicated by the arrows for MM resp. Lyc 4/78.

The $F_1$ plant of the cross Moneymaker×LYC 4/78 was twice backcrossed with Moneymaker and the 59 progeny plants were screened for the presence of the two identified QTL-regions (one for disease incidence and one for lesion growth) using AFLP markers. Plants, heterozygous for one of the two identified QTLs, were selected and selfed to obtain two $BC_2S_1$ populations. A total of four disease bioassays were performed with each $BC_2S_1$ genotype. The data of both $BC_2S_1$ subpopulations, analyzed with SPSS, showed normal distributions for lesion growth, but not for disease incidence as some subclasses were observed (FIG. 2).

All $BC_2S_1$ plants were AFLP genotyped with the same 10 primer combinations as described for the $F_2$ population in section 3.3 above. The average lesion growth in the population segregating for the lesion growth locus was 5.3 mm/day while in the other population an average lesion growth of 6.3 mm/day was observed. Not a single plant had a lesion growth as low as the resistant parent LYC 4/78. For disease incidence, however, plants with a lower disease incidence then the resistant parent LYC 4/78 were observed. The average disease incidence for both $BC_2S_1$ populations was equal (57-59%).

The positive effect of each QTL was confirmed in the $BC_2S_1$ populations. The QTL for disease incidence decreased the chance of infection with 17% (46% of the parental variation) and the QTL for lesion growth reduced fungal growth with 1.3 mm/day (33% of the parental variation).

A comparison with data obtained from the $F_2$ population is presented in Table 8. Only a part of the variation could be explained by the effect of both QTLs. Some additional ("minor") QTL loci were identified.

During analysis of data of disease tests obtained from both $F_2$ and $BC_2S_1$ genotypes, one major QTL for disease incidence was identified (QTL-2h). Besides this QTL, other "putative" QTL loci for disease incidence were identified. Using this information cofactors were selected to perform a restricted 'multiple QTL mapping' (MQM) procedure on the $F_2$ dataset. In this analysis, one additional "minor" QTL loci for disease incidence was identified (QTL-4h). A QTL is denoted as "minor" when its score is below the significance threshold of LOD 3.4. The effects however are believed to be real QTL effects.

QTL-4h is located on chromosome 4 and reduces disease incidence (see table 1). The QTL has a LOD score of 2.9 and is coupled to the following AFLP markers: P18M51-169.5e, P18M51-305.4h, P14M60-262.9e, and P14M61-292.7h. The positive effect of this locus is derived from the resistant parent L. hirsutum. The positive effect was identified both in the $F_2$ and in the $BC_2S_1$ population. This QTL was initially identified in the $BC_2S_1$ population lacking segregation of QTL-2h and is also coupled to the AFLP markers P14M48-345e, P14M48-177e, and P18M50-147e. Segregation of co-dominant CAPS makers for this region was assessed in both $BC_2S_1$ populations and the $F_2$ population for loci located on both Chromosome 2 and Chromosome 4. The CAPS marker on Chromosome 2, AT4G30930, is tightly linked to the QTL on Chromosome 2 while for Chromosome 4 segregation data for a set of 10 CAPS markers equally distributed over this chromosome were analysed. ANOVA analysis, including the CAPS marker AT4G30930 and the CAPS marker TG609 on Chromosome 4 showed that CAPS marker TG609 is significantly linked to the trait disease incidence.

To verify the effect of each "minor" QTLs, near isogenic lines (NIL) for the regions containing the QTL effect may be developed. In parallel thereto, a backcross inbred line (BIL) population of L. hirsutum LYC 4/78 in a L. esculentum cv. Moneymaker genetic background may be developed.

3.9 Conclusions of Disease Assay and QTL Mapping

The bioassay for measuring resistance to B. cinerea has proven to be a valuable tool. However, a still large and unknown variation appears to influence the development of the infection process. This large non-genetic variation can be minimized by using standardized procedures and by performing many independent replications. The variation can be caused by the greenhouse conditions changing from week to week (day length, hours of sunlight and temperature) causing differences in physiological conditions of the stem. Also, small variations in the preparation of the fungal inoculum may play a role in the variation of the infection process. Another observation is that the development of the disease can also be affected by the microclimate in the trays in which the stem pieces were placed. Ten different experimental trays were used for the $BC_2S_1$ bioassays. Statistical analysis was used to compensate for variation between and within experiments. Experiments with the highest average disease incidence were the most informative for measuring lesion growth while experiments with a more moderate disease incidence were more informative. Disease incidence and lesion growth are independent traits, since no linear correlation between the two traits could be observed.

Quantitative trait loci for resistance against B. cinerea in tomato were identified in the $F_2$. These identified QTLs were confirmed in $BC_2S_1$ populations and explained 46% and 33% of the parental variation for disease incidence and lesion growth, respectively. These results suggest that not all QTLs conferring resistance to B. cinerea were detected in the original $F_2$ mapping population. In both $BC_2S_1$ populations plants were found with higher resistance levels as the resistant parent LYC 4/78. This is indicative for the presence of additional resistance loci segregating in the $BC_2S_1$ population. An additional segregation of resistance was surprising because it may have been expected that already large parts of the genome of the two $BC_2S_1$ populations were homozygous Moneymaker.

3.10 Confirmation of Effect of Individual QTLs in Greenhouse Conditions

Plants containing either of the QTLs described above were placed in an L. esculentum background using the method described in FIG. 2. $BC_2S_2$ lines were placed in the greenhouse in soil and grown under standard practice conditions in the Netherlands. After 3 months plants were inoculated by placing an agar disc containing Botrytis in a wound in the main stem. The wound was subsequently closed using Parafilm®. Three weeks after inoculation stem lesion length was measured (in cm) (For more details see below). Results are listed in Table 10. Clearly, lines containing the QTL for lesion growth show an extreme reduction in lesion size.

TABLE 10

Average stem lesion length of *Botrytis cinerea* lesions in adult plants of *L. hirsutum* accession LYC 4/78 and *L. hirsutum* LA 1777, three weeks after inoculation.

| Line | Repeat | Average stem lesion length (cm) | St. dev. | Background | Comments/QTL |
|---|---|---|---|---|---|
| 21 | a*** | 4.2 | 1.1 | GT | Susceptible control |
| 21 | b | 3.6 | 0.9 | GT | Susceptible control |
| 22 | a | 3.0 | 0.0 | Durintha | Partially resistant control |
| 22 | b | 5.0 | 2.9 | Durintha | Partially resistant control |
| 23 | a | 5.6 | 3.0 | Tradiro | Susceptible control |
| 23 | b | 6.0 | 3.3 | Tradiro | Susceptible control |
| 26 | a | 3.2 | 0.8 | BChirs3 | QTL-2h |
| 26 | b | 2.6 | 0.9 | BChirs3 | QTL-2h |
| 26 | c | 2.6 | 1.3 | BChirs3 | QTL-2h |
| 26 | d | 3.2 | 2.2 | BChirs3 | QTL-2h |
| 28 | a | 2.6 | 0.5 | BChirs5 | QTL-1h |
| 28 | b | 2.0 | 0.0 | BChirs5 | QTL-1h |
| 28 | c | 2.0 | 0.0 | BChirs5 | QTL-1h |
| 28 | d | 2.0 | 0.0 | BChirs5 | QTL-1h |
| 373 | e | 4.3 | 0.6 | LA 1777 | QTL-10 containing source of WO02/085105 |
| 373 | f | 4.3 | 0.2 | LA 1777 | QTL-10 containing source of WO02/085105 |
| 374 | e | 4.8 | 0.6 | BC chrs 10 | Introgr. line from *L. esculentum* × LA 1777 |
| 374 | f | 4.5 | 0.0 | BC chrs 10 | Introgr. line from *L. esculentum* × LA 1777 |
| 375 | e | 4.2 | 0.3 | BC chrs 10 | Introgr. line from *L. esculentum* × LA 1777 |
| 375 | f | 4.2 | 0.2 | BC chrs 10 | Introgr. line from *L. esculentum* × LA 1777 |
| 376 | e | 4.3 | 0.3 | BC chrs 10 | Introgr. line from *L. esculentum* × LA 1777 |
| 376 | f | 5.0 | 0.7 | BC chrs 10 | Introgr. line from *L. esculentum* × LA 1777 |
| 377 | e | 4.2 | 0.3 | BC chrs 10 | Introgr. line from *L. esculentum* × LA 1777 |
| 377 | f | 4.3 | 0.2 | BC chrs 10 | Introgr. line from *L. esculentum* × LA 1777 |
| 378 | e | 4.8 | 0.2 | BC chrs 10 | Introgr. line from *L. esculentum* × LA 1777 |
| 378 | f | 4.6 | 0.4 | BC chrs 10 | Introgr. line from *L. esculentum* × LA 1777 |
| 68 | e | 2.0 | 0.0 | parv1 | QTL-3p + QTL-4p |
| 68 | f | 2.0 | 0.0 | parv1 | QTL-3p + QTL-4p |
| 78 | e | 2.0 | 0.0 | parv2 | QTL-9p + QTL-4p |
| 78 | f | 2.0 | 0.0 | parv2 | QTL-9p + QTL-4p |

***a, b, c and d are repeats whereby each repeat represents 5 plants; e and f are repeats whereby each repeat represents 3 plants;
GT is Moneyberg with TMV resistance;
Durintha is a hybrid with partial resistance according to growers;
Tradiro is a hybrid, susceptible to *Botrytis* according to growers;
BChirs indicates backcross lines resulting from *L. hirsutum* LYC 4/78 introgressions;
LA 1777 is wild species accession L. hirsutum LA 1777;
BC chrs 10 indicates backcross lines with introgression at chromosome 10 from *L. hirsutum* LA 1777;
parv indicates lines resulting from *L. parviflorum* introgressions.

3.11. The Level of Resistance to *Botrytis* Conferred by *L. hirsutum* LYC 4/78 QTLs is Higher than the Level of Resistance Conferred by *L. peruvianum* LA 1777 QTLs at Chromosome 10.

The level of resistance in plants containing the *L. hirsutum* LYC 4/78 QTLs described herein was compared to that of *L. hirsutum* LA1777, the source of WO 02/085105 that contains a QTL for partial *Biotrytis* resistance on chromosome 10, and to introgression lines derived therefrom with introgressions at chromosome 10.

Lines were placed in the greenhouse in soil and grown under standard practice conditions in the Netherlands. After 3 months plants were inoculated by placing an 0.5 cm×0.5 cm agar disc containing *Botrytis* in a vertical stem wound of 2 cm length in the main stem. The wound was subsequently closed using Parafilm®. Three weeks after inoculation stem lesion length (length of discolored tissue dotted with fungal growth) was measured (in cm) from top of the lesion to the bottom of the lesion. Results are listed in Table 10. It was observed that lines containing the QTLs from *L. hirsutum* LYC 4/78 showed a higher level of resistance to *Botrytis* than the LA 1777 source and IL-lines. Additionally, *L. parviflorum* lines containing the combination of either the QTL for disease incidence on chromosome 4 and that of lesion growth on chromosome 9 (line 68), or the combination of both QTLs for disease incidence on chromosome 3 and chromosome 4 (line 78) were compared to the LA 1777 source and IL-lines. Former lines showed less lesion growth on the stem and therefore exhibit a higher level of resistance to *Botrytis* then the lines derived from LA 1777 (See Table 10). Where a lesion length of 2.0 cm is recorded, only the original wound could be measured and no fungal growth was observed, which indicates a high level of resistance. Thus, a stem lesion length of 2 cm indicates absence of net growth.

Marker Sequences as Used Herein.

The following Tables provide detailed information on the various RFLP and COS-II markers as indicated in the various linkage maps and as indicated for association with the QTLs of the present invention. The information was directly copied in from the SOL Genomic Network (SGN) database hosted at Cornell University, version of 7 Oct. 2005.

TABLE 11

TG301    RFLP marker

RFLP Information
Name: TG301
Insert size: 750
Vector: pGEM4Z
Cutting Site: PST1
Drug Resistance: AMP Forward sequence
(SEQ ID NO: 1)
TTGTAACTTACTAAATTAAGAGCTCAGGATGAACAGAACACGAATTATTA
GTTCATATTAAGCAAGAAACTTAAAAAACTTCACCTTCTC CAACATACTCTACAACAAACTCTTTTGTCTTGATATCTTCATCTGCCACA
ATCCCAGTGCCACATTTCTCAGTCTGCACGTTATGAGTCA ACAAAACTTTAGTTTTTTAGATGATTATTGCTTGGTTTTCAAAAGAAACG
AAAATAAGAAGAATACAAAATAACCAACATTTCTTTACTT CTTCACCAGATACACAACTGAATTAAATGCAAAAATAGATATGAAAAATG
TTACCAGCCTGCACTTTTGATGCAGATTGTACTTGTTTGC AATTGAAAAGTGTCGAATGGTCATTTTTGGTAAAAACTGATGAATGTGGT
ATTTTGAGAAAGGATTTATGACGGTCCTTTTGCTTAATTA

TCCCTCTTATAAACGTTAGTAAAGGC

Reverse sequence
(SEQ ID NO: 2)
TATTCTGAATCTGGAAAATTGTTCTGCCAATTTCTTTGACCAACCAGACA
ATACCCTTTTAATCTAAGACCCTAATTACAAGGTTACTGA CAATCACTTTTGACACCAATGTCTTTGATAAAGCACTGTTAAAATTTTCA
GATGTGCTTTAATACTCTGCATCCTTTTTAGGAACTCTTT TGTCTACTTTCACTTTTTAAAAGAAAGAACTTAAGGAGAGGACATACTTA
TTATTTTTGCATTTTCTATATCAAGTAAAGTGAGAAGACT TCCATTAATTTGCATCCAGCGGATGCTAATGGCTACAACATAGCTACTTT
AAGCAAATAGGTGATTTGATCAAGATTCTTTACGTTTTCA AGATCACAGCAACAAAAAGGGTTCCTTAAAAACCTAGCCTTTACTAACGT
TTATAAGAGGGATAATTAAGCAAAAGGACCGTCATAAATC

CTTTCTCAAAATACCACATTCATCAGTTTTTACCA

TABLE 12

TG460    RFLP marker

RFLP Information
Name: TG460
Insert size: 2000
Vector: pGEM4Z
Cutting Site: PST1
Drug Resistance: AMP Forward sequence
(SEQ ID NO: 3)
CCTTAGTTTTGAAATCTTTAAGTAGCAATTAGTAATCGGTAGCTCTCCAG
TATGAAAAGTTCATAATCACTTGGTGGATCTCTTATTATT TGCATCATTTGTGTGCAATAGGCATAAGAGGTAGTCATTTCACAATGCCT
CTGAAATGTGTGCATTGACATTTGAGAACACTTGAGGATG GGATACACTCTCTGTCATCAGGAACTACTTAGGTGACAAATAGATGTGAA
GATTCACGGCATAGTGTCTTTTGATCCATATCATAACCAG AAAGTGAGTATCCCCATTTCTCACATTAGCTATATGAAGGAAGAAAGGGA
ACAAAGGAAAAGCGCTACCCTTATTCGTCGAAAGCTAGC CTTCATGATAAACCAAATGAAATTAGAAAAATTTAAGAACTTTGCTATAG
CTTCAAAGAATCTTTTAGATTCTTGTTTACAAAGTTTTG

CTGATCTTTCTTACAT

TABLE 12-continued

Reverse sequence
(SEQ ID NO: 4)
TTATGATGCTCAAAATTTCTTATTTTAGACAGACTCGAAATGTGACTATT
CCAGAGAAAAATAAACAAGATCCCTCGGGACACTGAACCT GAGAACAGGTTCAAATTCCCTACTGTACCCCAACAGACAAAGGGAAGAGA
GAGCTATCAGTTTCTCTTTGGTTTGAGAAAAAACATAATA GTATGGAGTGTACCAGATGCTTCAGGATTTCAGACATGTTCTGACTTGTT
ACCTAATGTATTTGATTTCATAGTATAAATCTTAGGTGTT CTGCTTGACTAGAAGTATGGAAAGTCATTCTTGTCAGTAGTCAGTCTTGA
GATATAAGATATAATTTGATATACATCTAAATAGATCTTG GATTCATTAGATAAGTTCAACAAGCATGGGTCAATAAGCACATTGATCAA
TTACAGGATGTAGAATAACTTTGCTTATTGTGAAATCCTC

AAAAATGAATGATGCAGGCAAGAAGTGCAAATTACC

TABLE 13

TG55    RFLP Marker

RFLP Information
Name: TG55
Insert size: 1800
Vector: pUC
Cutting Site: PST1
Drug Resistance: AMP Forward sequence
(SEQ ID NO: 5)
TGGATTCAGTGTGAAGAAAGGGGACATGGTGAGTTACCTACCATATGCAA
TGGGAAGAATGAAATTTATATGGGGCGATGATGCAGAAGA ATATACACCGGAGAGATGGCTTGATGGGACGGTTTCTTCAGGCAATACA
ATCCCTTCAAATTTACAGCTTTCCAGGGTGTTTTGAAGCT CATCATAAGCTTTGATTATCATTTTGTTAAAGCCTTGAACGCAAGTCTAT
ACTTAACTTGCCTAGAGCTATGTACTGTCGACATATGATC AATTAACTAAGCACATTCTTTTGTTAATAAAACAGGCAGGGCCAAGGATT
TGCTTGGGAAAGGAGTTTGCTTATAGGCAAATGAAGATAT TCTCTGCTGTTTTATTACATCACTTCGTTTTCAAGCTGAGTGATGACAAC
AAGGCTACCAACTACAGGACAATGATTACTCTTCACATTG

ATGGGGGATT

Reverse sequence
(SEQ ID NO: 6)
GATCCAAAATATGCTTTTCTGATGACCCTTACCAGATGGATTCAGTGTGA
AGAAAGGGGACATGGTGAGTTACCTACCATATGCAATGGG AAGAATGAAATTTATATGGGGTGATGATGCAGAAGAATATAAACCGGAGA
GATGGCTTGATGGGACGGTTTCTTCAGGCAAGAGAATCC CTTCAAATTTACAGCTTTCCAGGTTGTTTTAAAGCTCATCATAAGCTTTG
ATTATCATTTTGTTAAAGCCTTGAACGCGAGTCTATACTT AACTTGCCTAGTGCTATGTACTGTCGTCATATGATCAATTAACTAAGCAC
ATTCTTTTGTTAATAAAACAGGCAGGGCAAGGATTTGCT TGGGAAGGAGTTTGCTTATAGGCAAATGAAGATATTCTCTGCTGTTTTA
TTACATCACTTTGTTTTCAAGTTGAGTGATGACAACAAGG

CTACCAACTACAGGACAATGATTACTCTTCACATTGATGGGGGATTGCAT
GTTCGTGTCTTTAGTA

TABLE 14

TG59     RFLP Marker

RFLP Information
Name: TG59
Insert size: 3500
Vector: pUC
Cutting Site: PST1
Drug Resistance: AMP Forward sequence
(SEQ ID NO: 7)
TCGACCTGCAGATATTTCATAAAAGAATGCCCCCTGAAGCAGTTGATTTG
GTGTCGAGGCTTCTCCAATATTCTCCAACTCTACGCTGCA CTGCTGTAAGTAAAAAGTTTTCTTCTCAATTATCAAGTATTTAGGATATT
CTGGTAGTTTCCCATTTTACCCATCATTCAAACATGGTGT TCCATTTTTGTTATGTTTCAATATGCGAGTTCTCATTGATTGTCCTTTTA
GCACTTCTGTTTTCCGGGGATATTGAGAACATTTTGTGTT TATTGACAGTTGGAAGCATGTGCACACCCTTTCTTTGATTCTTTAAGGGA
ACCAAATGCTTGCTTGCCAAATGGGCGACCTCTGCCTCCC

CTATTCAACTTTTCACCTCAAGGTGAGCTTCAGTCTAGCTTTCTCCTTTT
ATTTCACATGATTTGATACGTCAAT

Reverse sequence
(SEQ ID NO: 8)
AGTTGGGAATTATATCCTGTTCAGTAGACAAATTACCCAACCAGAATATA
CGTACCTGAATGTCTATGTGATAGATAAGTCCATACTAGT ACTTCTGTCTTGTGAATATCTGTGTGTTGCCTTGTGAGTAAGGATATTCA
TTGCTCCAATGCAAAACCATTATGTCATTGTCTTAGGGAG CTTTCTGTTGTTTGTATGGCATGAAAAGTTAATCCTAAAAGAAAGGTAAA
GTAAAGGTGCATCCTAGGTTAGTATAATGTTCTGAAGGCA AAGATGTTTTTCTTTTGATTTAAACTTATGTTTTTTTTTCTTTGATTCCG
TCTCCTTCCCTAATAGCAAAACTGGGAAGTTGAAACTAC GTTATAACTGGACAACCTCATAAATGAAAAAGATGGTAAATAATGCCATT
TCTGGGGTGGGGTAATTTTCCTTAGATGAGTGTGATACTG

TTGTACCTGTTGCTTGAACTCCTAAGTTTCCTCATTTTCTTCCTTTTTGT
TTATGCTAAATGCCGTGTGTACTGTG

TABLE 15

TG145     RFLP Marker

RFLP Information
Name: TG145
Insert size: 2480
Vector: pGEM4Z
Cutting Site: PST1
Drug Resistance: AMP Forward sequence
(SEQ ID NO: 9)
ATGGGCTATGCTTGGTGCTCTTGGATGTGTCTTCCCTGAGCTATTGGCCC
GTAATGGTGTCAAGTTCGGTGAGGCTGTGTGGTTCAAGGC TGGATCCCAGATCTTCAGCGAGGGTGGACTTGATTACTTGGGCAACCCAA
GCTTGGTCCATGCACAAAGCATCTTGGCCATCTGGGCTTG CCAAGTTGTGTTGATGGGAGCCGTTGAGGGATACCGCATTGCTGGTGGAC
CTCTTGGTGAGGTTGTCGACCCACTCTACCCCGGTGGCAG CTTCGACCCATTAGGCCTTGCTGAAGACCCGGAGGCATTTGCTGAGCTTA
AGGTTAAGGAGATCAAGAACGGACGACTTGCTATGTTCTC

TATGTTTGGGTTCTTTGTTCAGGCCATTGTTACCGGAAAGGGTCCATTGG
AGAACCTCGCTGACCACCTT

TABLE 15-continued

Reverse sequence
(SEQ ID NO: 10)
GGAGACAACCTTGCATGCCAGCAGTGGATCACCTCGAGTCCACGGTTCTT
GGCAAAGGTTTCTGGATCTGCTGAAAGTCCAGCGGTGTCC CACCCGTAGTCACCAGGGAATTCACCATTCAAGTAGCTAGGGGACTCACC
AGAGAATGGACCCAAGTACTTAACACGGTCAGGGCCATAC CATGGGCTGCTAGATGGGGCTGACTTTGCGACAGCCTTTCTCATAGTGAT
CCTTCCATTTCCTGTGATTTCTGAGGCAGATGGTAAGAGT TTCACTGCTTGTCCAGCAAAAGAAGGGGAAGAAAGAGCCATTGTAGCAGC
TGCCATGGTGTTTATATCAAGAGAAATGTAAGTGTTTGAT GGTATGAGATATTGTTGAAGTTGGCTGTAATGAGATGAAGTTACAAGGAA
TTAATTCACCATATATATAGGGAGTAATTAAGAGGGAAAG

AGTCCAAATTATCTAATGATATCTATATCTA

TABLE 16

CT128     RFLP Marker

RFLP Information
Name: CT128
Insert size: 700
Vector: pBLUESC
Cutting Site: EcoR1
Drug Resistance: AMP Forward sequence
(SEQ ID NO: 11)
CTTTTTTTTTTTTCAACACAAACAAAATTTCATTATATTGTCAGGTAGC
ACACTACATCTTTACACTGTCATCAAACGACCAGAGACTT GAGAACGTTTTAAGAGATTCATTTTCCGGGGACAAAGTTTGTGGCGAAAG
CCCAGGCATTGTTGTTTACGGGGTCTGCAAGGTGGTCAGC AAGGTTCTCCAATGGACCCTTTCCGGTGACAATAGCTTGAACAAAGAATC
CAAACATAGAGAACATAGCAAGTCTACCGTTCTTGATCTC CTTTACCTTGAGCTCAGCAAATGCCTCTGGGTCTTCAGCAAGGCCTAATG
GGTCGAAGCTGCCACCAGGGTAGAGTGGGTCGACAACCTC ACCAAGAGGTCCACCAGCAATACGGTATCCCTCAACAGCTCCCATCAACA
CAACTTGGCAAGCCCAGATGGCCAAGATGCTTTGTGCATG

GACCAAGCTTGGGTTGCCCAAGTAGTCAA

Reverse sequence
(SEQ ID NO: 12)
CTGGTGATTACGGGTGGGATACCGCTGGACTTTCAGCAGACCCTGAAACT
TTTGCCAAGAACCGTGAACTTGAGGTGATCCACTGCAGAT GGGCTATGCTTGGTGCTCTTGGATGTGTCTTCCCTGAGCTCTTGGCCCGT
AATGGTGTCAAGTTCGGTGAGGCTGTGTGGTTCAAGGCCG GATCCCAGATCTTCAGTGAAGGTGGACTTGACTACTTGGGCAACCCAAGC
TTGGTCCATGCACAAAGCATCTTGGCCATCTGGGCTTGCC AAGTTGTGTTGATGGGAGCTGTTGAGGGATACCGTATTGCTGGTGGGACC
TCTTGGTGAGGTTGTCGACCCACTCTACCCTGGTGGCAGC TTCGACCCATTAGGCCTTGCTGAAGACCCAGAGGCATTTGCTGAGCTCAA
GGTAAAGGAGATCAAGAACGGTAGACTTGCTATGTTCTCT

ATGTTTGGATTCTTTGTTCAAGCTATTGTCACCGGAAAGGGTCCA

TABLE 17

C2_At4g30930    COS-II marker

Mapping experiments
  Map: Tomato-EXPEN 2000

Forward primer (5'-3'):
ATCATACCTTCTCTCTCCAAACCC    (SEQ ID NO: 13)

Reverse primer (5'-3'):
TCGCCATTGCTCACTTTAAACTG    (SEQ ID NO: 14)

Temperature: 55° C.
$Mg^{+2}$ concentration: 1.5 mM

PCR Product Sizes
    LA716: 700
    LA925: 700

Digested band sizes (using DpnII)
    LA716: 380 + 220
    LA925: 340 + 220

| Mapped locations | | | |
|---|---|---|---|
| Map | Chromosome | Offset | Confidence |
| Tomato-EXPEN 2000 | 2 | 63.5 | I |

TABLE 18

C2_At2g18030    COS-II marker

Mapping experiments
Map: Tomato-EXPEN 2000

Forward primer (5'-3'):
(SEQ ID NO: 15)
TTGGGCGACCACGCTGAATC

Reverse primer (5'-3'):
(SEQ ID NO: 16)
TTACCCACATCAGGACCTTGCC

Temperature: 55° C.

$Mg^{+2}$ concentration: 1.5 mM

PCR Product Sizes
LA716: 1300
LA925: 1200

Digested band sizes (using amplicon difference)
LA716: 1300
LA925: 1200

| Mapped locations | | | |
|---|---|---|---|
| Map | Chromosome | Offset | Confidence |
| Tomato-EXPEN 2000 | 2 | 83.1 | I |

TABLE 19

C2_At5g64670    COS-II marker

Mapping experiments
Map: Tomato-EXPEN 2000

Forward primer (5'-3'):
(SEQ ID NO: 17)
TGATAAATGCTGGGAAGATTGACTC

Reverse primer (5'-3'):
(SEQ ID NO: 18)
ATCAACCTGGCTCCATCTTCTATTTG

Temperature: 55° C.
$Mg^{+2}$ concentration: 1.5 mM

PCR Product Sizes
LA716: 200
LA925: 220

Digested band sizes (using amplicon difference)
LA716: 200
LA925: 220

| Mapped locations | | | |
|---|---|---|---|
| Map | Chromosome | Offset | Confidence |
| Tomato-EXPEN 2000 | 2 | 76 | CF(LOD3) |

TABLE 20

TG609    RFLP Marker

RFLP Information
Name: TG609
Insert size: 1900
Vector: pGEM4Z
Cutting Site: PST1
Drug Resistance: AMP Forward sequence
(SEQ ID NO: 19)
GAGACAGCTTGCATGCCTGCAGAGGTGATAAATTCACCAAGGTTTCATAT
TTAGGAAACAAGAAAATTAAAAGATCATTAACACAGATGA AAGGATATGACTAGGAGGCAATGACTGATCTTTGACTATCAAATACTTCT
CAGGGAAACAATGTGAATGGGCTTTTACATGCAGAGATAT TGATTGTGATCATGTTGAAGAACTTAGGAAACATGAAATTAAATGATCAT
TAACACTGATGCAAGGATATGCCAAGTAGGCAAGCAAATT AAGGTTGAACATAAATGTCTGTGATCTTTGACTATCAAATATCTTCTCAG
AAAAAAAAATGTGAATGCTCATTTACATGCAGAGATGGCT ATTGTGATCATGTGGCTCAGCCTTGAGTCTATATTGAGGTGCAGACAACA
TAGTCCCTAACCACATGTGTGATCAAGCAACTTTTTTGAT

GTCCACAGGGTTATAAGTAGGCAACATTTAAGCAAGAAAAAACACAGGAT
CACTATTGAGTCAGCTGCTGTTGCCTGT

Reverse sequence
(SEQ ID NO: 20)
GGAGACAAGCTTGCATGCCTGCAGAGGTGATAAATTCACCAAGGTTTCAT
ATTTAGGAAACAAGAAAATTAAAAGATCATTAACACAGAT GAAAGGATATGACTAGTAGGCAATGACTGATCTTTGACTATCAAATACTT
CTCAGGGAAACAATGTGAATGGGCTTTTACATGCAGAGAT ATTGATTGTGATCATGTTGAAGAACTTAGGAAACATGAAATTAAATGATC
ATTAACACTGATGCAAGGATATGCCAAGTAGGCAAGCAAA TTAAGGTTGAACATAAATGTCTGTGATCTTTGACTATCAAATATCTTCTC
AGAAAAAAAAATGTGAATGCTCATTTACATGCAGAGATGG

TABLE 20-continued

CTATTGTGATCATGTGGCTCAGCCTTGAGTCTATATTGAGGTGCAGACAA
CATAGTCCCTAACCACATGTGTGATCAAGCAACTTTTTTG

ATGTCCACAGGTTTATAAGTAGGCAACATTTAAGCAAGAAAAAACACAGG
ATCACTATTGAGTCAGCTGCTGTTGCCTGTTACTGAG

TABLE 21

TG62 RFLP Marker

RFLP Information
Name: TG62
Insert size: 1800
Vector: pUC
Cutting Site: PST1
Drug Resistance: AMP Forward sequence
(SEQ ID NO: 21)
CAAAATGCTTCAGCTACTGGCTAAATGAAGTATGTTCTCAACATATTCAC
AAGCTTCTGTCTTCGAAGCTCAAGAAGTGTCGGTATTATC TGAATTAAATAGTAAAGCAAAGAGATGGTTTTATGTTTCTTAAGCAGCAT
TTCTTAGCTTAACGGCCCTCCAGATATATGGTGGACAAAA TAGAATCCATTAGATATAACAAATGGGATTAGTATAATGATCTTTTACTT
TGTTAGATGATCATACTAACGATTGCAAGTTAATCATAT CCAACATATTCTGTAGATATTTCACATTGGCTAGCATGAGGAAAGGTCAT
GTAGGAAATTGAATAGAGTTCAATTTTGGGAAAAGTTGCA TTGAAGAAGGTAACTTCAACAAACGTGTGAAAAAATCACATTTGAGTTGC
CCGCTCACCATCGTGATTCCAGTACGAACTACTCAAAAAT

TTACTTTTGAGCCTTAAACATCATTTTAAGCCTTGAAAAGCTGCTTTTGA
AAAGATCTAAGCAAGAT

Reverse sequence
(SEQ ID NO: 22)
GGAGAATATTGTCACTCTATCAGATAGTTCAAAACTATCGGAGAATGAAA
TGGTCAATTCTTCTCACAAGATATTCATGCCTAGTTGCAG TGTCCGAATTAACATAACATGCTCAATTTTCATATCTTGCAGCAAAATTT
ATCATTGAAACTCTCTGAGATGGAAACAGAGAACAAAGAC CATATTGGAAAGCTTCAATCAGACATGCAGAAAAAGGAAGATGAGATTCA
TGTTTTACGCAAGGAAATTGACAATTACACGGAAACAGTG GATTCACTGGAGAAGCATGTTACAGAGATTAACAATAAATTGGAGGAGAA
AGATCAGCTTGTTCAGGAACTTCAGGACAAGGAGAAGCAG TTGGAAGCTGACAGAGAAAGGTTTTTACTACGGATACTTTTAGTTCTAC
AAATTCTATTATAACCAATACAATGTGTTCAAGTGACTAG TGTTTTGCACCTTGTTGCAGATTCAGGCATCTTTGCTTGCTGCTGAAAGC
AAGCTCACAGAATCCAAAAAGCAGTATGATCAGATGT

TABLE 22

TG555 RFLP Marker

RFLP Information
Name: TG555
Insert size: 1600
Vector: pGEM4Z
Cutting Site: PST1
Drug Resistance: AMP Forward sequence
(SEQ ID NO: 23)
AATTCGGAGCTCACTGCTTCTAATCCTCAGTGAGACTTATTTTCTACATA
TTAAACAATAAGAAATTTACGAAGGAATATTATAGACTGA ATTCCTTGGTGACAAGTATCAAGACATCTTGACCAAGTTTAAAGTTTTGT
AGTGGCAGTTCTTTTAAGCTTTACTTGTGTGAGGTAGACA

TABLE 22-continued

TCAAGGAAGATAAGTAGCAGCTACTCTTCACGGAGCAGCCCATAGGACAC
TCAAATTCACTATTGCGAGGGTCAATCTACCAATTTATGG

AACGATACCAGTAAAGTCATTTTTATGTAAACATCAGACAGCTTTTGACT
AAGCAGAGACATGAATAAGTTCTATTTGTTAGAAGTCGAA

GAGACAAATAAGTTAATTTCACCTATGCTATAAAAGAGGACTCTTATAGT
TATAAATACAGTACATTTTATTAAGGGTTCTAATTGTTGA

CTATGATAGCAAGCATGCCGTACTAATT

Reverse sequence
(SEQ ID NO: 24)
ACATTTTGAGGAAGACAGGAGTTATGTATCGCCATCTGGTGTGCTCCAAG
AACATGACAGATATAAAAGACCGCGGGGTGCACCAGAGAA ATGTTGCATTGGAGCATATTGAACATCATAGGCTCAATGGAATTGTTTAC
TTTGCAGATGATGATAATATCTACTCACTTGAGTTGTTTG AGAGCATTAGATCGATCAAGTAAGTTGAGATTCATCAGTCTTGTTTACAT
GACTTGTCTTTGTTTTGTCCTGCTGTGAGCATGTTCAGGA TGATGTTATGTGCTTTATGTAGATGTTCAAGTCGATAATAGTGAATAGTC
TAGAGCTATTTCACATATATTACAACTTCACTAACAAATT CTTTTCCTGGTGTCCTCGGTTCATCACTCTTCATAGTTATAAGAATAACA
GTTGTAGATTAGACCACTGGTCGTGTGATTTTTGGACTTA

ATTATTATCTCAATTCTTCCTCAAAATAGCAGTCCTTAGATTAGAAGCTG
AGG

TABLE 23

CT50 RFLP Marker

RFLP Information
Name: CT50
Insert size: 1600
Vector: pBLUESC
Cutting Site: EcoR1
Drug Resistance: AMP Forward sequence
(SEQ ID NO: 25)
CTTTTTTTTTTTTTTTATATATTGTGGTATAGATTATTATATAATAACAA
GGTGAATTAACATGAGAAATGAATAATTGTCACATTCTTG TTCTGTCCATTTTCCAGTAGCGGCTAGTTGGAAAATTTGTTGTAACATGT
AACACAGGCTGTCCACATTCTACTCCAGAGAGAAAGTTGG TAAGTAGTGGGGGCAAAAGATAGAGACCCCAATAGCTATCAATTCACTTT
GTTGACAATCAAGATTTGAGAAAAAAGATCAAAACTTTAC CAACTTAGATAGCTCCATAATCAACTGTAGGTACAATTCTTTAGTGAAAT
TGCGGCGTTCATCTTCTGGGGACGAAGAGTAAGTAGACAA TCAATTGTCTTGTAGAACTTGGGCTTTACCATTTTCCCTAGGACATAAGC
TCTTGATCGAAGCTTGAAGTTTAATTTTAGTGGCACTGGT

AATG

Reverse sequence
(SEQ ID NO: 26)
TTTTTTTTTTTTTTAGCCAAAATGCATACAAAAACTGATTCAGAAGATA
CGAGCTTGGCTCCTTCGTCGCCGGACAATAGAGGGCCGAC GGCGTATTACGTTCAGAGTCCGTCACGTGATTCTCACGATGGCGAGAAGA
CAACGACGTCGTTTCACTCTACTCCTGTTATCAGTCCCAT GGGTTCTCCTCCTCACTCTCACTCATCCGTCGGCCGTCACTCCCGTGATT
CCTCTTCCTCCAGATTCTCCGGCTCCCTCAAGCCTGGATC

TABLE 23-continued

TCAGAAGATTTTACCCGACGCCGCCGGAGGCGTCGGCGGCCGTCACCACC
GCAAAGGGCAGAAGCCCTGGAAGGAATGTGATGTTATTTG

AGGAAGAAGGACTACTTGAAGATGATAGATCCAGTAAATCTCTTCCACGT
CGTTGCTATGTCCTTGCTTTTTGTTGTTGGTTTCTTCGTC

CTTTTCTCCTTCTTTGCTCTCATCCTTTGGGGTGCTAGTCGACCTC

TABLE 24

C2_At1g74970    COS-II marker

Mapping experiments
Map: Tomato-EXPEN 2000

Forward primer (5'-3'):
                                    (SEQ ID NO: 27)
TCATCATCAACTATCGTGATGCTAAG Reverse primer (5'-3'):
                                    (SEQ ID NO: 28)
ACGCTTGCGAGCCTTCTTGAGAC Temperature: 55° C.
$Mg^{+2}$ concentration: 1.5 mM PCR Product Sizes
LA716: 1000
LA925: 1000

Digested band sizes (using AluI)
LA716: 550
LA925: 850

Mapped locations

| Map | Chromosome | Offset | Confidence |
|---|---|---|---|
| Tomato-EXPEN 2000 | 4 | 109.7 | I |

TABLE 25

CT128    RFLP marker

RFLP Information
Name: CT128
Insert size: 700
Vector: pBLUESC
Cutting Site: EcoR1
Drug Resistance: AMP Forward sequence
                                    (SEQ ID NO: 11)
CTTTTTTTTTTTTCAACACAAACAAAATTTCATTATATTGTCAGGTAGC
ACACTACATCTTTACACTGTCATCAAACGACCAGAGACTT GAGAACGTTTTAAGAGATTCATTTTCCGGGGACAAAGTTTGTGGCGAAAG
CCCAGGCATTGTTGTTTACGGGGTCTGCAAGGTGGTCAGC AAGGTTCTCCAATGGACCCTTTCCGGTGACAATAGCTTGAACAAAGAATC
CAAACATAGAGAACATAGCAAGTCTACCGTTCTTGATCTC CTTTACCTTGAGCTCAGCAAATGCCTCTGGGTCTTCAGCAAGGCCTAATG
GGTCGAAGCTGCCACCAGGGTAGAGTGGGTCGACAACCTC ACCAAGAGGTCCACCAGCAATACGGTATCCCTCAACAGCTCCCATCAACA
CAACTTGGCAAGCCCAGATGGCCAAGATGCTTTGTGCATG

GACCAAGCTTGGGTTGCCCAAGTAGTCAA

TABLE 25-continued

Reverse sequence
                                    (SEQ ID NO: 12)
CTGGTGATTACGGGTGGGATACCGCTGGACTTTCAGCAGACCCTGAAACT
TTTGCCAAGAACCGTGAACTTGAGGTGATCCACTGCAGAT GGGCTATGCTTGGTGCTCTTGGATGTGTCTTCCCTGAGCTCTTGGCCCGT
AATGGTGTCAAGTTCGGTGAGGCTGTGTGGTTCAAGGCCG GATCCCAGATCTTCAGTGAAGGTGGACTTGACTACTTGGGCAACCCAAGC
TTGGTCCATGCACAAAGCATCTTGGCCATCTGGGCTTGCC AAGTTGTGTTGATGGGAGCTGTTGAGGGATACCGTATTGCTGGTGGGACC
TCTTGGTGAGGTTGTCGACCCACTCTACCCTGGTGGCAGC TTCGACCCATTAGGCCTTGCTGAAGACCCAGAGGCATTTGCTGAGCTCAA
GGTAAAGGAGATCAAGAACGGTAGACTTGCTATGTTCTCT

ATGTTTGGATTCTTTGTTCAAGCTATTGTCACCGGAAAGGGTCCA

TABLE 26

TG599    RFLP marker

RFLP Information
Name: TG599
Insert size: 700
Vector: pGEM4Z
Cutting Site: PST1
Drug Resistance: AMP Forward sequence
                                    (SEQ ID NO: 29)
TGCTTTGAGACAGATGTCTCTCATTAAGTGACTGAAGCTTTCTTCTAGTT
GGCTAGCATATTCATTTTCAGCATATAATCTGTATCATGA ACAAAATTGCGACAGTATTGAATTTTTATTGTTGAATAGTCTTTTTATTA
TCCCCGAAGTTGAGGGTGGAACTTACATTTTCTGTTGATC CTTGCTTGCTGTTTTTGTAAACAAAAAAGCGTCACCCATTATTTTTCTTT
TATTCTTTCTAGGTTGGGACTAAGATTTTTTGAAATGAGA AAGGTATTCGCTACCTTGAGGGCTGTGGTTGAAGTGATGGAGTATCTGAG
CAAAGATGCAGCTCCTGATGGTGTGGGAAGGCTTATAAAG GAGGAGGGAGTATTTCCTTTCATTCTTTGTATTTCCGTGTGTGTATAGT
CCGGAACTGGTTCCCTACTTATGAATTCTTTCATGGTTTG

GTCAATTGAGAAGGATCAAGAAATCTGATGCTACTTTATCATGGGAACTT

Reverse sequence
                                    (SEQ ID NO: 30)
GCTTGCATGCCTGCAGAGTGGTCATACAATAAAAGGTAAAAATCAACATT
CTTACCTCTGGAAAGAAACCAATAGCATTGGTCAATGATG CTGCCTCTAGAGGAACAATATTGTATGGTGCAAGTTCCCCTGATAAAGTA
GCATCAGATTTCTTGATCCTTCTCAACTGACCAAACCATG AAAGAATTCATAAGTAGGGAACCAGTTCCGGACTATACACACACGGAAAT
ACAAAGAAATGAAAGGAAATACTACCTCCTCCTTTATAAG CCTTCCCACACCATCAGGAGCTGCATCTTTGCTCAGATACTCCATCACTT
CAACCACAGCCCTCAAGGTAGCGAATACCTTTCTCATTTC AAAAAATCTTAGTCCCAACCTAGAAAGAATAAAAGAAAAATAATGGGTGA
CGCTTTTTTGTTTACAAAAACAGCAAGCAAGGATCAACAG

AAAATCTAAGTTCCACCCTCAACTTCGGGGATAATAAAAAGACTATTCAA
CAATAAAAATTCAATACTGTCGCAA

TABLE 27

TG10    RFLP marker

RFLP Information
Name: TG10
Insert size: 900
Vector: pUC
Cutting Site: EcoR1/HindIII
Drug Resistance: AMP Forward sequence
(SEQ ID NO: 31)
AACTCTGCTCTGCCAATAGTAGTCAGGCAGATCAAGATGCTCAAAATTTT
CTATTTGAATTGGAAGCATCAAGATGGTTCTTAGCATTTA TTTTAGAAAGACTAACCATATTATCAAATAACCAGACTGAGACGCACACA
AAAGTTTCCCTCTATTATTTTTATAATGATGTGAAGATGC TACATAATGAGTACACTTTGCCTTACTTTACTGCAGATGGACCTACCAGG
CCCAAACGGACATGTAGCTATGACAGAAGAGCAACCGCTA TGAATGTCTCAAACTGTTGGCCTAGGCGATCAGCACAGATGATGAATCTG
GAAGTACATTCCAAGAAGGAAAGCTGGAGCGTGGGAACTA ACCAGATGCAGGGGATGAATCCACACCTTTCAGTTGATCATCTGAAGGGA
AAACTAAGAATTTTCATGAGAAAATGACTGGCTATTTTCA

ACTTTG

Reverse sequence
(SEQ ID NO: 32)
TTCAATGCATTTAAGCTCAAAAAAACAAAGCTGTAGGAAGGAGCATATTA
GTAGCCTAACTCTGCTCTGCCAATAATAGTTAAGCAGATC AAGATGCTCAAAATTTTCTAATTGAATTGTTAGCATCAAGATGCTTCTTA
GCATTTATTTTAGAAAGATTAACCATATTATCAAATAACC AGACAGAGACGCACACAAAAGTTTCAATCTATTATTTTTATAATGATGTG
AAAATGCTACATAATGAGTACACTTTCCCTTACTTTACTG CAGATGGACCTACCAGGCCCAAACGGTCATGTAGTTATGACAGAAGAACA
ACAGTATGAATTTCTCAAACTGTTGGCCAAGGTGATCAGC AAAGATTATGAATTTGGAAGTACATTCCAAGAGGAAAGCTGGAGCATCGT
AACTAACCAGATGCAGGGGATGAATCCACACCTTTCAGTT GATCATCTGAAGGCAAAACTAAGAATTTTCATGAGAAAATACTGGTTATT
TTCAACTTTGTTGGCCAGACGAGGAGTCCAATGGGATAGA

AGGACTAACTCAATGACGTATG

TABLE 28

TM2a    TM marker

TM Information
Name: TM2A
Old COS ID: T0899

Sequence
(SEQ ID NO: 33)
CNAGCTCGANNNACCCTCACTAAAGGGAACAAAAGCTGGAGCTCCACCGC
GGTGGCGGCCGCTCTAGAACTAGTGGATCCCCCGGGCTGCAGGCTCCTCC ATTGAAAAGGGAATCAAGTTTGCCAAAGAAAACTAAAAAAACAAAATTAT
GGTCTAGTTTTCTATAGTGACAGTTTTGGATCTTTTTGGGTCAATTGTTT TTGTATCCTTTGCAAGTTTCTTGCAGCCGGAGGCTTAGATTTAGCTCTTT
TGATATTATACCCAACATTTCTACAAAATAATGTATGGCAAACTGGGGGC CTATCCCATTTGCCTTAGTGTGGAGGTGTTATTCTCACATGAATCGTTTT
CCAATTATGGTTAGTAGCAGACAATTGATGCAAAATGAAGAAATGTTCAT

GACCAAAAAAAAAAAAAAAAA

TABLE 28-continued

| Mapped locations | | | |
|---|---|---|---|
| Map | Chromosome | Offset | Confidence |
| Tomato-EXPEN 2000 (TM2A) | 9 | 50.5 | I |

TABLE 29

TG551    RFLP marker

RFLP Information
Name: TG551
Insert size: 950
Vector: pGEM4Z
Cutting Site: PST1
Drug Resistance: AMP Forward sequence
(SEQ ID NO: 34)
AATGAAGTTCAGTTGATAAGCTAAATGGTGGAAATACTAATTTTAATTGA
CAGTAACTTTGCATTTCAAGGTCCATACCAAAACATTTGC TAACACCAGTTGCTTTGTCAACGAAAACCTTGGCACTCAAAACCCTACCA
AAAGGCTGAAATGCATTTGCAAGCTCTTGATCACCAAATT CTTGAGGAATATGGTAAATAAATAGATTAGCACCAGGTGGACCTGTAAAC
AGCAAAATCGTTTTTGATAAGTACAGGTTTATTTCTACAT GTTCAACTACCACTGCCAAGTACACTAGTTCAAGTGACATCTCCACCACT
TAATTGCATAAAGCTTTACCAACGACAAATATAACAAACT TGTGCAAGTAATTTGAGTTCCTGTCTATACAGTCCAGAATCTCCATATGC
TGCTCATCTCACAATGTTGGTTAAGGAAATTTGTCAAGTA

AAGTTCAA

Reverse sequence
(SEQ ID NO: 35)
CATCTTCAAGTGTCAGCTCAAGTACAGGGGGTCAGGTTGAAGGTTGTTGA
ACATTTATTTTGTGACCTTTTTAGCTCTAGAATTTCTGTA GCTAATCAAGTACAGTCCCATAACCTAGGGGCTGTTAGGGTTTTCTGCTG
AATGAGGCTGCTTGTCTTTATTTTGGTTAATTATTTTCTG GAAATTGTTCCTCGTCATAGAGAATAGAAGTAGAAGAAGAAGAAGATAGT
ATAATCTATTATATTTGTTTTTTACTTAATTTATAAAGAT TCCATAAATGCATGTGATCTTTGATCAATGATATCTTATACAAGTGTATC
ACTAGAATCTATTATATTTGGATTTACTTATTTTATATAG

GATTTCATAAACGCATGTGATC

Bai Y L, Huang C C, van der Hulst R, Meijer Dekens F, Bonnema G, Lindhout P (2003) "QTLs for tomato powdery mildew resistance (*Oidium lycopersici*) in *Lycopersicon parviflorum* G1.1601 co-localize with two qualitative powdery mildew resistance genes," *Mol. Plant Microbe Interactions*, 16:169-176.

Benito E P, ten Have A, van't Klooster J W, van Kan J A L (1998) "Fungal and plant gene expression during synchronized infection of tomato leaves by *Botrytis cinerea*," *Eur. J. Plant Pathol.*, 104:207-220.

Bernacchi D, Tanksley S D (1997) "An interspecific backcross of *Lycopersicon esculentum*×*L. hirsutum*: Linkage analysis and a QTL study of sexual compatibility factors and floral traits," *Genetics*, 147:861-877.

Christou P, Murphy J E, and Swain W F (1987) "Stable transformation of soybean by electroporation and root formation from transformed callus," *Proc. Natl. Acad. Sci. USA*, 84:3962-3966.

Churchill G A, Doerge R W (1994) "Empirical threshold values for Quantitative trait mapping," *Genetics*, 138: 963-971.

Deshayes A, Herrera-Estrella L, Caboche M (1985) "Liposome-mediated transformation of tobacco mesophyll protoplasts by an *Escherichia coli* plasmid," *EMBO J.*, 4:2731-2737.

D'Halluin K, Bonne E, Bossut M, De Beuckeleer M, Leemans J (1992) *Plant. Cell*, 4:1495-1505.

Dik A J, Koning G, Kohl J (1999) "Evaluation of microbial antagonists for biological control of *Botrytis cinerea* stem infection in cucumber and tomato," *Eur. J. Plant Pathol.*, 105:115-122.

Doganlar S, Frary A, Ku H M and Tanksley S D (2002) "Mapping Quantitative Trait Loci in Inbred Backcross Lines of *Lycopersicon pimpinellifolium* (LA1589)," *Genome*, 45:1189-1202.

Draper J, Davey M R, Freeman J P, Cocking E C and Cox B J (1982) "Ti plasmid homologous sequences present in tissues from *Agrobacterium* plasmid-transformed *Petunia* protoplasts," *Plant and Cell Physiol.*, 23:451-458.

Eckstein F (ed.) (1991) *Oligonucleotides and Analogues, A Practical Approach*, Oxford Univ. Press, NY 1991.

Egashira H, Kuwashima A, Ishiguro H, Fukushima K, Kaya T, Imanishi S (2000) "Screening of wild accessions resistant to gray mold (*Botrytis cinerea* Pers.) in *Lycopersicon*," *Acta Physiologiae Plantarum*, 22:324-326.

Foolad M R, Zhang L P, Khan A A, Nino Liu D, Liln G Y (2002) "Identification of QTLs for early blight (*Alternaria solani*) resistance in tomato using backcross populations of a *Lycopersicon esculentum×L. hirsutum* cross," *Theor. Appl. Genetics*, 104:945-958.

Fulton T, van der Hoeven R, Eannetta N, Tanksley S (2002) "Identification, Analysis and Utilization of a Conserved Ortholog Set (COS) Markers for Comparative Genomics in Higher Plants," *The Plant Cell*, 14(7): 1457-1467.

Godoy G, Steadman J R, Dickman M B, Dam R (1990) "Use of mutants to demonstrate the role of oxalic acid in pathogenicity of *Sclerotinia sclerotiorum* on *Phaseolus vulgaris*," *Physiological Molecular Plant Pathology*, 37, 179-191.

Grandillo S, Tanksley S D (1996) "QTL analysis of horticultural traits differentiating the cultivated tomato from the closely related species *Lycopersicon pimpinellifolium*," *Theor. Appl. Genet.*, 92: 935-951.

Gruber M Y, Crosby W L (1993) Vectors for Plant Transformation. In: Glick B R and Thompson J E (Eds.) *Methods in Plant Molecular Biology & Biotechnology*, CRC Press, pp. 89-119.

Haanstra J P W, Wye C, Verbakel H, Meijer Dekens F, van den Berg P, Odinot P, van Heusden A W, Tanksley S, Lindhout P, Peleman J (1999) "An integrated high density RFLP-AFLP map of tomato based on two *Lycopersicon esculentum×L. pennellii* $F_2$ populations," *Theor. Appl. Genetics*, 99:254-271.

Hain R, Stabel P, Czernilofsky A P, Steinbliss H H, Herrera-Estrella L, Schell J (1985) "Uptake, integration, expression and genetic transmission of a selectable chimaeric gene to plant protoplasts," *Mol. Gen. Genet.*, 199:161-168.

Horsch R B, Fry J E, Hoffman N L, Eichholts D, Rogers S G, Fraley R T (1985) "A simple method for transferring genes into plants," *Science*, 227:1229-1231.

Jansen R C (1993) "Interval Mapping of Multiple Quantitative Trait Loci," *Genetics*, 135:205-211.

Jansen R C (1994) "Controlling the Type I and Type II Errors in Mapping Quantitative Trait Loci," *Genetics*, 138:871-881.

Kado C I (1991) "Molecular mechanisms of crown gall tumorigenesis," *Crit. Rev. Plant Sci.*, 10:1-32.

Klein T M, Gradziel T, Fromm M E, Sanford J C (1988). "Factors influencing gene delivery into zea mays cells by high velocity microprojectiles," *Biotechnology*, 6:559-563.

Klein T M, Arentzen R, Lewis P A, and Fitzpatrick-McElligott S (1992) "Transformation of microbes, plants and animals by particle bombardment," *Bio/Technology*, 10:286-291.

Kosambi D D (1944) "The estimation of map distances from recombination values," *Ann. Eugen.*, 12:172-175.

Laursen C M, Krzyzek R A, Flick C E, Anderson P C, Spencer T M (1994) "Production of fertile transgenic maize by electroporation of suspension culture cells," *Plant Mol. Biol,.* 24(1):51-61.

Miki B L, Fobert P F, Charest P J, Iyer V N (1993) "Procedures for Introducing Foreign DNA into Plants." In: Glick B R and Thompson J E (Eds.) *Methods in Plant Molecular Biology & Biotechnology*, CRC Press, pp. 67-88.

Moloney M M, Walker J M, Sharma K K (1989) "High efficiency transformation of *Brassica napus* using *Agrobacterium* vectors," *Plant Cell Reports*, 8:238-242.

Myburg A A, Remington D L, O'Malley D M, Sederoff R R, Whetten R W (2001) "High-throughput AFLP analysis using infrared dye-labeled primers and an automated DNA sequencer," *Biotechniques*, 30:348-357.

Nesbitt T C, Tanksley S D (2001) "fw2.2 directly affects the size of developing tomato fruit, with secondary effects on fruit number and photosynthate distribution," *Plant Physiol.*, 127:575-583.

Nicot P C, Moretti A, Romiti C, Bardin M, Caranta C, Ferriere H (2002) "Differences in susceptibility of pruning wounds and leaves to infection by *Botrytis cinerea* among wild tomato accessions," *TGC Report*, 52:24-26.

Paterson A H (ed.) (1996) *Genome Mapping in Plants*, Academic Press Inc San Diego, Calif., USA.

Phillips R L, Somers D A, Hibberd K A. (1988) "Cell/tissue culture and in vitro manipulation." In: G. F. Sprague & J. W. Dudley, eds. *Corn and corn improvement*, 3rd ed., pp. 345-387. Madison, Wis., USA, American Society of Agronomy.

Pierik R L M (1999) *In vitro Culture of Higher Plants*, 4th edition, 360 pages, ISBN: 0-7923-5267-X.

Prins T W, Tudzynski P, von Tiedemann A, Tudzynski B, ten Have A, Hansen M E, Tenberge K, van Kan J A L (2000) "Infection strategies of *Botrytis cinerea* and related necrotrophic pathogens." In *Fungal Pathology* (J. Kronstad, editor). Kluwer Academic Publishers, pp. 33-64.

Roupe van der Voort J N A M, van Zandvoort P, van Eck H J, Folkertsma R T, Hutten R C B, Draaistra J, Gommers F J, Jacobsen E, Helder J, Bakker J (1997) "Use of allele specificity of comigrating AFLP markers to align genetic maps from different potato genotypes," *Mol. Gen. Genetics*, 255: 438-447.

Sambrook J, and Russell D W (2001) *Molecular Cloning: A Laboratory Manual*, New York, N.Y., USA., Cold Spring Harbor Laboratory Press.

Sanford J C, Klein T M, Wolf E D, Allen N (1987) "Delivery of substances into cells and tissues using a particle bombardment process," *J. Particulate Sci. Technol.*, 5:27-37.

Sanford J C (1988) "The biolistic process," *Trends in Biotechnology*, 6:299-302.

Sanford J C (1990) "Biolistic plant transformation," *Physiologica Plantarum*, 79:206-209.

Sanford J C, Smith F D, and Russell J A (1993) "Optimizing the biolistic process for different biological applications," *Methods in Enzymology*, 217:483-509.

Steward C N, Via L E (1993) "A rapid CTAB DNA isolation technique useful for RAPD fingerprinting and other PCR applications," *Biotechniques,* 14:748-750.

Tanksley S D, Ganal M W, Prince J P, de Vicente M C, Bonierbale M W, Broun P, Fulton T M, Giovannoni J J, Grandillo S, Martin G B (1992) "High density molecular linkage maps of the tomato and potato genomes," *Genetics,* 132:1141-1160.

Tanksley S D, Grandillo S, Fulton T M, Zamir D, Eshed Y, Petiard V, Lopez J and Beck-Bunn T (1996) "Advanced backcross QTL analysis in a cross between an elite processing line of tomato and its wild relative *L. pimpinellifolium,*" *Theor. Appl. Genet.,* 92:213-224.

Tanksley S D, Young N D, Paterson A H, Bonierbale M W (1998) "RFLP mapping in plant breeding: New tools for an old science," *Bio/Technology,* 7:257-263.

Tijssen P (1993) "Hybridization With Nucleic Acid Probes. Part I. Theory and Nucleic Acid Preparation." In: *Laboratory Techniques in Biochemistry and Molecular Biology.* Elsevier.

Urbasch I (1986) "Resistenz verschiedener Kultur- und Wildtomatenpflanzen (*Lycopersicon* spp.) gegenüber *Botrytis cinerea* Pers," *J. Phytopathol.,* 116:344-351

Utkhede R, Bogdanoff C, MeNevin J (2001) "Effects of biological and chemical treatments on *Botrytis* stem canker and fruit yield of tomato under greenhouse conditions," *Can. J. Plant Pathol.,* 23:253-259.

Utkhede R S, Mathur S (2002) "Biological control of stem canker of greenhouse tomatoes caused by *Botrytis cinerea,*" *Can. J. Microbiol.,* 48:550-554.

Van Berloo R (1999) "GGT: Software for the display of graphical genotypes," *J. Heredity* 90:328-329.

Van Berloo R, Aalbers H, Werkman A, Niks R E (2001) "Resistance QTL confirmed through development of QTL-NILs for barley leaf rust resistance," *Mol. Breeding,* 8:187-195.

Van Heusden A W, Koornneef M, Voorrips R E, Bruggemann W, Pet G, Vrielink van Ginkel R, Chen X, Lindhout P (1999) "Three QTLs from *Lycopersicon peruvianum* confer a high level of resistance to *Clavibacter michiganensis* ssp *michiganensis,*" *Theor. Appl. Genetics,* 99:1068-1074.

Voorrips R E (2002) "MapChart: software for the graphical presentation of linkage maps and QTLs," *J. Heredity,* 93:77-78.

Vos P, Hogers R, Bleeker M, Reijans M, van de Lee T, Hornes M, Frijters A, Pot J, Peleman J, Kuiper M (1995) "AFLP: a new technique for DNA fingerprinting," *Nucl. Acids Res.,* 23:4407-4414.

Zhang L, Cheng L, Xu N, Zhao M, Li C, Yuan J, and Jia S (1991) "Efficient transformation of tobacco by ultrasonication," *Biotechnology,* 9:996-997.

---

What is claimed is:

1. A *Botrytis*-resistant tomato plant, comprising at least one quantitative trait locus (QTL) associated with *Botrytis* resistance of *Lycopersicon hirsutum* LYC 4/78, said QTL being a member selected from the group consisting of QTL-1h, QTL-2h, and QTL-4h; wherein said QTL of *Lycopersicon hirsutum* LYC 4/78 is not in the natural genetic background of the *Botrytis*-resistant tomato plant, wherein said QTL-1h is indicated by at least one AFLP marker linked to said QTL on chromosome 1, wherein said marker is selected from the group consisting of the AFLP fragments P22M50-412h, P14M50-349h, P14M60-69h, P14M49-192h, P14M49-232h, P14M49-260e, P14M50-503h, P18M50-124h, and P14M49-114h;

wherein said QTL-2h is indicated by at least one AFLP marker-linked to said-QTL on chromosome 2, wherein said marker is selected from the group consisting of the AFLP fragments P14M60-537h, P15M48-257e, P14M49-327h, P14M49-325h, P14M61-286e, P14M61-125h, and P18M51-134h;

wherein said QTL-4h is indicated by at lease one AFLP marker linked to said QTL on chromosome 4, wherein said marker is selected from the group consisting of the AFLP fragments P18M51-169.5e, P18M51-305.4h, P14M60-262.9e, P 14M61-292.7h, TG609, P 14M48-345e, P 14M48-177e, P 18M50-147e.

2. The plant according to claim 1, further comprising at least one quantitative trait locus (QTL) associated with *Botrytis* resistance of *Lycopersicon parviflorum* G1.1601 said QTL being a member of selected from the group consisting of QTL-3p, QTL-4p, and QTL-9p of Table 2, and wherein said QTL of *Lycopersicon parviflorum* G1.1601 is not in the natural genetic background of the *Botrytis*-resistant tomato plant.

3. A method of producing a *Botrytis*-resistant tomato plant comprising the step of transferring a nucleic acid comprising at least one QTL associated with *Botrytis*-resistance in tomato, from a *Botrytis*-resistant donor tomato plant to a *Botrytis*-susceptible recipient tomato plant, wherein said transfer of said nucleic acid is performed by transformation, by crossing, by protoplast fusion, by a doubled haploid technique or by embryo rescue, wherein said at least one QTL is selected from the group consisting of QTL-1h, QTL-2h, and QTL-4h; wherein said QTL-1h is indicated by at least one AFLP marker linked to said QTL on chromosome 1, wherein said marker is selected from the group consisting of the AFLP fragments P22M50-412h, P14M50-349h, P14M60-69h, P14M49-192h, P14M49-232h, P14M49-260e, P14M50-503h, P18M50-124h, and P14M49-114h ; wherein said QTL-2h is indicated by at least one AFLP marker-linked to said-QTL on chromosome 2, wherein said marker is selected from the group consisting of the AFLP fragments P14M60-537h, P15M48-257e, P14M49-327h, P14M49-325h, P14M61-286e, P14M61-125h, and P18M51-134h; and wherein said QTL-4h is indicated by at lease one AFLP marker linked to said QTL on chromosome 4, wherein said marker is selected from the group consisting of the AFLP fragments P18M51-169.5e, P18M51-305.4h, P14M60-262.9e, P14M61-292.7h, TG609, P14M48-345e, P14M48-177e and P18M50-147e.

4. A method of producing a *Botrytis*-resistant tomato plant comprising the steps of: detecting a QTL associated with *Botrytis*-resistance in tomato in a *Botrytis*-resistant donor tomato plant and transferring a nucleic acid comprising at least one detected QTL, from said *Botrytis*-resistant donor tomato plant to a *Botrytis*-susceptible recipient tomato plant, wherein said at least one QTL is selected from the group consisting of QTL-1h, QTL-2h, and QTL-4h; wherein said QTL-1h is indicated by at least one AFLP marker linked to said QTL on chromosome 1, wherein said marker is selected from the group consisting of the AFLP fragments P22M50-412h, P14M50-349h, P14M60-69h, P14M49-192h, P14M49-232h, P14M49-260e, P14M50-503h, P18M50-124h, and P14M49-114h ; wherein said QTL-2h is indicated by at least one AFLP marker-linked to said-QTL on chromosome 2, wherein said marker is selected from the group consisting of the AFLP fragments P14M60-537h, P15M48-257e, P14M49-327h, P14M49-325h, P14M61-286e, P14M61-125h, and P18M51-134h; and wherein said QTL-4h is indicated by at lease one AFLP marker linked to said QTL on chromosome 4, wherein said marker is selected from the group consisting of the AFLP fragments P18M51-169.5e, P18M51-305.4h, P14M60-262.9e, P14M61-292.7h, TG609, P14M48-345e, P14M48-177e and P18M50-147e.

5. The method according to claim 3, wherein said *Botrytis*-resistant donor tomato plant is selected from the group consisting of *Lycopersicon cerasiforme*, *Lycopersicon cheesmanii*, *Lycopersicon chilense*, *Lycopersicon chmielewskii*, *Lycopersicon esculentum*, *Lycopersicon hirsutum*, *Lycopersicon pennellii*, *Lycopersicon peruvianum*, *Lycopersicon pimpineffifolium* and *Solanum lycopersicoides*.

6. The method according to claim 3, wherein said *Botrytis*-resistant donor tomato plant is a wild accession of *Lycopersicon hirsutum*.

7. The method according to claim 3, wherein said *Botrytis*-susceptible recipient tomato plant is a *Lycopersicon esculentum*.

8. The method according to claim 4, wherein said transfer of nucleic acid comprises the steps of: crossing said *Botrytis*-resistant donor tomato plant with a *Botrytis*-susceptible recipient tomato plant to produce offspring plants; and selecting a plant that comprises in its genome said at least one QTL.

9. The method according to claim 8; wherein said selection comprises marker-assisted selection with a marker selected from the group consisting of the markers of Table 1.

10. The method according to claim 3, wherein said donor plant is *Lycopersicon hirsutum* LYC 4/78, and wherein said DNA transferred from said donor plant into said recipient plant comprises at least one QTL selected from the group consisting of the QTLs on chromosomes 1, 2 and 4 of *Lycopersicon hirsutum* LYC 4/78 associated with *Botrytis*-resistance.

11. A Botrytis-resistant tomato plant, or part thereof, produced by the method according to claim 3 and having a susceptibility to *Botrytis cinerea* which is at least 3 times lower than a susceptible control tomato plant of the same species.

12. A *Botrytis*-resistant tomato plant, or part thereof, having a susceptibility to *Botrytis cinerea* which is at least 3 times lower than a susceptible control tomato plant of the same species comprising within its genome at least one QTL selected from the group consisting of the QTLs on chromosomes 1, 2 and 4 of *Lycopersicon hirsutum* LYC 4/78 associated with *Botrytis*-resistance, wherein said QTL is selected from the group consisting of QTL-1h, QTL-2h, and QTL-4h; wherein said QTL-1h is indicated by at least one AFLP marker linked to said QTL on chromosome 1, wherein said marker is selected from the group consisting of the AFLP fragments P22M50-412h, P14M50-349h, P14M60-69h, P14M49-192h, P14M49-232h, P14M49-260e, P14M50-503h, P18M50-124h, and P14M49-114h; wherein said QTL- 2h is indicated by at least one AFLP marker-linked to said-QTL on chromosome 2, wherein said marker is selected from the group consisting of the AFLP fragments P14M60-537h, P15M48-257e, P14M49-327h, P14M49-325h, P14M61-286e, P14M61-125h, and P18M51-134h; and wherein said QTL-4h is indicated by at lease one AFLP marker linked to said QTL on chromosome 4, wherein said marker is selected from the group consisting of the AFLP fragments P18M51-169.5e, P18M51-305.4h, P14M60-262.9e, P14M61-292.7h, TG609, P14M48-345e, P14M48-177e and P18M50-147e ; said QTL is not in its natural genetic background.

13. The method according to claim 6, wherein said *Lycopersicon hirsutum* is *Lycopersicon hirsutum* LYC 4/78.

14. The method according to claim 6, further comprising the step of transferring a nucleic acid comprising at least one QTL associated with *Botrytis*-resistance in tomato from *Lycopersicon parviflorum*.

15. The method according to claim 7, wherein said *Lycopersicon esculentum* is an *L. esculentum* line that possesses one or more commercially desirable characteristics.

* * * * *